(12) United States Patent
Laing et al.

(10) Patent No.: US 9,648,813 B2
(45) Date of Patent: May 16, 2017

(54) REGULATION OF GENE EXPRESSION VIA UORF OF GDP-L-GALACTOSE PHOSPHORYLASE (GGP) GENE

(71) Applicant: The New Zealand Institute for Plant and Food Research Limited, Auckland (NZ)

(72) Inventors: William Alister Laing, Auckland (NZ); Roger Paul Hellens, Auckland (NZ); Richard Colin Macknight, Dunedin (NZ); Sean Michael Winsley Bulley, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 14/653,651

(22) PCT Filed: Dec. 20, 2013

(86) PCT No.: PCT/IB2013/061166
§ 371 (c)(1),
(2) Date: Jun. 18, 2015

(87) PCT Pub. No.: WO2014/097226
PCT Pub. Date: Jun. 26, 2014

(65) Prior Publication Data
US 2016/0130597 A1    May 12, 2016

Related U.S. Application Data

(60) Provisional application No. 61/740,751, filed on Dec. 21, 2012.

(51) Int. Cl.
| A01H 1/06 | (2006.01) |
| A01H 1/04 | (2006.01) |
| A01H 1/00 | (2006.01) |
| C12Q 1/68 | (2006.01) |
| C12N 15/82 | (2006.01) |
| C12N 9/12 | (2006.01) |

(52) U.S. Cl.
CPC ............ *A01H 1/06* (2013.01); *C12N 9/1241* (2013.01); *C12N 15/8238* (2013.01); *C12N 15/8243* (2013.01); *C12Q 1/6895* (2013.01)

(58) Field of Classification Search
None
See application file for complete search history.

(56) References Cited

U.S. PATENT DOCUMENTS

| 4,795,855 A | 1/1989 | Fillatti et al. |
| 4,943,674 A | 7/1990 | Houck et al. |
| 5,004,863 A | 4/1991 | Umbeck |
| 5,086,169 A | 2/1992 | Mascarenhas |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,412,085 A | 5/1995 | Allen et al. |
| 5,416,011 A | 5/1995 | Hinchee et al. |
| 5,463,174 A | 10/1995 | Moloney et al. |
| 5,536,653 A | 7/1996 | Barry et al. |
| 5,545,169 A | 8/1996 | Yarger |
| 5,545,546 A | 8/1996 | Allen et al. |
| 5,563,055 A | 10/1996 | Townsend et al. |
| 5,569,834 A | 10/1996 | Hinchee et al. |
| 5,591,616 A | 1/1997 | Hiei et al. |
| 5,608,150 A | 3/1997 | Conner |
| 5,639,952 A | 6/1997 | Quail et al. |
| 5,656,496 A | 8/1997 | Quail et al. |
| 5,750,385 A | 5/1998 | Shewmaker et al. |
| 5,750,871 A | 5/1998 | Moloney et al. |
| 5,792,935 A | 8/1998 | Arntzen et al. |
| 5,795,855 A | 8/1998 | Schneider et al. |
| 5,824,877 A | 10/1998 | Hinchee et al. |
| 5,837,848 A | 11/1998 | Ely et al. |
| 5,846,797 A | 12/1998 | Strickland |
| 5,952,543 A | 9/1999 | Firoozabady et al. |

(Continued)

FOREIGN PATENT DOCUMENTS

| WO | WO 98/55631 A1 | 12/1998 | |
| WO | WO 00/01713 A2 | 1/2000 | |
| WO | WO 00/32756 A2 | 6/2000 | |
| WO | WO 02/00894 A2 | 1/2002 | |
| WO | WO 2004/011671 A2 | 2/2004 | |
| WO | WO 2006/052914 A1 | 5/2006 | |
| WO | WO 2008/108668 | * 9/2008 | ............... C07K 4/10 |
| WO | WO 2009/143397 A2 | 11/2009 | |
| WO | WO 2011/053169 A1 | 5/2011 | |

OTHER PUBLICATIONS

Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.

Agius et al. (2003) "Engineering increased vitamin C levels in plants by overexpression of a D-galacturonic acid reductase," Nat. Biotechnol. 21:177-181.

(Continued)

*Primary Examiner* — Cathy Kingdon Worley
(74) *Attorney, Agent, or Firm* — Lathrop & Gage LLP

(57) ABSTRACT

The invention provides isolated polynucleotides comprising sequences encoding a u ORF peptides and variants and fragments thereof. The invention also provides constructs and vectors containing the polynucleotides. The invention further provides cells, plant cells and plants transformed with the polynucleotides and constructs. The invention also provides methods of using the polynucleotides to control expression of operably linked polynucleotides. The invention also provides methods of manipulating GDP-L-Galactose phosphorylase (GGP) expression and ascorbate production in plants utilizing the polynucleotides of the invention.

9 Claims, 17 Drawing Sheets

(56) References Cited

U.S. PATENT DOCUMENTS

| | | | |
|---|---|---|---|
| 5,968,830 A | 10/1999 | Dan et al. | |
| 5,981,840 A | 11/1999 | Zhao et al. | |
| 6,020,539 A | 2/2000 | Goldman et al. | |
| 6,037,522 A | 3/2000 | Dong et al. | |
| 6,074,877 A | 6/2000 | D'Halluin et al. | |
| 6,100,077 A | 8/2000 | Sturley et al. | |
| 6,127,179 A | 10/2000 | DellaPenna et al. | |
| 6,184,443 B1 | 2/2001 | Pedersen et al. | |
| 6,228,643 B1 | 5/2001 | Greenland et al. | |
| 6,229,067 B1 | 5/2001 | Sonnewald et al. | |
| 6,342,657 B1 | 1/2002 | Thomas et al. | |
| 6,344,548 B1 | 2/2002 | Farese, Jr. et al. | |
| 7,081,565 B2 | 7/2006 | Ohlrogge et al. | |
| 7,141,424 B2 | 11/2006 | Shin et al. | |
| 7,153,953 B2 | 12/2006 | Marraccini et al. | |
| 7,371,928 B2 | 5/2008 | Suh et al. | |
| 7,405,345 B2 | 7/2008 | Ohlrogge et al. | |
| 7,629,454 B2 | 12/2009 | Chan et al. | |
| 7,642,346 B2 | 1/2010 | Chaudhary et al. | |
| 7,667,097 B2 | 2/2010 | Scheirlinck et al. | |
| 7,745,697 B2 | 6/2010 | Perez et al. | |
| 8,686,125 B2 * | 4/2014 | Espley | C07K 14/415 435/243 |
| 2001/0047525 A1 | 11/2001 | Bruce et al. | |
| 2003/0115632 A1 | 6/2003 | Lardizabal et al. | |
| 2004/0067506 A1 | 4/2004 | Scheres et al. | |
| 2009/0094717 A1 | 4/2009 | Troukhan et al. | |
| 2009/0144848 A1 | 6/2009 | Kovalic et al. | |
| 2010/0024079 A1 | 1/2010 | Andersen et al. | |
| 2010/0077503 A1 * | 3/2010 | Laing | C12N 9/1241 800/278 |
| 2010/0122381 A1 | 5/2010 | Buehler et al. | |
| 2011/0167514 A1 | 7/2011 | Brover et al. | |
| 2012/0156360 A1 | 6/2012 | Roesler et al. | |
| 2015/0252378 A1 | 9/2015 | Roberts et al. | |
| 2015/0275223 A1 | 10/2015 | Roberts et al. | |
| 2015/0284736 A1 | 10/2015 | Roberts et al. | |

OTHER PUBLICATIONS

Alam et al. (1999) "Transgenic insect-resistant maintainer line (IR68899B) for improvement of hybrid rice," Plant Cell Rep. 18:572-575.

Altpeter et al. (2004) "Comparison of Transgene Expression Stability after Agrobacterium-mediated or Biolistic Gene Transfer into Perennial Ryegrass (*Lolium perenne* L.)," Developments in Plant Breeding. 11(7):255-260.

Altschul et al. (1997) "Gapped BLAST and PSI-BLAST: a new generation of protein database search programs," Nucleic Acids Res. 25:3389-3402.

Andrianov et al. (2009) "Tobacco as a production platform for biofuel: overexpression of Arabidopsis DGAT and LEC2 genes increases accumulation and shifts the composition of lipids in green biomass," Plant Biotechnol. J. 8:277-287.

Asensi-Fabado et al. (2010) "Vitamins in plants: occurrence, biosynthesis and antioxidant function," Trends Plant Sci. 15:582.

Bairoch et al. (1994) "PROSITE: recent developments," Nucleic Acids Res. 22:3583-3589.

Bartoli et al. (2005) "Ascorbate content of wheat leaves is not determined by maximal l-galactono-1,4-lactone dehydrogenase (GalLDH) activity under drought stress," Plant, Cell and Environment. 28:1073-1081.

Bartoli et al. (2006) "Inter-relationships between light and respiration in the control of ascorbic acid synthesis and accumulation in Arabidopsis thaliana leaves," J. Exp. Bot. 57:1621-1631.

Baxevanis (2001) "The Molecular Biology Database Collection: an updated compilation of biological database resources," Nucleic Acids Res. 29:1-10.

Beopoulos et al. (Mar. 31, 2011) "An overview of lipid metabolism in yeasts and its impact on biotechnological processes," Appl. Microbiol. Biotechnol. 90:1193-1206.

Birch (1997) "Plant Transformations: Problems and Strategies for Practical Applications," Ann. Rev. Plant Phys. Plant Mol. Biol. 48:297-326.

Birney et al. (2004) "GeneWise and Genomewise," Genome Res. 14:988-995.

Bolton et al. (1962) "A General Method for the Isolation of RNA Complementary to DNA," Proc. Natl. Acad. Sci. USA. 48:1390-1397.

Bouvier-Navé et al. (2000) "Expression in yeast and tobacco of plant cDNAs encoding acyl CoA:diacylglycerol acyltransferase," Eur. J. Biochem. 267:85-96.

Bowie et al. (1990) "Deciphering the message in protein sequences: tolerance to amino acid substitutions," Science. 247:1306-1310.

Browse et al. (1986) "Fatty acid composition of leaf lipids determined after combined digestion and fatty acid methyl ester formation from fresh tissue," Anal. Biochem. 152:141-145.

Bulley et al. (2009) "Gene expression studies in kiwifruit and gene over-expression in Arabidopsis indicates that GDP-L-galactose guanyltransferase is a major control point of vitamin C biosynthesis," J. Exp. Bot. 60:765-778.

Bulley et al. (Dec. 1, 2011) "Enhancing ascorbate in fruits and tubers through over-expression of the L-galactose pathway gene GDP-L-galactose phosphorylase," Plant Biotechnol. J. 10:390-397.

Cahoon et al. (2007) "Engineering oilseeds for sustainable production of industrial and nutritional feedstocks: solving bottlenecks in fatty acid flux," Current Opinion in Plant Biology. 10:236-244.

Calvo et al. (2009) "Upstream open reading frames cause widespread reduction of protein expression and are polymorphic among humans," Proc. Natl. Acad. Sci. USA. 106:7507-7512.

Cardoza et al. (2006) "Canola (*Brassica napus* L.)," Methods Mol. Biol. 343:257-266.

Cermak et al. (2011) "Efficient design and assembly of custom TALEN and other TAL effector-based constructs for DNA targeting," Nucleic Acids Res. 39(12):e82.

Christou et al. (1991) "Production of Transgenic Rice (*Oryza sativa* L.) Plants from Agronomically Important Indica and Japonica Varieties via Electric Discharge Particle Acceleration of Exogenous DNA into Immature Zygotic Embryos," Nature Biotech. 9:957-962.

Clough et al. (1998) "Floral dip: a simplified method for Agrobacterium-mediated transformation of Arabidopsis thaliana," Plant J. 16(6)735-743.

Coggiatti (1971) "Actinidia Chinensis," Ital. Agr. 108(10):935-941.—English machine translation.

Conklin (1998) "Vitamin C: a new pathway for an old antioxidant," Trends Plant Sci. 3:329-330.

Conklin et al. (1999) "Genetic evidence for the role of GDP-mannose in plant ascorbic acid (vitamin C) biosynthesis," Proc. Natl. Acad. Sci. USA 96:4198-4203.

Conklin et al. (2006) "Arabidopsis thaliana VTC4 Encodes L-Galactose-1-P Phosphatase, a Plant Ascorbic Acid Biosynthetic Enzyme," J. Biol. Chem. 281:15662-15670.

Conrad et al. (2003) "Antibody jabs for plant enzymes," Nat. Biotechnol. 21(1): 35-36.

Curtin et al. (2011) "Targeted Mutagenesis of Duplicated Genes in Soybean with Zinc-Finger Nucleases," Plant Physiol. 156:466-473.

Dan et al. (2006) "MicroTom—a high-throughput model transformation system for functional genomics," Plant Cell Reports. 25:432-441.

De Carvalho Niebel et al. (1995) "Post-transcriptional cosuppression of beta-1,3-glucanase genes does not affect accumulation of transgene nuclear mRNA," Plant Cell. 7:347-358.

Durrett et al. (2008) "Plant triacylglycerols as feedstocks for the production of biofuels," Plant J. 54:593-607.

Elble (1992) "A simple and efficient procedure for transformation of yeasts," BioTechniques. 13:18-20.

Ellerström et al. (1996) "Functional dissection of a napin gene promoter: identification of promoter elements required for embryo and endosperm-specific transcription," Plant Molecular Biology. 32(6):1019-1027.

Falquet et al. (2002) "The PROSITE database, its status in 2002," Nucleic Acids Res. 30:235-238.

Feng et al. (1987) "Progressive sequence alignment as a prerequisite to correct phylogenetic trees," J. Mol. Evol. 25:351-360.

(56) References Cited

OTHER PUBLICATIONS

Ferguson (1991) "Kiwifruit (Actinidia)," Acta Hort. 290:603-656.
Folta et al. (2006) "Characterization of LF9, an octoploid strawberry genotype selected for rapid regeneration and transformation," Planta. 224(5):1058-1067.
Fortman et al. (2008) "Biofuel alternatives to ethanol: pumping the microbial well," Trends Biotechnol. 26:375-381.
Foyer et al. (2011) "Ascorbate and Glutathione: The Heart of the Redox Hub," Plant Physiol. 155:2-18.
Frohman (1993) "Rapid amplification of complementary DNA ends for generation of full-length complementary DNAs: thermal RACE," Methods Enzymol. 218:340-356.
Gao et al. (2011) "Expression Analysis of the VTC2 and VTC5 Genes Encoding GDP-L-Galactose Phosphorylase, an Enzyme Involved in Ascorbate Biosynthesis, in Arabidopsis thaliana," Biosci. Biotechnol. Biochem. 75(9):1783-1787.
Gatzek et al. (2002) "Antisense suppression of I-galactose dehydrogenase in Arabidopsis thaliana provides evidence for its role in ascorbate synthesis and reveals light modulated I-galactose synthesis," Plant J. 30:541-553.
GenBank (Feb. 25, 2009) "unknown [*Zea mays*]," National Center for Biotechnology Information. Accession No. ACN35495. Accessible on the Internet at URL: http://www.ncbi.nlm.nih.gov/protein/ACN35495. [Last Accessed Dec. 17, 2015].
GenBank (Jul. 25, 2006) "diacylglycerol acyltransferase [Oryza sativa Japonica Group]," National Center for Biotechnology Information. Accession No. AAW47581. Accessible on the Internet at URL: http://www.ncbi.nlm.nih.gov/protein/AAW47581. [Last Accessed Dec. 17, 2015].
GenBank (Jul. 31, 2008) "010422KABA018501HT (KABA) A. deliciosa petal Actinidia deliciosa cDNA clone KABAA01850, mRNA sequence," National Center for Biotechnology Information. Accession No. FG429343. Accessible on the Internet at URL: http://www.ncbi.nlm.nih.gov/nucest/FG429343. [Last Accessed Feb. 2, 2016].
GenBank (Jul. 31, 2008) "010802KUFA010178HT (KUFA) Actinidia eriantha young fruit Actinidia eriantha cDNA clone KUFAA01017, mRNA sequence," Accession No. National Center for Biotechnology Information. FG424114. Accessible on the Internet at URL: http://www.ncbi.nlm.nih.gov/nucest/FG424114. [Last Accessed Feb. 2, 2016].
GenBank (Jul. 31, 2008) "021014KAIA007447HT (KAIA) Actinidia chinensis ripe fruit Actinidia chinensis cDNA clone KAIAA00744, mRNA sequence," National Center for Biotechnology Information. Accession No. FG460629. Accessible on the Internet at URL: http://www.ncbi.nlm.nih.gov/nucest/FG460629. [Last Accessed Feb. 2, 2016].
Genbank (Jul. 31, 2008) "030826KAZD001008AG (KAZD) Actinidia chinensis young fruit library Actinidia chinensis cDNA clone KAZDD00100, mRNA sequence," National Center for Biotechnology Information. Accession No. FG528585. Accessible on the Internet at URL: http://www.ncbi.nlm.nih.gov/nucest/FG528585. [Last Accessed Feb. 2, 2016].
GenBank (Jun. 4,2004) "010513AAXA001140HT (AAXA) Royal Gala 126 DAFB fruit core Malus domestica cDNA clone AAXA001140, mRNA sequence," National Center for Biotechnology Information. Accession No. CN890589.1. Accessible on the Internet at URL: http://www.ncbi.nlm.nih.gov/nucest/CN890589.1. [Last Accessed Feb. 2, 2016].
GenBank (Mar. 4, 2013) "Actinidia eriantha VitC-2 gene, promoter region," National Center for Biotechnology Information. Accession No. JX486682. Accessible on the Internet at URL: http://www.ncbi.nlm.nih.gov/nuccore/JX486682. [Last Accessed Feb. 2, 2016].
GenBank (May 22, 2009) "Chlamydomonas reinhardtii predicted protein (CHLREDRAFT_188099) mRNA, complete cds," National Center for Biotechnology Information. Accession No. XM_001693828.1. Accessible on the Internet at URL: http://www.ncbi.nlm.nih.gov/nuccore/XM_001693828.1. [Last Accessed Feb. 2, 2016].

Giesen et al. (1998) "A formula for thermal stability (Tm) prediction of PNA/DNA duplexes," Nucleic Acids Res. 26(21):5004-5006.
Gleave (1992) "A versatile binary vector system with a T-DNA organisational structure conducive to efficient integration of cloned DNA into the plant genome," Plant Mol. Biol. 20:1203-1207.
Gonzalez Padilla et al. (2003) "Early antibiotic selection and efficient rooting and acclimatization improve the production of transgenic plum plants (*Prunus domestica* L.)," Plant Cell Rep. 22(1):38-45.
Graham et al. (1995) "Agrobacterium-mediated transformation of soft fruit Rubus, Ribes, and Fragaria," Methods Mol. Biol. 44:129-133.
Guiheneuf et al. (2011) "Cloning and molecular characterization of a novel acyl-CoA:diacylglycerol acyltransferase 1-like gene (PtDGAT1) from the diatom Phaeodactylum tricornutum," The FEBS Journal. 278:3651-3666.
Halford et al. (1998) "SNF1-related protein kinases: global regulators of carbon metabolism in plants?" Plant Mol. Biol. 37:735-748.
Hellens et al. (2000) "pGreen: a versatile and flexible binary Ti vector for Agrobacterium-mediated plant transformation," Plant Mol. Biol. 42:819-832.
Hellens et al. (2005) "Transient expression vectors for functional genomics, quantification of promoter activity and RNA silencing in plants," Plant Methods. 1:13 pp. 1-14.
Henikoff et al. (1992) "Amino acid substitution matrices from protein blocks," Proc. Natl. Acad. Sci. USA. 89:10915-10919.
Herrera-Estrella et al. (1993) "Expression of chimaeric genes transferred into plant cells using a Ti-plasmid-derived vector," Nature. 303:209-213.
Hofmann et al. (1999) "The PROSITE database, its status in 1999," Nucleic Acids Res. 27:215-219.
Horsch et al. (1985) "A simple and general method for transferring genes into plants," Science. 227:1229-1231.
Hu et al. (2005) "The pivotal roles of the plant S-adenosylmethionine decarboxylase 5' untranslated leader sequence in regulation of gene expression at the transcriptional and posttranscriptional levels," Plant Physiol. 138:276-286.
Huang (1994) "On Global Sequence Alignment," Computer Applications in the Biosciences. 10:227-235.
Hulzink et al. (2003) "In silico identification of putative regulatory sequence elements in the 5'-untranslated region of genes that are expressed during male gametogenesis," Plant Physiol. 132:75-83.
Imai et al. (1998) "L-galactono-gamma-lactone dehydrogenase from sweet potato: purification and cDNA sequence analysis," Plant and Cell Physiology. 39:1350-1358.
International Preliminary Report on Patentability corresponding to International Patent Application No. PCT/IB2013/061166, completed Feb. 24, 2015.
International Search Report with Written Opinion corresponding to International Patent Application No. PCT/IB2013/061166, mailed Aug. 8, 2014.
Ivanov et al. (2008) "uORFs with unusual translational start codons autoregulate expression of eukaryotic ornithine decarboxylase homologs," Proc. Natl. Acad. Sci. USA. 105:10079-10084.
James et al. (Sep. 27, 2010) "Disruption of the Arabidopsis CGI-58 homologue produces Chanarin-Dorfman-like lipid droplet accumulation in plants," Proc. Natl. Acad. Sci. USA. 107:17833-17838.
Jang et al. (2006) "Functional classification, genomic organization, putatively cis-acting regulatory elements, and relationship to quantitative trait loci, of sorghum genes with rhizome-enriched expression," Plant Physiol. 142:1148-1159.
Jeanmougin et al. (1998) "Multiple sequence alignment with Clustal X," Trends Biochem. Sci. 23:403-405.
Jobling et al. (2003) "Immunomodulation of enzyme function in plants by single-domain antibody fragments," Nat. Biotechnol. 21(1):77-80.
Jones et al. (1998) "The effect of chimeric transgene architecture on co-ordinated gene silencing," Planta. 204:499-505.
Josefsson et al. (1987) "Structure of a gene encoding the 1.7 S storage protein, napin, from Brassica napus," J. Biol. Chem. 262(25):12196-12201.

(56) References Cited

OTHER PUBLICATIONS

Jouvenot et al. (2003) "Targeted regulation of imprinted genes by synthetic zinc-finger transcription factors," Gene Therapy. 10:513-522.
Kaup et al. (2002) "A role for diacylglycerol acyltransferase during leaf senescence," Plant Physiol. 129(4):1616-1626.
Keller et al. (1999) "Antisense inhibition of the GDP-mannose pyrophosphorylase reduces the ascorbate content in transgenic plants leading to developmental changes during senescence," Plant J. 19:131-141.
Kola et al. (1988) "New varieties of Actinidia kolomikta—one of the richest sources of vitamin C," Nahrung. 32(5):513-515.
Krens et al. (1997) "Transgenic caraway, Carum carvi L.: a model species for metabolic engineering," Plant Cell Rep. 17:39-43.
Kumar et al. (1996) "Potato plants expressing antisense and sense S-adenosylmethionine decarboxylase (SAMDC) transgenes show altered levels of polyamines and ethylene: antisense plants display abnormal phenotypes," Plant J. 9(2):147-158.
Laing et al. (2004) "A highly specific L-galactose-1-phosphate phosphatase on the path to ascorbate biosynthesis," Proc. Natl. Acad. Sci. USA. 101:16976-16981.
Laing et al. (2007) "The missing step of the L-galactose pathway of ascorbate biosynthesis in plants, an L-galactose guanyltransferase, increases leaf ascorbate content," Proc. Natl. Acad. Sci. USA. 104:9534-9539.
Li et al. (1996) "Genetic transformation of cassava (Manihot esculenta Crantz)," Nat. Biotechnol. 14:736-740.
Li et al. (2001) "A fast neutron deletion mutagenesis-based reverse genetics system for plants," Plant Journal. 27(3):235-242.
Li et al. (2003) "Transgenic rose lines harboring an antimicrobial protein gene, Ace-AMP1, demonstrate enhanced resistance to powdery mildew (Sphaerotheca pannosa)," Planta, 218:226-232.
Li et al. (Jan. 27, 2010) "DGAT1, DGAT2 and PDAT expression in seeds and other tissues of epoxy and hydroxy fatty acid accumulating plants," Lipids. 45:145-157.
Li et al. (May 7, 2012) "High-efficiency TALEN-based gene editing produces disease-resistant rice," Nat. Biotechnol. 30:390-392.
Llave et al. (2002) "Cleavage of Scarecrow-like mRNA targets directed by a class of Arabidopsis miRNA," Science. 297:2053-2056.
Loewus et al. (1961) "The metabolism of p-galacturonic acid and its methyl ester in the detached ripening strawberry," Arch. Biochem. Biophys. 95:483-493.
Lorence et al. (2004) "myo-inositol oxygenase offers a possible entry point into plant ascorbate biosynthesis," Plant Physiol. 134:1200-1205.
Lung et al. (2006) "Diacylglycerol acyltransferase: a key mediator of plant triacylglycerol synthesis," Lipids. 41(12):1073-1088.
Mahfouz et al. (2011) "De novo-engineered transcription activator-like effector (TALE) hybrid nuclease with novel DNA binding specificity creates double-strand breaks," Proc. Natl. Acad. Sci. USA. 108:2623-2628.
Mandl et al. (2009) "Vitamin C: update on physiology and pharmacology," Br. J. Pharmacol. 157:1097-1110.
Matsuda et al. (2005) "Development of an Agrobacterium-mediated transformation method for pear (Pyrus communis L.) with leaf-section and axillary shoot-meristem explants," Plant Cell Rep. 24(1):45-51.
McFie et al. (Sep. 27, 2010) "Topological orientation of acyl-CoA:diacylglycerol acyltransferase-1 (DGAT1) and identification of a putative active site histidine and the role of the n terminus in dimer/tetramer formation," J. Biol. Chem. 285:37377-37389.
McIntyre (1996) "Strategies for the suppression of peroxidase gene expression in tobacco. I. Designing efficient ribozymes," Transgenic Res. 5:257-262.
Michelmore et al. (1987) "Transformation of lettuce (Lactuca sativa) mediated by Agrobacterium tumefaciens," Plant Cell Rep. 6:439-442.
Moloney et al. (1989) "High efficiency transformation of Brassica napus using Agrobacterium vectors," Plant Cell Rep. 8:238-242.
Mu et al. (2008) "LEAFY COTYLEDON1 is a key regulator of fatty acid biosynthesis in Arabidopsis," Plant Physiol. 148:1042-1054.
Muggleston et al. (1998) "Breeding new kiwifruit cultivars: the creation of Hort16A and Tomua," Orchardist of New Zeland. 71(8):38-40.
Müller-Moulé (2008) "An expression analysis of the ascorbate biosynthesis enzyme VTC2," Plant Mol. Biol. 68:31-41.
Napoli et al. (1990) "Introduction of a Chimeric Chalcone Synthase Gene into Petunia Results in Reversible Co-Suppression of Homologous Genes in trans," Plant Cell. 2:279-289.
Needleman et al. (1970) "A general method applicable to the search for similarities in the amino acid sequence of two proteins," J. Mol. Biol. 48:443-453.
Nielsen et al. (1991) "Sequence-selective recognition of DNA by strand displacement with a thymine-substituted polyamide," Science. 254(5037):1497-1500.
Niu et al. (1998) "Transgenic peppermint (Mentha x piperita L.) plants obtained by cocultivation with Agrobacterium tumefaciens," Plant Cell Rep. 17:165-171.
Notredame et al. (2000) "A novel method for fast and accurate multiple sequence alignment," J. Mol. Biol. 302:205-217.
Nykiforuk et al. (2002) "Characterization of cDNAs encoding diacylglycerol acyltransferase from cultures of Brassica napus and sucrose-mediated induction of enzyme biosynthesis," Biochimica et Biophysica Acta. 1580:95-109.
Ohlrogge et al. (2009) "Energy. Driving on biomass," Science. 324:1019-1020.
Oosumi et al. (2006) "High-efficiency transformation of the diploid strawberry (Fragaria vesca) for functional genomics," Planta. 223(6):1219-1230.
Orlikowska et al. (1995) "Factors influencing Agrobacterium tumefaciens-mediated transformation and regeneration of the safflower cultivar 'centennial,'" Plant Cell Tissue and Organ Culture. 40:85-91.
Ortiz et al. (1996) "Hygromycin resistance as an efficient selectable marker for wheat stable transformation," Plant Cell Rep. 15:877-881.
Pena et al. (1995) "High efficiency Agrobacterium-mediated transformation and regeneration of citrus," Plant Sci.104:183-191.
Potato Genome Sequencing Consortium (2011) "Genome sequence and analysis of the tuber crop potato," Nature. 475:189-195.
Potrykus et al.: Eds. (1995) Gene Transfer to Plants. Springer-Verlag. Berlin, Germany. pp. i-xxii.
Rahmani et al. (2009) "Sucrose control of translation mediated by an upstream open reading frame-encoded peptide," Plant Physiol. 150:1356-1367.
Ramesh et al. (2006) "Improved methods in Agrobacterium-mediated transformation of almond using positive (mannose/pmi) or negative (kanamycin resistance) selection-based protocols," Plant Cell Rep. 25(8):821-828.
Rassam et al. (2005) "Variation in ascorbic acid and oxalate levels in the fruit of Actinidia chinensis tissues and genotypes," J. Agric. Food Chem. 53:2322-2326.
Rice et al. (2000) "EMBOSS: The European Molecular Biology Open Software Suite," Trends in Genetics. 16(6):276-277.
Rodriguez et al. (1992) "Determination of vitamin C and organic acids in various fruits by HPLC," J. Chromatogr. Sci. 30:433-437.
Rose et al. (1989) "KAR2, a karyogamy gene, is the yeast homolog of the mammalian BiP/GRP78 gene," Cell. 57:1211-1221.
Rozen et al. (2000) "Primer3 on the WWW for general users and for biologist programmers," Methods Mol. Biol. 132:365-386.
Salse et al. (2008) "Identification and characterization of shared duplications between rice and wheat provide new insight into grass genome evolution," Plant Cell. 20:11-24.
Sandager et al. (2002) "Storage lipid synthesis is non-essential in yeast," The Journal of Biological Chemistry. 277:6478-6482.
Sander et al. (2011) "Selection-free zinc-finger-nuclease engineering by context-dependent assembly (CoDA)," Nat. Methods. 8:67-69.
Sanjaya et al. (Oct. 2011) "Increasing the energy density of vegetative tissues by diverting carbon from starch to oil biosynthesis in transgenic Arabidopsis," Plant Biotechnol. J. 9:874-883.

(56) References Cited

OTHER PUBLICATIONS

Santos-Mendoza et al. (2008) "Deciphering gene regulatory networks that control seed development and maturation in Arabidopsis," Plant J. 54:608-620.
Schenk et al. (2001) "Promoters for pregenomic RNA of banana streak badnavirus are active for transgene expression in monocot and dicot plants," Plant Molecular Biology. 47:399-412.
Schrott (1995) "Selectable Marker and Reporter Genes," Ch. 31 In; Potrykus et al.: Eds. Gene Transfer to Plants. Springer-Verlag. Berlin, Germany. pp. 325-336.
Scott et al. (Oct. 2010) "Elevation of oil body integrity and emulsion stability by polyoleosins, multiple oleosin units joined in tandem head-to-tail fusions," Plant Biotechnology Journal. 8:912-927.
Shockey et al. (2006) "Tung tree DGAT1 and DGAT2 have nonredundant functions in triacylglycerol biosynthesis and are localized to different subdomains of the endoplasmic reticulum," Plant Cell. 18:2294-2313.
Smeekens et al. (2010) "Sugar signals and molecular networks controlling plant growth," Curr. Opin. Plant Biol. 13:273-278.
Smeets et al. (1997) "Developmental Regulation of Lectin and Alliinase Synthesis in Garlic Bulbs and Leaves," Plant Physiol. 113:765-771.
Snowden et al. (2005) "The Decreased apical dominance1/Petunia hybrida Carotenoid Cleavage Dioxygenase8 Gene Affects Branch Production and Plays a Role in Leaf Senescence, Root Growth, and Flower Development," The Plant Cell. 17:746-759.
Song et al. (2005) "Transformation of Montmorency sour cherry (*Prunus cerasus* L.) and Gisela 6 (P. cerasus x P. canescens) cherry rootstock mediated by Agrobacterium tumefaciens," Plant Cell Rep. 25(2):117-123.
Spano et al. (1997) "Phenology and fruit quality of kiwifruit under different environments," Acta Hort. 444:501-506.
Tatusova et al. (1999) "Blast 2 sequences—a new tool for comparing protein and nucleotide sequences," FEMS Microbiol. Lett. 174:247-250.
Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.
Thompson et al. (1994) "CLUSTAL W: improving the sensitivity of progressive multiple sequence alignment through sequence weighting, position-specific gap penalties and weight matrix choice," Nucleic Acids Res. 22:4673-4680.
Thompson et al. (1997) "The CLUSTAL_X windows interface: flexible strategies for multiple sequence alignment aided by quality analysis tools," Nucleic Acids Res. 25:4876-4882.
Till et al. (2003) "High-throughput TILLING for functional genomics," Methods Mol. Biol. 236:205-220.
Tran et al. (2008) "Conserved upstream open reading frames in higher plants," BMC Genomics. 9:361.
Triglia et al. (1988) "A procedure for in vitro amplification of DNA segments that lie outside the boundaries of known sequences," Nucleic Acids Res. 16:8186.
Tzfira et al. (May 2012) "Genome modifications in plant cells by custom-made restriction enzymes," Plant Biotechnol. J. 10:373-389.
Velasco et al. (2010) "The genome of the domesticated apple (Malus xdomestica Borkh.)," Nat. Genet. 42:833-839.
Wang et al. (2006) "Transformation of Actinidia eriantha: a potential species for functional genomics studies in Actinidia," Plant Cell Rep. 25(5):425-431.
Wang et al. (2009) "Maize Transformation," In; Handbook of Maize. Bennetzen, J. L.; Hake, S. C.: Eds. Springer-Verlag. New York, New York. pp. 609-639.
Watanabe et al. (2006) "Characterization of a GDP-d-mannose 3',5'-epimerase from rice," Phytochemistry. 67:338-346.
Wheeler et al. (1998) "The biosynthetic pathway of vitamin C in higher plants," Nature. 393:365-369.
Wheeler et al. (2001) "Database resources of the National Center for Biotechnology Information," Nucleic Acids Res. 29:11-16.
Winichayakul et al. (2009) "Head-to-tail fusions of camelid antibodies can be expressed in planta and bind in rumen fluid," Biotechnol. Appl. Biochem. 53:111-122.
Wolucka et al. (2001) "A high-performance liquid chromatography radio method for determination of L-ascorbic acid and guanosine 5'-diphosphate-l-galactose, key metabolites of the plant vitamin C pathway," Anal. Biochem. 294:161-168.
Wolucka et al. (2003) "GDP-mannose 3',5'-epimerase forms GDP-L-gulose, a putative intermediate for the de novo biosynthesis of vitamin C in plants," J. Biol. Chem. 278:47483-47490.
Xu et al. (2008) "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content," Plant Biotechnol. J. 6:799-818.
Yang et al. (2009) "Turnover of fatty acids during natural senescence of Arabidopsis, Brachypodium, and switchgrass and in Arabidopsis beta-oxidation mutants," Plant Physiol. 150:1981-1989.
Yao et al. (1995) "Regeneration of transgenic plants from the commercial apple cultivar Royal Gala," Plant Cell Reports. 14:407-412.

\* cited by examiner

>Tomato GGP 5'UTR
Atttgttcggtatactgtaaccccctgtttgcgattggccttgtagccccgttttacatcttccagagactccatttgtatcggttca
catacagtagcaaagcgccattatcttactctaccccattggcaaacccacagccacaatttttccaatcctccattatcccttctac
aattttctatataaatacccacatctctctgctctactcccttattatcaacaacaaccaccaaatttcttcttttttttcttcgatagta
gcaatctatcaacaaaaacagagacccccatcacaagaatcttggaattttagtgttgggtttaagaggaaaaggggttattgt
attttgcagttttgagggtaaagcccagtttaacaagttgtagacatcacggctatacacaaagtaaaccgccgaccact
tttacatgttccagcagtacgtcgtaagggttgtgtaacagctactaaccctgcgccgcacggtggacgtggcg
ctttgccttctgaaggtggtagtccttccgacctcctcttccttgccggcggcggttctttcctctccttctcctacta
gatatagttatacttactatagatctctagcttattacgtacagttgtatctagtattctattgattattcgaagaaaacacacaaa
aagaagtaaagcc (SEQ ID NO: 126)

>Potato GGP 5'UTR
Taaggggtgcttatataaagttggggagtctaccaatgagacgaactcattgaccaaatacgtctgcaggagaaagacca
ccggagcaccaaacgccacccaacaaccacccattaaattcttccagaaaaaaacatcttcctcaaaattatcgatgaaggat
cgttccttagtagttgttcgttgatcctacaaattcaatacggctcttcttggatctttcgtttgtattctcacaattcatca
tcaccgcaaagtgttgaccttaatccaactcttctggtggacgataagcaccggaccccttcccctcacggagg
tagggtgcctcacccgctgaaggcggttgccctccgatctcctcttcctcgccggcggcggtccaattcttcct
ttctctttctccttctcctaattttcgtgtaagaattgtattttgattatccatccaagaacaggaccgcc (SEQ ID NO:
127)

>Apple GGP 5'UTR
Ccacggtacacccctcagccacgaacaccccttcttctccccacacctataaatccaccccctcatctcctccccacaccccactc
acttcagttcgaaacaggcgatcctcgcctttctgggttgtttcctattttatctgagggagaagaaaggaaggtgtttgatcaa
ttttttggtatattttagggggtaagacccaggttcgacgagttgtagacatcacggctatacacggagctcctcggccgc
tcattcatgtccgggctgtccgacgaaagggttgtgtaattgagagcaacccttcgccgcacggcgggcgtgg
cgctttgccttccgaaggcggtagcccctccgacctgctcttcctcgctggtggcggttctgcatcctctgttttct
cttctgcttatattagcttttttagactttcttggttagattcttaggagattttagagatttttttcttctataaagcgcacgagta
gatcgtattgttgttttcgggggttttgggtttggtggtgtttgattttactgagaattaagaaaaaataaaaggaaaaaaaa
gagagagagaaagaaggggagggagcatgcc (SEQ ID NO: 128)

SEQUENCE LISTING

<160> NUMBER OF SEQ ID NOS: 143

<210> SEQ ID NO 1
<211> LENGTH: 60
<212> TYPE: PRT
<213> ORGANISM: Actinidia eriantha

<400> SEQUENCE: 1

Thr Ala Ile Phe Gly Val Ser Arg Ala Leu Val His Val Arg Ser Val
1               5                   10                  15

Arg Arg Lys Gly Cys Val Val Glu Ser Asn Pro Ser Pro His Gly Gly
            20                  25                  30

Arg Gly Ala Leu Pro Ser Glu Gly Gly Ser Pro Ser Asp Leu Leu Phe
        35                  40                  45

Leu Ala Gly Gly Gly His Phe Ala Phe Ser Val Tyr
    50                  55                  60

<210> SEQ ID NO 2
<211> LENGTH: 62
<212> TYPE: PRT
<213> ORGANISM: Cucumis sativus

<400> SEQUENCE: 2

Thr Ala Ile His Val Val Ser Arg Ser Phe Phe His Val Arg Ala Val
1               5                   10                  15

Arg Arg Lys Gly Cys Ile Thr Pro Thr Asn Pro Ser Pro His Gly Gly
            20                  25                  30

Arg Gly Ala Leu Pro Ser Glu Gly Gly Ser Pro Ser Asp Leu Leu Phe
        35                  40                  45

Leu Ala Gly Gly Gly Phe Ser Cys Phe Phe Ser Ser Ser Tyr
    50                  55                  60

<210> SEQ ID NO 3
<211> LENGTH: 58
<212> TYPE: PRT
<213> ORGANISM: Glycine max

<400> SEQUENCE: 3

Thr Ala Ile Leu Arg Val Ser Arg Ser Leu Ile His Val Pro Thr Val
1               5                   10                  15

Arg Arg Arg Thr Gly Cys Val Thr Ala Thr Asn Pro Ser Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Gly Ser Ala Val Phe
    50                  55

```
<210> SEQ ID NO 4
<211> LENGTH: 61
<212> TYPE: PRT
<213> ORGANISM: Solanum lycopersicum

<400> SEQUENCE: 4

Thr Ala Ile His Lys Val Asn Arg Arg Pro Leu Leu His Val Pro Ala
1               5                   10                  15

Val Arg Arg Lys Gly Cys Val Thr Ala Thr Asn Pro Ala Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Ser Phe Leu Ser Phe Ser Tyr
    50                  55                  60

<210> SEQ ID NO 5
<211> LENGTH: 59
<212> TYPE: PRT
<213> ORGANISM: Vitis vinifera

<400> SEQUENCE: 5

Thr Ala Ile Gln Arg Ile Pro Pro Leu Ile His Val Arg Ala Val
1               5                   10                  15

Arg Arg Lys Gly Cys Val Ile Glu Ser Asn Pro Ser Pro His Gly Gly
            20                  25                  30

Arg Gly Ala Leu Pro Ser Glu Gly Gly Ser Pro Ser Asp Leu Leu Phe
        35                  40                  45

Leu Ala Gly Gly Ser Asn Ala Phe Leu Cys
    50                  55

<210> SEQ ID NO 6
<211> LENGTH: 64
<212> TYPE: PRT
<213> ORGANISM: Arabidopsis thaliana

<400> SEQUENCE: 6

Thr Ala Ile His Gly Ile Ser Arg Gly Val Ser Ser His Val His Ile
1               5                   10                  15

Val Arg Gln Lys Gly Cys Leu Ile Glu Thr Asn Pro Leu Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Ser Ser Phe Asn Phe Ser Phe Arg Phe
    50                  55                  60

<210> SEQ ID NO 7
<211> LENGTH: 57
<212> TYPE: PRT
<213> ORGANISM: Arabidopsis thaliana

<400> SEQUENCE: 7

Thr Ala Ile Tyr Gly Ile Lys Pro Arg Pro Leu Ser Phe His Val Gln
1               5                   10                  15

Arg Lys Gly Cys Leu Ile Ile Thr Asn Pro Leu Pro His Gly Gly Arg
            20                  25                  30

Gly Ala Leu Pro Ser Glu Gly Gly Ser Pro Ser Asp Leu Leu Phe Leu
        35                  40                  45

Ala Gly Gly Gly Ser Thr Asn Ser His
    50                  55
```

<210> SEQ ID NO 8
<211> LENGTH: 64
<212> TYPE: PRT
<213> ORGANISM: Malus x domesticus

<400> SEQUENCE: 8

Thr Ala Ile Pro Arg Ala Pro Arg Pro Leu Val His Val Arg Gly Val
1               5                   10                  15

Gly Arg Lys Gly Cys Val Ile Glu Ser Asn Pro Ser Pro His Gly Gly
            20                  25                  30

Arg Gly Ala Leu Pro Ser Glu Gly Gly Ser Pro Ser Asp Leu Leu Phe
        35                  40                  45

Leu Ala Gly Gly Ser Pro Ser Ser Val Phe Leu Phe Cys Phe Tyr
    50                  55                  60

<210> SEQ ID NO 9
<211> LENGTH: 61
<212> TYPE: PRT
<213> ORGANISM: Medicago truncatula

<400> SEQUENCE: 9

Thr Ala Phe Leu Arg Val Tyr Arg Ser Leu Ser His Ala Arg Thr Val
1               5                   10                  15

Arg Arg Lys Gly Cys Cys Leu Thr Pro Thr Asn Pro Ser Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Val Phe Ala Pro Ser Ser Phe
    50                  55                  60

<210> SEQ ID NO 10
<211> LENGTH: 63
<212> TYPE: PRT
<213> ORGANISM: Populus trichocarpa

<400> SEQUENCE: 10

Thr Ala Ile His Gly Val Thr Arg Ser Leu Ile His Val Arg Ala Val
1               5                   10                  15

Arg Arg Lys Gly Cys Val Ile Glu Ser Ser Asn Pro Ser Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Gly Phe Phe Phe Cys Leu Val Val Val
    50                  55                  60

<210> SEQ ID NO 11
<211> LENGTH: 80
<212> TYPE: PRT
<213> ORGANISM: Picea sitchensis

<400> SEQUENCE: 11

Thr Ala Ile Lys Arg Ile Leu Arg Phe Gln Pro His Asp Arg Arg Arg
1               5                   10                  15

Ile Leu Arg Ser Arg Asn Ala Gly Cys Ala Leu Glu Ser Thr Pro Ser
            20                  25                  30

Pro His Gly Gly Arg Gly Ala Leu Pro Ser Glu Gly Gly Ser Pro Ser
        35                  40                  45

Asp Leu Leu Phe Leu Ala Gly Gly Gly Cys Asp Arg Ala Leu Phe Cys
    50                  55                  60

```
Leu Ala His Pro Phe Leu Leu Ser Arg Gly Glu Ile Ile Trp Glu Arg
 65                  70                  75                  80

<210> SEQ ID NO 12
<211> LENGTH: 57
<212> TYPE: PRT
<213> ORGANISM: Physcomitrella patens

<400> SEQUENCE: 12

Met Ser Lys Asp Phe Tyr Arg Ala Gly Ile Gln Leu Ser Arg Ser Leu
  1               5                  10                  15

Ser Ser Ser Leu Ser Leu His Gly Gly Arg Gly Ala Ala Pro Ser Glu
             20                  25                  30

Gly Gly Arg Pro Ser Asp Leu Ser Ala Leu Ala Gly Gly Gly Phe Leu
         35                  40                  45

Ser Asn Phe His His Gly Ala Asp Pro
     50                  55

<210> SEQ ID NO 13
<211> LENGTH: 60
<212> TYPE: PRT
<213> ORGANISM: Actinidia arguta

<400> SEQUENCE: 13

Thr Ala Ile Leu Gly Val Ser Arg Pro Leu Ile His Val Arg Ser Val
  1               5                  10                  15

Arg Arg Lys Gly Cys Val Val Glu Ser Asn Pro Ser Pro His Gly Gly
             20                  25                  30

Arg Gly Ala Leu Pro Ser Glu Gly Gly Ser Pro Ser Asp Leu Leu Phe
         35                  40                  45

Leu Ala Gly Gly Gly His Phe Ala Phe Ser Val Tyr
     50                  55                  60

<210> SEQ ID NO 14
<211> LENGTH: 60
<212> TYPE: PRT
<213> ORGANISM: Actinidia eriantha

<400> SEQUENCE: 14

Thr Ala Ile Leu Gly Val Ser Arg Pro Leu Ile His Val Arg Ser Val
  1               5                  10                  15

Arg Arg Lys Gly Cys Val Val Glu Ser Asn Pro Ser Pro His Gly Gly
             20                  25                  30

Arg Gly Ala Leu Pro Ser Glu Gly Gly Ser Pro Ser Asp Leu Leu Phe
         35                  40                  45

Leu Ala Gly Gly Gly His Phe Ala Phe Ser Val Tyr
     50                  55                  60

<210> SEQ ID NO 15
<211> LENGTH: 60
<212> TYPE: PRT
<213> ORGANISM: Actinidia chinensis

<400> SEQUENCE: 15

Thr Ala Ile Leu Gly Val Ser Arg Pro Leu Ile His Val Arg Ser Val
  1               5                  10                  15

Arg Arg Lys Gly Cys Val Val Glu Ser Asn Pro Ser Pro His Gly Gly
             20                  25                  30

Arg Gly Ala Leu Pro Ser Glu Gly Gly Ser Pro Ser Asp Leu Leu Phe
```

35                  40                  45

Leu Ala Gly Gly Gly His Phe Ala Phe Ser Val Tyr
 50                  55                  60

<210> SEQ ID NO 16
<211> LENGTH: 64
<212> TYPE: PRT
<213> ORGANISM: Fragaria vulgaris

<400> SEQUENCE: 16

Thr Ala Ile His Arg Val Ser Arg Pro Leu Ile His Val Arg Arg Thr
 1               5                  10                  15

Val Arg Arg Lys Gly Cys Val Ile Glu Ser Asn Pro Ser Pro His Gly
                20                  25                  30

Gly Arg Gly Ala Leu Pro Ser Glu Gly Gly Ser Pro Ser Asp Leu Leu
            35                  40                  45

Phe Leu Ala Gly Gly Gly Val His Val Ser Asp Leu Arg Phe Phe Phe
 50                  55                  60

<210> SEQ ID NO 17
<211> LENGTH: 61
<212> TYPE: PRT
<213> ORGANISM: Solanum tuberosum

<400> SEQUENCE: 17

Thr Ala Ile His Lys Val Asn Arg Arg Pro Leu Leu His Val Pro Ala
 1               5                  10                  15

Val Arg Arg Lys Gly Cys Val Thr Ala Thr Asn Pro Ala Pro His Gly
                20                  25                  30

Gly Arg Gly Ala Leu Pro Ser Glu Gly Gly Ser Pro Ser Asp Leu Leu
            35                  40                  45

Phe Leu Ala Gly Gly Gly Ser Phe Leu Ser Phe Ser Tyr
 50                  55                  60

<210> SEQ ID NO 18
<211> LENGTH: 55
<212> TYPE: PRT
<213> ORGANISM: Chlamydomonas reinhardtii

<400> SEQUENCE: 18

Met His Leu Arg Glu Pro Val Lys Thr Ala Phe Ser Glu Ala Ala Arg
 1               5                  10                  15

Val Gln Ser Ala Ala Ser Gln Pro Ala Thr Ala Asn Arg Cys Ser Gly
                20                  25                  30

Gly Arg Gly Ala Ala Pro Ser Cys Gly Gly Lys Pro Lys Asp Ala Leu
            35                  40                  45

Ser Lys Ala Gly Gly Gly Gln
 50                  55

<210> SEQ ID NO 19
<211> LENGTH: 58
<212> TYPE: PRT
<213> ORGANISM: Zea mays
<220> FEATURE:
<221> NAME/KEY: misc_feature
<222> LOCATION: (56)..(56)
<223> OTHER INFORMATION: Xaa can be any naturally occurring amino acid

<400> SEQUENCE: 19

Thr Ala Ser Val Ala Ala Pro Arg Arg Gly Pro Ala Ala Ala Gln Val
 1               5                  10                  15

Glu Pro Thr Gly Thr Ile Ala Ser Ala Val Ala Ser Ser Pro Ala Pro
            20                  25                  30

His Gly Gly Arg Gly Ala Leu Pro Ser Ala Gly Gly Ser Pro Ser Asp
        35                  40                  45

Leu Leu Phe Leu Ala Gly Gly Xaa Arg Leu
    50                  55

<210> SEQ ID NO 20
<211> LENGTH: 61
<212> TYPE: PRT
<213> ORGANISM: Selaginella moellendorffii

<400> SEQUENCE: 20

Thr Ala Ser Ile Glu Leu Leu Ser Arg His Pro Ile Ile Cys Tyr Gly
1               5                   10                  15

His Ser Val Ser Ser Cys Lys Thr Leu Leu Ser Ser Leu Ser Cys His
            20                  25                  30

Gly Gly Arg Gly Ala Ser Pro Ser Glu Gly Gly His Pro Ser Asp Leu
        35                  40                  45

Thr Phe Leu Ala Gly Gly Gly Leu Leu Leu Gly Ala Pro
    50                  55                  60

<210> SEQ ID NO 21
<211> LENGTH: 28
<212> TYPE: PRT
<213> ORGANISM: Actinidia eriantha

<400> SEQUENCE: 21

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 22
<211> LENGTH: 28
<212> TYPE: PRT
<213> ORGANISM: Cucumis sativus

<400> SEQUENCE: 22

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 23
<211> LENGTH: 28
<212> TYPE: PRT
<213> ORGANISM: Glycine max

<400> SEQUENCE: 23

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 24
<211> LENGTH: 28
<212> TYPE: PRT
<213> ORGANISM: Solanum lycopersicum

<400> SEQUENCE: 24

Asn Pro Ala Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 25
<211> LENGTH: 28
<212> TYPE: PRT
<213> ORGANISM: Vitis vinifera

<400> SEQUENCE: 25

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 26
<211> LENGTH: 28
<212> TYPE: PRT
<213> ORGANISM: Arabidopsis thaliana

<400> SEQUENCE: 26

Asn Pro Leu Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 27
<211> LENGTH: 28
<212> TYPE: PRT
<213> ORGANISM: Arabidopsis thaliana

<400> SEQUENCE: 27

Asn Pro Leu Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 28
<211> LENGTH: 28
<212> TYPE: PRT
<213> ORGANISM: Malus x domesticus

<400> SEQUENCE: 28

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 29
<211> LENGTH: 28
<212> TYPE: PRT
<213> ORGANISM: Medicago truncatula

<400> SEQUENCE: 29

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 30

```
<211> LENGTH: 28
<212> TYPE: PRT
<213> ORGANISM: Populus trichocarpa

<400> SEQUENCE: 30

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 31
<211> LENGTH: 28
<212> TYPE: PRT
<213> ORGANISM: Picea sitchensis

<400> SEQUENCE: 31

Thr Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 32
<211> LENGTH: 28
<212> TYPE: PRT
<213> ORGANISM: Physcomitrella patens

<400> SEQUENCE: 32

Ser Leu Ser Leu His Gly Gly Arg Gly Ala Ala Pro Ser Glu Gly Gly
1               5                   10                  15

Arg Pro Ser Asp Leu Ser Ala Leu Ala Gly Gly Gly
            20                  25

<210> SEQ ID NO 33
<211> LENGTH: 28
<212> TYPE: PRT
<213> ORGANISM: Actinidia arguta

<400> SEQUENCE: 33

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 34
<211> LENGTH: 28
<212> TYPE: PRT
<213> ORGANISM: Actinidia eriantha

<400> SEQUENCE: 34

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 35
<211> LENGTH: 28
<212> TYPE: PRT
<213> ORGANISM: Actinidia chinensis

<400> SEQUENCE: 35

Asn Pro Ser Pro His Gly Gly Arg Gly Ala Leu Pro Ser Glu Gly Gly
1               5                   10                  15
```

-continued

```
Ser Pro Ser Asp Leu Leu Phe Leu Ala Gly Gly Gly
            20                  25

<210> SEQ ID NO 36
<211> LENGTH: 28
<212> TYPE: PRT
<213> ORGANISM: Fragaria vulgaris

<400> SEQUENCE: 36

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 37
<211> LENGTH: 28
<212> TYPE: PRT
<213> ORGANISM: Solanum tuberosum

<400> SEQUENCE: 37

Asn Pro Ala Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 38
<211> LENGTH: 28
<212> TYPE: PRT
<213> ORGANISM: Chlamydomonas reinhardtii

<400> SEQUENCE: 38

Ala Asn Arg Cys Ser Gly Gly Arg Gly Ala Ala Pro Ser Cys Gly Gly
1               5                   10                  15

Lys Pro Lys Asp Ala Leu Ser Lys Ala Gly Gly Gly
            20                  25

<210> SEQ ID NO 39
<211> LENGTH: 26
<212> TYPE: PRT
<213> ORGANISM: Zea mays

<400> SEQUENCE: 39

Pro Ala Pro His Gly Gly Arg Gly Ala Leu Pro Ser Ala Gly Gly Ser
1               5                   10                  15

Pro Ser Asp Leu Leu Phe Leu Ala Gly Gly
            20                  25

<210> SEQ ID NO 40
<211> LENGTH: 28
<212> TYPE: PRT
<213> ORGANISM: Selaginella moellendorffii

<400> SEQUENCE: 40

Ser Leu Ser Cys His Gly Gly Arg Gly Ala Ser Pro Ser Glu Gly Gly
1               5                   10                  15

His Pro Ser Asp Leu Thr Phe Leu Ala Gly Gly Gly
            20                  25

<210> SEQ ID NO 41
<211> LENGTH: 180
<212> TYPE: DNA
<213> ORGANISM: Actinidia eriantha
```

<400> SEQUENCE: 41
acggctatac tcggagtttc tcggccgctc atacatgtcc ggtctgtacg acgcaagggt    60
tgtgtagtcg agagcaaccc ttcgccgcac ggaggacgtg gcgccttgcc gtccgaaggc    120
ggtagcccct ccgacctcct cttcctcgcc ggcggcggtc acttcgcttt ctccgtctac    180

<210> SEQ ID NO 42
<211> LENGTH: 186
<212> TYPE: DNA
<213> ORGANISM: Cucumis sativus

<400> SEQUENCE: 42
acggctatac acgtagtttc ccggtcgttc tttcatgtca gggctgtacg acggaagggt    60
tgtataactc cgacaaaccc ttcgccgcac ggcggacgtg gtgctttgcc ttccgaaggt    120
ggtagtcctt ctgatcttct ttttctcgcc ggcggtggtt tctcttgctt cttctcttct    180
tcgtat                                                                186

<210> SEQ ID NO 43
<211> LENGTH: 174
<212> TYPE: DNA
<213> ORGANISM: Glycine max

<400> SEQUENCE: 43
acggctattc taagagtgtc tcgctctctc attcatgtcc caactgtacg acggaggaca    60
ggttgcgtaa ctgccaccaa cccttcgccg cacggtgggc gtggtgcttt gccttctgaa    120
ggtggtagcc cttcagactt gctcttctta gctggtggtg ttctgctgt cttc           174

<210> SEQ ID NO 44
<211> LENGTH: 183
<212> TYPE: DNA
<213> ORGANISM: Solanum lycopersicum

<400> SEQUENCE: 44
acggctatac acaaagtaaa ccgccgacca cttttacatg ttccagcagt acgtcgtaag    60
ggttgtgtaa cagctactaa ccctgcgccg cacggtggac gtggcgcttt gccttctgaa    120
ggtggtagtc cttccgacct cctcttcctt gccggcggcg gttctttcct ctccttctcc    180
tac                                                                   183

<210> SEQ ID NO 45
<211> LENGTH: 177
<212> TYPE: DNA
<213> ORGANISM: Vitis vinifera

<400> SEQUENCE: 45
acggctatac aaagaattcc gccgcctctc atacatgtcc gggcggtacg acgcaagggy    60
tgtgtaattg agagcaaccc ttcgccgcac ggcgggcgtg gcgctttgcc ttcagaaggc    120
ggtagtccct ctgatctgct cttcctcgcc ggcggtggtt ccaacgcttt cctctgc       177

<210> SEQ ID NO 46
<211> LENGTH: 192
<212> TYPE: DNA
<213> ORGANISM: Arabidopsis thaliana

<400> SEQUENCE: 46
acggctatac acgggatatc acggggtgtt agctcacatg tccatattgt ccgacagaag    60
ggttgtttaa tcgaaactaa tcctttgccg cacggaggac gtggagctct gccgtctgaa    120

```
ggcggcagcc cttccgatct cctctttctc gccggtggcg gttccagctt taacttcttt    180
tcctttaggt tt                                                        192

<210> SEQ ID NO 47
<211> LENGTH: 183
<212> TYPE: DNA
<213> ORGANISM: Arabidopsis thaliana

<400> SEQUENCE: 47
acggcttttc ttagagttta tcggtcactt tcacatgccc gaactgtacg acgtaagggt    60
tgttgcttaa ctccgactaa cccttcgccg cacggtgggc gtggtgctct gccttctgaa   120
ggtggtagcc cctccgatct tctcttcctc gccggtggtg gtgtctttgc tccttcttcc   180
ttc                                                                  183

<210> SEQ ID NO 48
<211> LENGTH: 192
<212> TYPE: DNA
<213> ORGANISM: Malus x domesticus

<400> SEQUENCE: 48
acggctatac ccagagctcc tcggccgctc gttcatgtcc ggggtgtcgg acgaaagggt    60
tgtgtaattg agagcaaccc ttcgccgcac ggcgggcgtg gtgctttgcc ttccgaaggc   120
ggtagcccgt ctgacctcct cttcctcgcc ggtggcggct cccttcctc tgttttctc    180 ttctgctttt at                                                        192

<210> SEQ ID NO 49
<211> LENGTH: 183
<212> TYPE: DNA
<213> ORGANISM: Medicago truncatula

<400> SEQUENCE: 49
acggcttttc ttagagttta tcggtcactt tcacatgccc gaactgtacg acgtaagggt    60
tgttgcttaa ctccgactaa cccttcgccg cacggtgggc gtggtgctct gccttctgaa   120
ggtggtagcc cctccgatct tctcttcctc gccggtggtg gtgtctttgc tccttcttcc   180
ttc                                                                  183

<210> SEQ ID NO 50
<211> LENGTH: 189
<212> TYPE: DNA
<213> ORGANISM: Populus trichocarpa

<400> SEQUENCE: 50
acggctatac acgagtaac tcggtcccta attcatgtcc gggctgttcg acgtaagggc     60
tgtgtaatag agagcagcaa cccttcgccg cacggtggac gtggtgcttt accctcggaa   120
ggcggtagcc cttctgatct cctctttcta gctggtggcg gtttcttctt cttctgttta   180
gtagtagtt                                                            189

<210> SEQ ID NO 51
<211> LENGTH: 240
<212> TYPE: DNA
<213> ORGANISM: Picea sitchensis

<400> SEQUENCE: 51
acggctatta aacgtatttt gcggttccag ccccatgatc gcagaagaat tctgcggagc    60
```
aggaacgctg gttgtgcact agagagtacc ccgtcgccgc acggtgggag aggagccttg    120
ccctcggaag gcgggagccc ctctgatctc ctctttctcg caggaggcgg ttgcgaccga    180 gccctttct gcctcgccca tccatttctt ctgagcagag gagaaataat ttgggagagg    240

<210> SEQ ID NO 52
<211> LENGTH: 171
<212> TYPE: DNA
<213> ORGANISM: Physcomitrella patens

<400> SEQUENCE: 52
atgagcaaag acttctaccg tgcaggaatc caactgtccc gatctctctc ttcctctctt     60
tccttgcacg gtggtcgggg ggccgccccc agtgaaggcg gtcgtccctc tgacctatct    120
gcacttgctg ggggaggttt tctctcaaac tttcaccacg gtgctgatcc t             171

<210> SEQ ID NO 53
<211> LENGTH: 180
<212> TYPE: DNA
<213> ORGANISM: Actinidia arguta

<400> SEQUENCE: 53
acggctatac tcggagtttc tcggccgctc atacatgtcc ggtctgtacg acgcaagggt     60
tgtgtagtcg agagcaaccc ttcgccgcac ggcggacgtg gcgccttgcc gtccgaaggc    120
ggtagcccct ccgacctcct cttcctcgcc ggtggcggtc acttcgcttt ctccgtctac    180

<210> SEQ ID NO 54
<211> LENGTH: 180
<212> TYPE: DNA
<213> ORGANISM: Actinidia eriantha

<400> SEQUENCE: 54
acggctatac tcggagtttc tcggccgctc atacatgtcc ggtctgtacg acgcaagggt     60
tgtgtagtcg agagcaaccc ttcgccgcac ggaggacgtg gcgccttgcc gtccgaaggc    120
ggtagcccct ccgacctcct cttcctcgcc ggcggcggtc acttcgcttt ctccgtctac    180

<210> SEQ ID NO 55
<211> LENGTH: 180
<212> TYPE: DNA
<213> ORGANISM: Actinidia chinensis

<400> SEQUENCE: 55
acggctatac tcggagtttc tcggccgctc atacatgtcc ggtctgtacg acgcaagggt     60
tgtgtagtcg agagcaaccc ttcgccgcac ggcggacgtg gcgccttgcc gtccgaaggc    120
ggtagcccct ccgacctcct cttcctcgcc ggcggcggtc acttcgcttt ctccgtctac    180

<210> SEQ ID NO 56
<211> LENGTH: 192
<212> TYPE: DNA
<213> ORGANISM: Fragaria vulgaris

<400> SEQUENCE: 56
acggctatac acagagtttc acggccactc attcatgtcc gccggactgt ccgacgtaag     60
ggttgtgtaa ttgagagcaa cccttcgccg cacggcgggc gtggtgcttt gccgtccgaa    120
ggaggaagtc cttccgacct ccttttcctc gccggcggtg gtgtccacgt ttccgacttg    180
cgtttctttt tc                                                        192

<210> SEQ ID NO 57
<211> LENGTH: 183
<212> TYPE: DNA
<213> ORGANISM: Solanum tuberosum

<400> SEQUENCE: 57

```
acggctatac acaaagtaaa ccgccgacca cttttacatg ttccagcagt acgtcgtaag      60
ggttgtgtaa cagctactaa ccctgcgccg cacggtggac gtggcgcttt gccctctgaa     120
ggtggcagtc cttccgacct cctcttcctt gccggcggcg gttctttcct ctccttctcc     180
tac                                                                   183
```

<210> SEQ ID NO 58
<211> LENGTH: 165
<212> TYPE: DNA
<213> ORGANISM: Chlamydomonas reinhardtii

<400> SEQUENCE: 58

```
atgcatttgc gtgagccggt aaaaacggcg ttctctgagg cagcccgcgt tcagtcggct      60
gcgtcgcagc ctgcgaccgc caatcggtgc tccggtggcc gtggtgcagc cccctcgtgc     120
ggtggcaagc caaggacgc tctgagcaag gcgggcggtg ccag                       165
```

<210> SEQ ID NO 59
<211> LENGTH: 174
<212> TYPE: DNA
<213> ORGANISM: Zea mays

<400> SEQUENCE: 59

```
acggctagcg ttgcagcccc ccggcgcggc ccgcagctg cgcaggtgga gcccacgggc       60
accatcgcct ccgctgtcgc gtccagcccc gctccgcacg gcggccgcgg ggcgctgccc     120
tcggccggag gaagcccgtc cgatctcctc ttcctcgccg gcggsgktcg cctc            174
```

<210> SEQ ID NO 60
<211> LENGTH: 183
<212> TYPE: DNA
<213> ORGANISM: Selaginella moellendorffii

<400> SEQUENCE: 60

```
acggcttcaa ttgagctttt gagtcgacac cccatcattt gttatggaca cagtgtttcc      60
agttgtaaga ctctgctgag ttccctctct tgccacggtg gtcgagggc tagcccctcg      120
gaaggaggac acccttcaga tcttaccttt cttgctggtg gtggccttct tctcggagca     180
cca                                                                   183
```

<210> SEQ ID NO 61
<211> LENGTH: 105
<212> TYPE: DNA
<213> ORGANISM: Actinidia eriantha

<400> SEQUENCE: 61

```
aagggttgtg tagtcgagag caaccccttcg ccgcacggag gacgtggcgc cttgccgtcc     60
gaaggcggta gccctccga cctcctcttc ctcgccggcg gcggt                      105
```

<210> SEQ ID NO 62
<211> LENGTH: 105
<212> TYPE: DNA
<213> ORGANISM: Cucumis sativus

<400> SEQUENCE: 62
```

```
aagggttgta taactccgac aaacccttcg ccgcacggcg gacgtggtgc tttgccttcc    60
gaaggtggta gtccttctga tcttcttttt ctcgccggcg gtggt                  105
```

<210> SEQ ID NO 63
<211> LENGTH: 108
<212> TYPE: DNA
<213> ORGANISM: Glycine max

<400> SEQUENCE: 63

```
aggacaggtt gcgtaactgc caccaaccct tcgccgcacg gtgggcgtgg tgctttgcct    60
tctgaaggtg gtagcccttc agacttgctc ttcttagctg gtggtggt              108
```

<210> SEQ ID NO 64
<211> LENGTH: 105
<212> TYPE: DNA
<213> ORGANISM: Solanum lycopersicum

<400> SEQUENCE: 64

```
aagggttgtg taacagctac taaccctgcg ccgcacggtg gacgtggcgc tttgccttct    60
gaaggtggta gtccttccga cctcctcttc cttgccggcg gcggt                  105
```

<210> SEQ ID NO 65
<211> LENGTH: 105
<212> TYPE: DNA
<213> ORGANISM: Vitis vinifera

<400> SEQUENCE: 65

```
aagggytgtg taattgagag caacccttcg ccgcacggcg ggcgtggcgc tttgccttca    60
gaaggcggta gtccctctga tctgctcttc ctcgccggcg gtggt                  105
```

<210> SEQ ID NO 66
<211> LENGTH: 105
<212> TYPE: DNA
<213> ORGANISM: Arabidopsis thaliana

<400> SEQUENCE: 66

```
aagggttgtt taatcgaaac taatccttg ccgcacggag gacgtggagc tctgccgtct    60
gaaggcggca gcccttccga tctcctcttt ctcgccggtg gcggt                  105
```

<210> SEQ ID NO 67
<211> LENGTH: 105
<212> TYPE: DNA
<213> ORGANISM: Arabidopsis thaliana

<400> SEQUENCE: 67

```
aagggttgtt taatcataac taatccttg cctcacggag gacgtggagc tctgccgtct    60
gaaggcggca gtccctccga tctcctcttc ctcgccggag gcggt                  105
```

<210> SEQ ID NO 68
<211> LENGTH: 105
<212> TYPE: DNA
<213> ORGANISM: Malus x domesticus

<400> SEQUENCE: 68

```
aagggttgtg taattgagag caacccttcg ccgcacggcg ggcgtggtgc tttgccttcc    60
gaaggcggta gcccgtctga cctcctcttc ctcgccggtg gcggc                  105
```

<210> SEQ ID NO 69
<211> LENGTH: 107

```
<212> TYPE: DNA
<213> ORGANISM: Medicago truncatula

<400> SEQUENCE: 69
aagggttgtt gcttaactcc gactaaccct tcgccgcacg gtgggcgtgg tgctctgcct    60
tctgaaggtg gtagcccctc cgatcttctc ttcctcgccg gtggtgg                 107

<210> SEQ ID NO 70
<211> LENGTH: 108
<212> TYPE: DNA
<213> ORGANISM: Populus trichocarpa

<400> SEQUENCE: 70
aagggctgtg taatagagag cagcaaccct tcgccgcacg gtggacgtgg tgctttaccc    60
tcggaaggcg gtagcccttc tgatctcctc tttctagctg gtggcggt                108

<210> SEQ ID NO 71
<211> LENGTH: 102
<212> TYPE: DNA
<213> ORGANISM: Picea sitchensis

<400> SEQUENCE: 71
ggttgtgcac tagagagtac cccgtcgccg cacggtggga gaggagcctt gccctcggaa    60
ggcgggagcc cctctgatct cctctttctc gcaggaggcg gt                      102

<210> SEQ ID NO 72
<211> LENGTH: 78
<212> TYPE: DNA
<213> ORGANISM: Physcomitrella patens

<400> SEQUENCE: 72
tccttgcacg gtggtcgggg ggccgccccc agtgaaggcg gtcgtccctc tgacctatct    60
gcacttgctg ggggaggt                                                 78

<210> SEQ ID NO 73
<211> LENGTH: 105
<212> TYPE: DNA
<213> ORGANISM: Actinidia arguta

<400> SEQUENCE: 73
aagggttgtg tagtcgagag caaccttcg ccgcacggcg gacgtggcgc cttgccgtcc     60
gaaggcggta gccctccga cctcctcttc ctcgccggtg gcggt                    105

<210> SEQ ID NO 74
<211> LENGTH: 105
<212> TYPE: DNA
<213> ORGANISM: Actinidia eriantha

<400> SEQUENCE: 74
aagggttgtg tagtcgagag caaccttcg ccgcacggag gacgtggcgc cttgccgtcc     60
gaaggcggta gccctccga cctcctcttc ctcgccggcg gcggt                    105

<210> SEQ ID NO 75
<211> LENGTH: 105
<212> TYPE: DNA
<213> ORGANISM: Actinidia chinensis

<400> SEQUENCE: 75
aagggttgtg tagtcgagag caaccttcg ccgcacggcg gacgtggcgc cttgccgtcc     60
```

```
gaaggcggta gccctccga cctcctcttc ctcgccggcg gcggt                    105

<210> SEQ ID NO 76
<211> LENGTH: 105
<212> TYPE: DNA
<213> ORGANISM: Fragaria vulgaris

<400> SEQUENCE: 76
aagggttgtg taattgagag caacccttcg ccgcacggcg ggcgtggtgc tttgccgtcc    60
gaaggaggaa gtccttccga cctccttttc ctcgccggcg gtggt                   105

<210> SEQ ID NO 77
<211> LENGTH: 105
<212> TYPE: DNA
<213> ORGANISM: Solanum tuberosum

<400> SEQUENCE: 77
aagggttgtg taacagctac taaccctgcg ccgcacggtg gacgtggcgc tttgccctct    60
gaaggtggca gtccttccga cctcctcttc cttgccggcg gcggt                   105

<210> SEQ ID NO 78
<211> LENGTH: 69
<212> TYPE: DNA
<213> ORGANISM: Chlamydomonas reinhardtii

<400> SEQUENCE: 78
ggtggccgtg gtgcagcccc ctcgtgcggt ggcaagccca aggacgctct gagcaaggcg    60
ggcggtggc                                                           69

<210> SEQ ID NO 79
<211> LENGTH: 81
<212> TYPE: DNA
<213> ORGANISM: Zea mays

<400> SEQUENCE: 79
cccgctccgc acggcggccg cggggcgctg ccctcggccg gaggaagccc gtccgatctc    60
ctcttcctcg ccggcggsgk t                                             81

<210> SEQ ID NO 80
<211> LENGTH: 72
<212> TYPE: DNA
<213> ORGANISM: Selaginella moellendorffii

<400> SEQUENCE: 80
cacggtggtc gaggggctag cccctcggaa ggaggacacc cttcagatct tacctttctt    60
gctggtggtg gc                                                       72

<210> SEQ ID NO 81
<211> LENGTH: 655
<212> TYPE: DNA
<213> ORGANISM: Actinidia eriantha
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t
```

<400> SEQUENCE: 81

| tctctccgtc | cctctcaata | gttgtctcca | ttcgcagtaa | aatcactaag | gccgctcgtc | 60 |
| cctcagtgca | caccacggcc | cctccacagc | cgcattcacc | tctctctctc | tctctctgct | 120 |
| ctatctatat | atcccccaa | tctggcctct | cttcacctca | cccccaaaat | ctacacaaaa | 180 |
| tcaatccttc | atcttccaca | tcggcctcca | aaacccacnc | tcttctccac | aatccagaca | 240 |
| caccttgagc | ggctggcgtt | gagcgaatag | atagagatag | agagagagat | tttctgcttc | 300 |
| gatcggggt | aaaacccggt | gtttgacaag | ttgtagacat | cacggctata | ctcggnagtt | 360 |
| tctncggccg | ctcatacatg | tccggtctgt | acgacgcaag | ggttgtgtag | tcgagagcaa | 420 |
| cccttcgccg | cacggcggac | gtggcgcctt | gccgtccgaa | ggcggtagcc | cctccgacct | 480 |
| cctcttcctc | gccggcggcg | gtcacttcgc | tttctccgtc | tactagctta | ttaggtttat | 540 |
| tcttacttag | tgagtaattc | gtcctattat | agttcgtaag | ttcatcaaag | atctgttact | 600 |
| tgattcgtct | ttcgttgctc | gagtcttggt | gttttttgcg | ttttctgagt | tcgag | 655 |

<210> SEQ ID NO 82
<211> LENGTH: 600
<212> TYPE: DNA
<213> ORGANISM: Cucumis sativus

<400> SEQUENCE: 82

| tccctttcta | tataattgct | tcattcccca | cctttccatg | ttcgtgcagc | ccattcaatc | 60 |
| ccctcatttt | aacccacttc | ctcttttttct | ttttctcctt | cctctccag | ttcccttttc | 120 |
| cccatctggg | ttctcttgat | ttctcttaaa | atccaacaac | ccatgttcga | ctttgaggaa | 180 |
| ttggtgcgtt | ggaattgagt | tttcggagaa | gattttttcgt | tttttatcac | aacccatcta | 240 |
| ctccaggtaa | ggggtaaaac | ccgggttcgt | caggctgtag | acatcacggc | tatacacgta | 300 |
| gtttcccggt | cgttctttca | tgtcagggct | gtacgacgga | agggttgtat | aactccgaca | 360 |
| aaccctcgc | cgcacggcgg | acgtggtgct | ttgccttccg | aaggtggtag | tccttctgat | 420 |
| cttcttttttc | tcgccggcgg | tggtttctct | tgcttcttct | cttcttcgta | ttagctttcc | 480 |
| gtttgtgttt | tagctctacc | ggtttaggat | ttgacatcag | caagtttctg | tttcgcgttt | 540 |
| atttctttttg | ggtggggag | attttggtgt | tcggtttggt | ttgaattaga | agcagacgat | 600 |

<210> SEQ ID NO 83
<211> LENGTH: 429
<212> TYPE: DNA
<213> ORGANISM: Glycine max

<400> SEQUENCE: 83

| gacaaactca | caccacatcc | atctttgcct | tctgcatgtt | ggttctctgt | aaacagatac | 60 |
| tgcaaaagaa | gaataatatt | gaatatttgg | ttggggttgaa | tccctgggtt | gaagcgttgc | 120 |
| agacatcacg | gctattctaa | gagtgtctcg | ctctctcatt | catgtcccaa | ctgtacgacg | 180 |
| gaggacaggt | tgcgtaactg | ccaccaaccc | ttcgccgcac | ggtgggcgtg | gtgctttgcc | 240 |
| ttctgaaggt | ggtagcccctt | cagacttgct | cttcttagct | ggtggtggtt | ctgctgtctt | 300 |
| ctagcttctt | cttaactctt | ttttcttttt | actacttttta | agctaccttg | ttttcaaaat | 360 |
| aacaaaaaca | aacactttct | tacttcataa | gatcacctttt | tcttcatctt | ctacttctcc | 420 |
| ttcactaaa | | | | | | 429 |

<210> SEQ ID NO 84

<211> LENGTH: 680
<212> TYPE: DNA
<213> ORGANISM: Solanum lycopersicum

<400> SEQUENCE: 84

```
atttgttcgg tatactgtaa cccctgtttt gcgattggcc ttgtagcccc gttttacatc      60
ttccagagac tccatttgta tcggttcaca tacagtagca aagcgccatt atcttactct     120
accccattgg caaacccaca gccacaattt tccaatcctc cattatccct tctacaattt     180
tctatataaa tacccacatc tctctgctct actcccttat tatcaacaac aaccaccaaa     240
tttcttcttt tttttcttcg atagtagcaa tctatcaaca aaaacagaga ccccatcaca     300
agaatcttgg aattttagtg ttgggtttaa gaggaaaagg ggttattgta ttttgcagtt     360
ttgagggtaa agcccagttt aacaagttgt agacatcacg ctatacaca aagtaaaccg      420
ccgaccactt ttacatgttc cagcagtacg tcgtaagggt tgtgtaacag ctactaaccc     480
tgcgccgcac ggtggacgtg gcgctttgcc ttctgaaggt ggtagtcctt ccgacctcct     540
cttccttgcc ggcggcggtt cttttcctctc cttctcctac tagatatagt tatacttact    600
atagatctct agcttattac gtacagttgt atctagtatt ctattgatta ttcgaagaaa     660
acacacaaaa agaagtaaag                                                  680
```

<210> SEQ ID NO 85
<211> LENGTH: 600
<212> TYPE: DNA
<213> ORGANISM: Vitis vinifera

<400> SEQUENCE: 85

```
acacaaaagc ctctcaagtc caacagatag gccgccttct tcctcatttc actgcagcta      60
gcttcctatt tttcttcttc caaaatccag ggatttcaag agaagagaaa gagaaataag     120
ggttctgcgg gttgtgggtc ggtgtgtttt gtggttttct atatagggtt tctaaggagg     180
gagggatttt gatttgggtt gtgacggtgg tggggtaaaa cccttgttcg acgagttgta     240
gacatcacgg ctatacaaag aattccgccg cctctcatac atgtccgggc ggtacgacgc     300
aagggytgtg taattgagag caaccctccg ccgcacggcg ggcgtggcgc tttgccttca     360
gaaggcggta gtccctctga tctgctcttc ctcgccggcg gtggttccaa cgctttcctc     420
tgctagttta ggcttatatt ctgcataata tagctactgt ctttaggatt agatcaacca     480
atccgtatcg aacactcgat ctctcgcttt agccatttct ttagatcaat caatccgtat     540
cgaacaatcg atctctcgct ttagccattt ctttaggttg gtgtttgagt tcttgaaaaa     600
```

<210> SEQ ID NO 86
<211> LENGTH: 503
<212> TYPE: DNA
<213> ORGANISM: Arabidopsis thaliana

<400> SEQUENCE: 86

```
gtatcatcaa aaacaccctc aaagaattat tcattcaggc atcttctcaa attttgttt      60
gtgaaaaaaa cccacatcaa aagatctctc atttattcgt ttcgtttctg ctgttttgag    120
tgtcgggttc gttttagctg taatctttttt tccggcgtt cgatttgaaa aaatccgggg    180
aacaggtgat cggaatcacg gctatacacg ggatatcacg gggtgttagc tcacatgtcc     240
atattgtccg acagaagggt tgtttaatcg aaactaatcc tttgccgcac ggaggacgtg     300
gagctctgcc gtctgaaggc ggcagccctt ccgatctcct ctttctcgcc ggtggcggtt     360
ccagctttaa cttcttttcc tttaggtttt aggagttagg gtttgttagt gttttttcct     420
```

```
tcttcttttt ttggtgctct tgaatcgctt ttttcttggg ggaagttttt tcttttgctc      480
ttcgaaattt gtcttttttg aga                                              503

<210> SEQ ID NO 87
<211> LENGTH: 420
<212> TYPE: DNA
<213> ORGANISM: Arabidopsis thaliana

<400> SEQUENCE: 87
caaaatctca cacatcaaac acgtgaattt gctctctttc tggttcactc acctaccatt       60
actataagtc tgaaagagtg attgaaaccc acctcgaaaa atctatcctt tttttttgttt     120 tccttctccg gcgaatcccc ggggagattg gtaatcggta atcacggcta tttacgggat      180
aaagccacgg cctttgagct ttcatgtcca acgaaagggt tgtttaatca taactaatcc      240
tttgcctcac ggaggacgtg gagctctgcc gtctgaaggc ggcagtccct ccgatctcct      300
cttcctcgcc ggaggcggtt ccacaaatag ccactaaccc taacccttttt tctaattagg     360 tttttagttc ttagagtcct gtattaatct gttatttcga gattataata tttgtgagca      420

<210> SEQ ID NO 88
<211> LENGTH: 554
<212> TYPE: DNA
<213> ORGANISM: Malus x domesticus

<400> SEQUENCE: 88
ccccacctgc tccccccaatt ccccagtacc catttgtgtt tttcgattca gttcgaaacc      60
aggcggtctt cacctttctg gttgttttcc tatctcggtt ttaaggagga agaagaaagg     120
aaggcgtttt gatcattttc ttttcgaatt tcttttgggg taagacccag gttcgacgag      180
ttgtagacat cacggctata cccagagctc ctcggccgct cgttcatgtc cggggtgtcg      240
gacgaaaggg ttgtgtaatt gagagcaacc cttcgccgca cggcgggcgt ggtgctttgc      300
cttccgaagg cggtagcccg tctgacctcc tcttcctcgc cggtggcggc tccccttcct     360 ctgttttttct cttctgcttt tattagtttt atttttatag agtttcttgc ttagattttt     420
agagattttt tgttctataa agcgctcgag tagatcgtat ttttgttttc ggggttttt      480 ttttttttgtg gtgtttgatt tttactgaga aatcgagaaa aaagggaga gagagagaga      540 gaaagaaggc gagt                                                        554

<210> SEQ ID NO 89
<211> LENGTH: 600
<212> TYPE: DNA
<213> ORGANISM: Medicago truncatula

<400> SEQUENCE: 89
aacaaaacac cctcctcgtg cttgattcta gtacaagtat accaaactca ttcacaacca       60
catttcctta atctcttttc attttctctt atctatataa cacttacaa tctccacctc      120 attttcttca tcaaaaacaa ttcatctttc ttctttgcta tcatcactaa attttcttga     180
gaattcagaa aataaaagag agatttgaat gtttgggttg attccctgta ttgacacgtt      240
gtagacatca cggcttttct tagagtttat cggtcacttt cacatgcccg aactgtacga      300
cgtaagggtt gttgcttaac tccgactaac ccttcgccgc acggtgggcg tggtgctctg      360 cccttctgaag gtggtagccc ctccgatctt ctcttcctcg ccggtggtgg tgtctttgct     420
ccttcttcct tctaatttct tgttttttagt ttaactttct ttagattttt acgactcaaa    480
```

```
actataagct aaaactagac tttgtaagta agatttattt gaaggtgctt cttcttcttc    540
ttctttcttc ttcttgttgt taaaaaaaaa agtattttg tgtttggttt ggtgaaaatg    600
```

<210> SEQ ID NO 90
<211> LENGTH: 621
<212> TYPE: DNA
<213> ORGANISM: Populus trichocarpa

<400> SEQUENCE: 90

```
gaaccattag tgtgtaccct cctcaccaaa aagaataaaa actctcaca accaaacccc     60 aattcacagc aaaaccataa ccacaattcc cacttctctc ttatctatac aatatcccat   120 ctccttttc ttcttttatc tcttgctctc atcaaaatcc cagcacctct cctctcgctg   180
ctaataaact tcaactccca tttctgcggc ggcggctgca gcccagtggt tcttgttttt   240
tctttattta ttgtgatctg taaaaaaaaa tctaaagagt acaagaacaa gggttaaaat   300
cccagggtag acaagttgta gacatcacgg ctatacacgg agtaactcgg tccctaattc   360
atgtccgggc tgttcgacgt aagggctgtg taatagagag cagcaaccct tcgccgcacg   420
gtggacgtgg tgctttaccc tcggaaggcg gtagcccttc tgatctcctc tttctagctg   480
gtggcggttt cttcttcttc tgtttagtag tagtttagtg ctattgttgt tgttaattat   540
tattattatt attattaaat ctaaataaa aggccagtct gcaaataagt aaaagtatta   600
gatctcgaat aagcgaacaa g                                             621
```

<210> SEQ ID NO 91
<211> LENGTH: 640
<212> TYPE: DNA
<213> ORGANISM: Picea sitchensis

<400> SEQUENCE: 91

```
cggtgaagaa gtggtgagaa gtgggttgt ggttaacgtt tgttcagccg tcctctgata     60
tctcttcagc cttacacgta ttttctggta taaacgtatt gtcatctgaa tctgaattta   120
ttagctgcgt cttttatgagg ttcgaaagcg ggatctcctc agcttcagag tttactttct  180
ggacggaaag aaatctgtat tcatagtttg tgaaggcagg gaggggattc gatccggtgc   240
agttgtggag gaaattcgga gggtaacatc acggggactg gtgtcgggag acgaaaataa   300
ggccattcaa gaagggaaag aaaggtctgg caagttgggg caacacggct attaaacgta   360
ttttgcggtt ccagccccat gatcgcagaa gaattctgcg gagcaggaac gctggttgtg   420
cactagagag tacccgtcg ccgcacggtg ggagaggagc cttgccctcg gaaggcggga   480
gcccctctga tctcctcttt ctcgcaggag gcggttgcga ccgagccctt ttctgcctcg    540
cccatccatt tcttctgagc agaggagaaa taatttggga gaggtagagg tggtttagcc   600
taatttaggc gtcaatcaat cgctcatatt aaccaccacc                         640
```

<210> SEQ ID NO 92
<211> LENGTH: 253
<212> TYPE: DNA
<213> ORGANISM: Physcomitrella patens

<400> SEQUENCE: 92

```
cgcgtccata tgagcaaaga cttctaccgt gcaggaatcc aactgtcccg atctctctct     60
tcctctcttt ccttgcacgg tggtcggggg gccgccccca gtgaaggcgg tcgtccctct   120
gacctatctg cacttgctgg gggaggtttt ctctcaaact ttcaccacgg tgctgatcct   180
tagggggggg tgctagggag aattttctgc tcaggtaaca ggaagtgtct aggagactat   240
```
tcaacctgca aaa                                                            253

<210> SEQ ID NO 93
<211> LENGTH: 477
<212> TYPE: DNA
<213> ORGANISM: Actinidia arguta

<400> SEQUENCE: 93
gcaaaatcaa cccttcatct tccacatcgg cctcccaaac ccacctcttc tccacaatcc          60
aggcacacct tgagcggctg gcgttgaggg aatagagaga gagagagaga gagattttct        120
gcttcgatcg ggggtaaaac ccggtgtttg acaagttgta gacatcacgg ctatactcgg        180
agtttctcgg ccgctcatac atgtccggtc tgtacgacgc aagggttgtg tagtcgagag        240
caacccttcg ccgcacggcg gacgtggcgc cttgccgtcc gaaggcggta gcccctccga        300
cctcctcttc ctcgccggtg gcggtcactt cgctttctcc gtctactagc ttattaggtt        360
tattcttact tagtgagtaa tttgtcctat tatagttcgt aagttcgtcg aagatctgtt        420
gcttgattcg tctttcgttg ctcgagtctt ggtgttttttg cgttttctga gttcgag          477

<210> SEQ ID NO 94
<211> LENGTH: 655
<212> TYPE: DNA
<213> ORGANISM: Actinidia eriantha
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (356)..(356)
<223> OTHER INFORMATION: n is a, c, g, or t
<220> FEATURE:
<221> NAME/KEY: misc_feature
<222> LOCATION: (364)..(364)
<223> OTHER INFORMATION: n is a, c, g, or t

<400> SEQUENCE: 94
tctctccgtc cctctcaata gttgtctcca ttcgcagtaa aatcactaag gccgctcgtc          60
cctcagtgca caccacggcc cctccacagc cgcattcacc tctctctctc tctctctgct        120
ctatctatat atccccccaa tctggcctct cttcacctca ccccaaaat ctacacaaaa         180 tcaatccttc atcttccaca tcggcctcca aaacccacnc tcttctccac aatccagaca        240
caccttgagc ggctggcgtt gagcgaatag atagagatag agagagagat tttctgcttc        300 gatcggggt aaaacccggt gtttgacaag ttgtagacat cacggctata ctcggnagtt         360
tctncggccg ctcatacatg tccggtctgt acgacgcaag ggttgtgtag tcgagagcaa        420
cccttcgccg cacggcggac gtggcgcctt gccgtccgaa ggcggtagcc cctccgacct        480
cctcttcctc gccggcggcg gtcacttcgc tttctccgtc tactagctta ttaggtttat        540
tcttacttag tgagtaattc gtcctattat agttcgtaag ttcatcaaag atctgttact        600
tgattcgtct ttcgttgctc gagtcttggt gttttttgcg ttttctgagt tcgag             655

<210> SEQ ID NO 95
<211> LENGTH: 473
<212> TYPE: DNA
<213> ORGANISM: Actinidia chinensis

<400> SEQUENCE: 95
cacaaaatca atccttcatc ttccacatcg gcctccaaaa cccacctctt ctccacaatc          60

| | |
|---|---|
| cagacacacc ttgagctgct ggcgttgagc gaatagatag agagagagat tttctgcttc | 120 |
| gatcggggt aaaacccggt gtttgacaag ttgtagacat cacggctata ctcggagttt | 180 |
| ctcggccgct catacatgtc cggtctgtac gacgcaaggg ttgtgtagtc gagagcaacc | 240 |
| cttgccgca cggcggacgt ggcgccttgc cgtccgaagg cggtagcccc tccgacctcc | 300 |
| tcttcctcgc cggcggcggt cacttcgctt tctccgtcta ctagcttatt aggtttattc | 360 |
| ttacttagtg agtaattcgt cctattatag ttcgtaagtt catcaaagat ctgttacttg | 420 |
| attcgtcttt cgttgctcga gtcttggtgt tttttgcgtt ttctgagttc gag | 473 |

<210> SEQ ID NO 96
<211> LENGTH: 444
<212> TYPE: DNA
<213> ORGANISM: Fragaria vulgaris

<400> SEQUENCE: 96

| | |
|---|---|
| aatacaccac cacataacca aaacccactg ccccatttc tcgattctca ttcgcatctg | 60 |
| actaggaagg agagattttc tgcgttgggt ttgattccgg tttggggtaa aacccgggtc | 120 |
| gacgagttgt agacatcacg gctatacaca gagtttcacg ccactcatt catgtccgcc | 180 |
| ggactgtccg acgtaagggt tgtgtaattg agagcaaccc ttcgccgcac ggcgggcgtg | 240 |
| gtgctttgcc gtccgaagga ggaagtcctt ccgacctcct tttcctcgcc ggcggtggtg | 300 |
| tccacgtttc cgacttgcgt ttcttttct agctttttgt agattcgggt ttagctcaaa | 360 |
| gattattgtt tcgcaagtag atcgtgtttg ctgtcgttgc tgtgctttga ttttcttt | 420 |
| gagaagaaca agaacataac aaaa | 444 |

<210> SEQ ID NO 97
<211> LENGTH: 600
<212> TYPE: DNA
<213> ORGANISM: Solanum tuberosum

<400> SEQUENCE: 97

| | |
|---|---|
| ccatttgtat cggttcacac acagtaagca agcgccatta tccatctcta cccccattgg | 60 |
| caaacccaca gccacaattt tcctatcctc cattatccct tctccaattt attatataaa | 120 |
| tacccacatc tccctgctct ttctccctta tcatcaacaa caacaaccaa atttcttctt | 180 |
| tttttcttcc acagtagcaa tctatcaaca aaacagagac cccattacaa gaatcttgga | 240 |
| attttagttt tgggtttaag aggaagggt tattgtattt gcagttttga gggtaaagcc | 300 |
| cagtttaaca aggtgtagac atcacggcta tacacaaagt aaaccgccga ccacttttac | 360 |
| atgttccagc agtacgtcgt aagggttgtg taacagctac taaccctgcg ccgcacggtg | 420 |
| gacgtggcgc tttgccctct gaaggtggca gtccttccga cctcctcttc cttgccggcg | 480 |
| gcggttcttt cctctccttc tcctactaga tatagttata cttaccgtag atctctagct | 540 |
| tattacgtac agttctatct agtattctct tgattattcg aagaaaaca caaaaagatg | 600 |

<210> SEQ ID NO 98
<211> LENGTH: 499
<212> TYPE: DNA
<213> ORGANISM: Chlamydomonas reinhardtii

<400> SEQUENCE: 98

| | |
|---|---|
| cagcttccaa actttgtctg tattatctgc cacgcttgct cgagctgcat tacctgagag | 60 |
| tgcgacaaag cgacctcgcg taaattgaat ggcttgtgcg gctactttct cccaacttct | 120 |
| tcatgcattt gcgtgagccg gtaaaaacgg cgttctctga ggcagcccgc gttcagtcgg | 180 |

| | |
|---|---|
| ctgcgtcgca gcctgcgacc gccaatcggt gctccggtgg ccgtggtgca gcccctcgt | 240 |
| gcggtggcaa gcccaaggac gctctgagca aggcgggcgg tggccagtaa ccttcctcgc | 300 |
| gcaacacacc gcgcgagcgc ctgcggctgt tggacagcca gcagcgtgtg tcgacccgc | 360 |
| gccaggacac cggcagcgac gtcgacggct agtatcatct agcctttagc aactctagcc | 420 |
| tagaaactta gtattcgctc acgaaacttt taggagcttt tcgtcgatca acatcgcctc | 480 |
| gctcgtcgcc gcggacaca | 499 |

<210> SEQ ID NO 99
<211> LENGTH: 480
<212> TYPE: DNA
<213> ORGANISM: Zea mays

<400> SEQUENCE: 99

| | |
|---|---|
| aaaccaaacc cagctcaggc acaaccccaa cgcaccgccg ccgctcgcct ggcctcacct | 60 |
| cgccggagaa gagttataag acaggagaac cccgtccccg gggcgcaggc ctcggcagct | 120 |
| tccgtgacca ccgcccaatc ctgccacagc tgccctccct cctccctct gggcgtggcc | 180 |
| gagttgtagg catcacggct agcgttgcag cccccggcg cggccccgca gctgcgcagg | 240 |
| tggagcccac gggcaccatc gcctccgctg tcgcgtccag ccccgctccg cacggcggcc | 300 |
| gcggggcgct gccctcggcc ggaggaagcc cgtccgatct cctcttcctc gccggcggsg | 360 |
| ktcgcctctg agccgttcct gtctctcacc ttcttccttt cctagcaatt agtcccttct | 420 |
| gctaaccccc ccggaccccg acgagttctc accccgagag taactgaccg acctaccggc | 480 |

<210> SEQ ID NO 100
<211> LENGTH: 337
<212> TYPE: DNA
<213> ORGANISM: Selaginella moellendorffii

<400> SEQUENCE: 100

| | |
|---|---|
| gcttttgatt caggtatggt tgctccccaa ttcagcacat ttcctttctt tttccttgca | 60 |
| gggtttattc ttatgcactg actagcctgg aagaaggcta gtccgtgcca aaattttgac | 120 |
| aaccacggct tcaattgagc ttttgagtcg acacccatc atttgttatg acacagtgt | 180 |
| ttccagttgt aagactctgc tgagttccct ctcttgccac ggtggtcgag gggctagccc | 240 |
| ctcggaagga ggacaccctt cagatcttac ctttcttgct ggtggtggcc ttcttctcgg | 300 |
| agcaccatag tggggtttc aatcttattg gctaaag | 337 |

<210> SEQ ID NO 101
<211> LENGTH: 2130
<212> TYPE: DNA
<213> ORGANISM: Actinidia eriantha
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1750)..(1750)
<223> OTHER INFORMATION: n is a, c, g, or t
<220> FEATURE:
<221> NAME/KEY: misc_feature
<222> LOCATION: (1754)..(1755)
<223> OTHER INFORMATION: n is a, c, g, or t

<400> SEQUENCE: 101

```
atcccaaaat atttgttcac ttagaaaatt aactgataaa ataatgcaaa ctctcctttt      60
tgttctcctc ttttgaattg acgtgacaca tttatctttt aattttaga taatttcgaa     120
ttattgaaaa aaaattaaac tgttttccaa ataataattt tttagaaata atgcaaataa     180
tagttttta aactatttc caaatatttt ttttcaaaaa taatgcatta ttaagaataa      240
tattaaaaaa tatcttcaaa tattaaaaaa tatattttg ataaaattta ataatatata     300
aaaataaatg aatgtttttg tttgcataaa caatttctaa taaaatattt tgcgaaaatg     360
ttttgtttg cataaacaat ttctaataaa atattttgcg aaaatgtttt tgttcgcata     420
aacaatttct gataaaattt tttgcaaaac taaacctaac acaaatgggt agcattttg     480
cttctttaaa atcttggatt ccctaaatta gacaaataaa ttgggacgga tcaacattta     540
ttttcttctt aattwntttc tctaacacta caacaaaata attaaataga taagaaaaga     600
gaaaaaggaa cttgagaacc cacccaactt ttaaacattg cagttgggtc cttccgtacg     660
ttgcagtggt cctccacaac gtccacatga accacatggg cgtggttaat acaacgcacc     720
ccactctctc tctctctctc tctctctcga taattgtctc cattcgcagt aaaattacca     780
aggccactcg tcccacagtg cacaccacgg ccgatccaca gccacactca ccaatcacct     840
ctctctctct ctctctctct agaatttatt tgttgctctt ggagcaacac gtcacttttt     900
gacacgtggt ggtcggatcc aatcatctca cgccatccaa gcactcagtt tcatgtgttt     960
gccacgtcac cacaacaatt ccaccacaaa cccaggtaaa cacaagacta acagaacctc    1020
actccgttaa tgccatcttc ctgtcgctga ctcgcatgaa ataccaccac ttttggaaac    1080
caaacgccag aaaagattac tctcaccaat attctctatg aacaaagaaa ttgggttatt    1140
atttattatt tacaagaaat aaatggcacc aaccaaattt aaaagacgt tctctgcagcg    1200
atttcacct cattttatt tttgagcttt taggtgtctc gtccgaaacc gacgccttct    1260
ntattatgca attttcact cttctttgcc ttctcagtcc cgaaatgact attttcaggc    1320
aacatcatag ggtgattggg ttgtttagct atgtaggtac gaaatctaaa aatttgaatt    1380
tgtaaagttt atgaatattt catcgcatcg agtactggcg gaatgttcac ggggttaaca    1440
ggatttgaac tccgttattt cttttcttgag taaacggacg tggctgaata cacggacaac    1500
caattaaatg gtgtatgata tttcgtgtgg agcaccacgc gtagaaagtg aggtgttgcg    1560
tcaagagcat caaataattt ctcctctctc tctctccctc ttctctatct atatatcccc    1620
caatctggcc tctcctcacc tcaccccaa agtctacaca gaatcaaccc ttcatctccc    1680
gcataggcct cccaaaccca cctcttctcc acaatccaga cacacctcga gtggccggag    1740
tttagagagn aganngagag agagatttc tgcttcgatc gggggtaaa acccggtgtt    1800
tgacaagttg tagacatcac ggctataatc ggagtttctc ggccgctcat acatgtccgg    1860
tctgtacgac gcaagggttg tgtagtcgag agcaacccctt cgccgcacgg cggacgtggc    1920
gccttgccgt ccgaaggcgg tagcccctcc gacctcctct cctcgccgg cggcggtcac    1980
ttcgctttct ccgtctacta gcttattagg tttattctta cttagtgagt aattcgtcct    2040
attatagttc gtaagttcat caaagatctg ttacttgatt cgtctttcgt tgctcgagtc    2100
ttggtgtttt ttgcgttttc tgagttcgag                                    2130
```

<210> SEQ ID NO 102
<211> LENGTH: 1959
<212> TYPE: DNA
<213> ORGANISM: Arabidopsis thaliana

<400> SEQUENCE: 102

```
ttttgatact tgtcctctcg aaattgatgt ttactgacgc acgattattg ggaatttggg    60
acttagtggt gtaccaatag catctcagct ttcatggtta caaagaggcc agtgaaagag   120
gcttggtcaa ccgcaattat gatccgttac ttgcactgac taccaccgat ccaccgccgt   180
aactctttaa atcttaatgc aatactaatt cgaattacat gtcgaggtct aaaacatga    240
taaatggttg tttaaagtaa aaaagaaaa gaaacaataa ataaaacaaa cggtgatgga   300
aggagggacg tacgatcgta gtcgtagaga ctgccaaata aataatggac cactatatg    360
tggttcaaga actatatcct tttcttagat tccgaatctt aacttgtgtt tcttgccttg   420
tttggttttt tttttgttta ttttgtagtt ttgtctcata aaataacgaa caaaaagcaa   480
tggtctaaat atttctcaat atatgtattt aaaaattata tcatagtttc gcaaaaaaac   540
gaccgaacga acgatggtag tcatttgccc aaattgagcc tcgtagtagt tgctacgacc   600
acaccccgt cccatgaata aacacgacca tgtaaatatt atctataaag acaacataaa    660
tttacaaatt aatgttgaac agaaaaagtc aaaagaaaa tttcgttaat ataataataa   720
tattctatga taatataaaaa cgtggcataa cacatgactt cacatgacat cataagaaga  780
catatgccac atgaactctt catcgcctcc atccttttag tctcgtttac atgcagcaaa   840
ctacgatcta cgattatata caatgaaatt caaattcata atcaattggc attaaacata   900
cgtatatcat aattcataag gttaactagg tttagcaaat gttattctct ttggataaac   960
gtttagcaat tgtttatctc aaatttaatt gaaatactt gtaagacaca gttacaatta    1020
gttctcaatt ccaatctac acaagattta aatctttctt tagttcattc tgatctattt   1080
ttctctcaaa gaaatgtag tgctccaact tttctcccaa gactaataaa aatttttctta  1140
attgcatgca aaaatatttt ttccaacttt aatcttatca aacttagatc tcattttatc   1200
ttccgaataa gattttttgtt ttggtccttt gcctaatcaa actaactaat tagattagaa  1260
gaaaaataca attagacaaa ataatatcga tgaaaaaata aaatccacaa gaaaggacct   1320
aagaaattc acgtccgaat cacaaccaca gaaaaaaaga gagaaatatt agtatataat   1380
taaaattttg tcgtctgtct tctctggttc actcatctcc tatctattta aagcccattc  1440
gatatcctaa aacactgtat catcaaaaaa cacctcaaag aattattcat tcaggcatct   1500
tctcaaattt ttgtttgtga aaaaaaccca catcaaaaga tctctcattt attcgtttcg   1560
tttctgctgt tttgagtgtc gggttcgttt tagctgtaat ctttttttcc ggcgttcgat   1620
ttgaaaaaat ccggggaaca ggtgatcgga atcacggcta tacacgggat atcacggggt   1680
gttagctcac atgtccatat tgtccgacag aagggttgtt taatcgaaac taatcctttg   1740
ccgcacggag gacgtggagc tctgccgtct gaaggcggca gcccttccga tctcctcttt   1800
ctcgccggtg gcggttccag ctttaacttc ttttccttta ggttttagga gttagggttt   1860
gttagtgttt tttccttctt ctttttttgg tgctcttgaa tcgctttttt cttgggggaa   1920
gttttttctt ttgctcttcg aaatttgtct tttttgaga                          1959
```

<210> SEQ ID NO 103
<211> LENGTH: 1161
<212> TYPE: DNA
<213> ORGANISM: Arabidopsis thaliana

<400> SEQUENCE: 103

```
acgcgtgatg aatcaatcat tcattcacgc caacgtaaaa aaaaaaaaa aaaaaaatt    60
```

```
taactaaaat tatacggatg atttatttac atggacgctg attaaaaaag gtcggtccaa    120
ttaattattt acttaataat taattaaagt gttgtgtgta ttttttggatt cccataatgt   180
tttgaggggt atataaagga gattatttt tctatttttca atgtctacga ataaaatgga   240
acatcctcgt tccaatatat actgctgttt tattactaag gtttataatt ggagtgtata   300
aaaacactcc aaaataatat catgaataat gtttttatac gtataataca taaaataaaa   360
tctctttcct catagctggt cctctgatta ctatcaaaca tatgattcaa ttgcaaattt   420
gcaattatta atgcaagaag aatgagtgga acattaaagt tagatcaaaa actcttcatt   480
acaaacataa ataaattcat tttggtgctt tctaaattaa tttattgatc attttttggt   540
atgtagctag gggttaactc atcaggaaga acattaccta gatgatgtca ttgtcaaagt   600
caataggttg acttatccga tggatactaa tccaacgggt caaaaagtgc caaatcgggt   660
caaaatcaaa aacctcaaag atgacccgtg aacacttgtt tttatcttcc tcacaaaatc   720
cacacgtcca aatcacaacc tcaaaatctc acacatcaaa cacgtgaatt tgctctcttt   780
ctggttcact cacctaccat tactataagt ctgaaagagt gattgaaacc cacctcgaaa   840
aatctatcct tttttttgtt ttccttctcc ggcgaatccc cggggagatt ggtaatcggt   900
aatcacggct atttacggga taaagccacg gcctttgagc tttcatgtcc aacgaaaggg   960
ttgtttaatc ataactaatc ctttgcctca cggaggacgt ggagctctgc cgtctgaagg  1020
cggcagtccc tccgatctcc tcttcctcgc cggaggcggt tccacaaata gccactaacc  1080
ctaacccttt ttctaattag gttttttagtt cttagagtcc tgtattaatc tgttatttcg  1140
agattataat atttgtgagc a                                             1161

<210> SEQ ID NO 104
<211> LENGTH: 2003
<212> TYPE: DNA
<213> ORGANISM: Malus x domesticus

<400> SEQUENCE: 104
gacgagatca gcacgatgtt ggaggagtta gaggcctgac agaaaaaaaa aayattaaaa    60
caggcgtcta acgtcagatc caccccaggc tctcgggccg gcgagaatcg acgggcctgg   120
ggctcggggt tgctcaggct cccttgccag ccaacgctgg acttcctacc tcgggcaacc   180
aagctcgggg ttgttcaaca tctttctctc tctccctctt tcacatattc ccatcaattt   240
tttctctctt ctttcacctc acccatccaa aactacaata ttcggtttta tttttttat   300
ggaaaataaa tttaktaaag agaaaatcat ctcgaacaac atgttccaac tccmaattca   360
attaaagttc aaagcatcta actccgaagc awggaggcaa taattctaaa agtggggatt   420
ggacaccaac accccaacgt aagcaagctt atcaaccaca aaattgattt tattatgttt   480
ccagaagaag tcgattgcaa cacttggaaa ataaaccaac agctacggaa aatcaaaaca   540
aacacaacag aatttctata taaaaatgct tgtacacatt gccatacccct aattttcacc   600
atgttatgaa attttcaatc tgaattttag caattgtaaa tttccgaaat cttgaacaat   660
tttcttcatt tcaacaaaag agaaatgttg taaacgggaa ttgacatatt tttaatccga   720
taaacycttt ctctktctca attaattcaa gagaactta acgaaaaact ytcgttactg    780
ttcayttaa taaaaaatca cattttaaa ctaaaaagtc aatcmtkgta ctatwcactt    840
tacccttat tttgtcctta tcattaaaac ttttcragtt ttttcatta gtttcytttt    900
aattcaaarc sgtttaagta ttatatattt caaccctcat tttcttgcat ataaagtcaa   960
gtcttttttc cctcsatccg tacacaaagt ggtccatata cggcaatcat aagtaccagt  1020
```

```
gaacctcaat ctctcacaca ttttttttct caattattgt cccaaaaaag gacccggctt    1080
ttcttcgttc tcactttcta tacactttca actcttctta atttatttat gcarttacgs    1140
ttaagttatg ttaatatttt atattaattt ttttttataa arataataaa acaaaaaaya    1200
ataataatat aaaatattaa trtaayttaa ccgtaatygc ayaaataaaa aaaataasaa    1260
tgtattaaar rtgggaggac aaagaagtca ggtccctaga aaatacacca tcaaaccaac    1320
caaggccacg aaaccccca aaatacaaac aaaccccca cggcacatcc tctaccacaa    1380
atccactttt cctccccatg cctataaatc caccccctca tctcctctcc acaccccac    1440 aaccacaaac cccacctgct cccccaattc cccagtaccc atttgtgttt ttcgattcag    1500
ttcgaaacca ggcggtcttc acctttctgg ttgttttcct atctgggttt taaggaggaa    1560
gaagaaagga aggcgttttg atcattttct tttcgaattt cttttggggt aagacccagg    1620
ttcgacgagt tgtagacatc acggctatac ccagagctcc tcggccgctc gttcatgtcc    1680
ggggtgtcgg acgaaagggw tgtgtaattg agagcaaccc ttcgccgcac ggcgggcgtg    1740
gtgctttgcc ttccgaaggc ggtagcccgt ctgacctcct cttcctcgcc ggtggcggct    1800
ccccttcctc tgttttctc ttctgctttt attagtttta tttttataga gtttcttgct    1860 tagatttta gagatttttt gttctataaa gcgctcgagt agatcgtatt tttgttttcg    1920 ggggttttt tttttgtgg tgtttgattt ttactgagaa atcgagaaaa aaagrgagag    1980
agagagagag agagaaagaa ggc                                             2003

<210> SEQ ID NO 105
<211> LENGTH: 2000
<212> TYPE: DNA
<213> ORGANISM: Malus x domesticus

<400> SEQUENCE: 105
tgcccttctc aataacaata acatagaatg atactttgca kaactcaaay agactagggc      60
tcatctggac trcttttaaa atgattaaaa sygttttktkg tgaaaatatt ttaatatcaa    120
tcyttagtaa aaattcaagt ggaycctcaa aaacayttgg agtgcttcct ataagaatca    180
tattggtgct tcttccaaca aacaattgaa gtgcttttg aactcaaaat tcatttcacc      240
aaaaacactt tcaaatatta ctatgcttcc tcttttgtag ttaagttcaa atcatctatc    300
gctatgtcca aaaacaaaac attaaaaaaa tgtgagatca tattaaaaaa aagaaaattg    360
gaactttgtc ttcttgaact aaaatatcat gagtactctt gaacttgtca aatatagaac    420
aatggccatc tagataactt gttaggactt acataactta tttgctccctt taattcttta    480 ttttttatga aagttctaac tgtrttatct aaagaggtta ttgctccaca ttacgacaag    540 ctcaaaaat tcatcaaaat taattaggta taaaatctct tattgttggt tacatgttca    600
atttactaaa cttcagcgtt ggataccaat atatatgtgt ttaggtacaa gctttagaaa    660
caaggataat gcagccatst agtgaaactg gcatgaagac cccatgtttt tatggtcacc    720
gcccacaccc atgtgagcaa gacatggaca atggataagg tgattgtcct tggatattmt    780
ggggcatgtc ccttaatttt aaggacgacg actgctacta gtctactacc accacttttt    840
gctttgcata gtactttggg ccctgtgcgt ccttgaatgt yctggtgcat ttactataac    900
tttaaggacg acgacttaga ctactattta tttattttaa ttaactgtta ttaagagaaa    960
aagatgggag ttcgaactat tacaaaaaat aaaagagmgg gtttagaatt cataatgcat   1020
agataaaaat ttaacattct attcattaag atattgaact acatgcacta ctaatacttc   1080
```

| | |
|---|---|
| tttagttggg ragttgcagg caaaacaact cgtgcatgtg aacacattgt gatttggttt | 1140 |
| tctctcgagt acaacacact atcattttgg ttttctctag agttttagcg agttgtcatg | 1200 |
| aaattagttt ttattttat ttgttattca acgacatrgt tacaccaagt gtagatgcat | 1260 |
| aatttgggaa aaccayataa taagctaact ataacaattt aatatcaaat gcrtcatcta | 1320 |
| tgaagttgag ccttgagctc ctacttatgt acaaatgaaa atgaataccg tartactaaa | 1380 |
| tgactaactt agacatcaag aaattgataa aataaaawtt aaaaaaaaaa actacaagca | 1440 |
| tgatgatgag gaatgaggat cctatctgaa tcctctttat gaggactcta aagattctcc | 1500 |
| aatcacgtcc gtttattata gatcgtacga cttgttttg ttagatgtta tttatattca | 1560 |
| atttaaaaaa aattacaata atatataatc acatgatata caataaaata gatataatta | 1620 |
| aaagattcct ataattaaag aatcctcaca aagagatttc cgaacgctct ttcgaccatg | 1680 |
| agggtagtta ggctcctaaa tacttgaaag gtacagtaca tcatcatggt aggtttgaag | 1740 |
| ttataagtcc acctcatcca aaacacagca tatagaatga ttccctcatg gatcccgaat | 1800 |
| cctaaatttt tatttcaatt aaaatttgtg tgcttgcttt gtggaatgcg gaccgtcttc | 1860 |
| ttgtaaattt cgtaggaaga ctcggctcca atttttttawg attaaaatcc gctgccatgg | 1920 |
| tcaattcact gtcgtctaat tatcaacagg cagccttcca acccacgtgt ttgtttgcac | 1980 |
| gcattagaat attcactgtc | 2000 |

<210> SEQ ID NO 106
<211> LENGTH: 2018
<212> TYPE: DNA
<213> ORGANISM: Malus x domesticus

<400> SEQUENCE: 106

| | |
|---|---|
| ccgaggacct cagaagcgag ggggcaatgt ttgggcccaa aataacagtt tgggccgagt | 60 |
| gtagggtcat tctcggcccg gaaggcctta cgacaagaat actatggatc gttcagtacg | 120 |
| tgggcatcca aacctaggtc agctaggtca taacgcaaga ggtcgaatcc tagtgcaata | 180 |
| aggagtctcg gcaggacccg gaagtgaatc cggctcagtt agggactagg ttcacagtcc | 240 |
| tagtgaaggt aggactggtc gagttgatgc tgatcagggg aagaaaacct agtccgagta | 300 |
| ggttttttaac tcgaccttgg ggggagccat tgctataaat agaaaaggtt gcacatcctt | 360 |
| caatgacccc tgcaaatcaa tacaaaattg ccctgcgcaa attctcacaa cttgtgattt | 420 |
| ttctttttcc tttttttcgct gacacatctt ccgttggcat caacagcact gtggaagcaa | 480 |
| ccggtgatat cttaagtcgg catagatagc tctgtcaccg tagagttagt cggtctcgca | 540 |
| gtatcttccg ttggcatcaa cagcactgcg gcgagaaygg ttgattacct atccaagtct | 600 |
| cggtcragaa gggtttctaa atccttattg gtcgaggtca tctcatcagc cttctcggcg | 660 |
| ragtgaggtg ttacagttat tacattcggc acattgaaag ccgaatttga tattgaactt | 720 |
| cktaagaata gtaaccttgt cttcaggttc gagagcccaa gaggycgaga cgtgttcctt | 780 |
| tctcggccgc aatcgcaaga cgcagaagtc agtagcgcga cccaacgcaa catcaayaaa | 840 |
| tttactcmtc ggccgagctc ggcckacgag ttggcacgcc ccgcattcac cgaaggacgt | 900 |
| agttagctca ttaattactc ggcctgcgcg ccacgtaggc tttgtagttt ctagggtcaa | 960 |
| caaggtgaaa ttcttgaatt tatgaaagac aaacaattac aaaaatgttt gctaatgatg | 1020 |
| ttttcattaa ttaagaatga aaattggaaa tccgaagatg atcacatacc aatgggcttt | 1080 |
| gtgatgtcat ttatgtttta gaccgatgcc cctctcgaat gaggatcctc tctggatcct | 1140 |
| ctctgtgaga atcatctccg gatcctcttt ttaagaatct cgagaattct caaatcgtgt | 1200 |

```
tcgtttatcg tacatcatgc gatcaagttt cttcagttat tgttcatgtt taattttaaa    1260
taaaaatatt taaaatgatt tttgatcgaa caatgtacga taaaagaaca cgatttaaga    1320
attttcagaa ttatagtaaa gaatatccga agaggatcct cattcgcccc ctctataccc    1380
aaaaaaccaa taaatagatc cgaccgaata tccaaaatcc aaaaacagtt gcgtaatatc    1440
tttacacatg aacggttggg atcggtcaaa ggacggaaaa ccagaacaca cgtgtccgtc    1500
tccgttcgtc ccagtagcag accgtagacc ggaactctgt atcgcgaaat caaaagacgt    1560
cacgatatag aagaagaaga gaaagagaaa cggagataga tatttgatac agattttccg    1620
atcgcacaat catcgacatt ctcgaccaat ttgaagactc ggaatcgctg gtccggcgag    1680
ggctggcttc gtagatgcaa tcacggctct aatcaaagca atcactagta ttaagatttc    1740
gagaggcagc agagaatgca tgagagcctt ccctaattcc ctgcttgcat gcccttcgtt    1800
tcacggcggt cgcggtgccc taccctccgc cggtgggcat ccatccgatc tcacctacct    1860
ggccggcggc ggttgcttct gaaaacgacg accgcctgtg tttccccttc tgggttttga    1920
gtgtacttcg ttttttatta agcagtaatc aatggttacg gttaagcagc ttcaagatgg    1980
taactttacg tcgcaattcc ctccattttc tctgcaag                           2018

<210> SEQ ID NO 107
<211> LENGTH: 2000
<212> TYPE: DNA
<213> ORGANISM: Actinidia chinensis

<400> SEQUENCE: 107
ttggtgtata agatgagta aatagggatc ccggcaaatg gtctccacaa aagtgtagtg      60
tcttaggggc actatagaga ttccaaatct ccctagatat tttgttccac agtatatgat     120
ccacaatgag ccatgtattt tatataattt tatttatttt tttataatta ctcataggtt     180
atgtttgaat gctagtaatc acaaggagaa tagcaatatg atttcaaatc tttggaattt     240
taccatttgg ataaagtagg aataagaata taatatttat tgatatttta aattagattc     300
ataaagtaac gaggaatctg attctgcaaa gatcctaatt aatttcaaat ttctccgtca     360
tttttttata aatttgataa caaatataaa tccttttta aaatattatt tcgtgattaa     420
gattctgaac aaaggcaagt acttgaataa gattaactct ttcattaaat tattaaaaat     480
tatattatta ataacgaaaa cgatcatcca aacacagcat aggggaatgg atatattccg     540
tggtatcaat gaaatttgca aatgtgcgtg agaacccaac tttattcatg gtgaaaataa     600
gcgaatagga agggcaaatt tcgccaatgg tctctgtagt ttaacaaaag tttcactttg     660
gttcttataa ttttaatata aacaattaaa attttgaact tttaattta ttttatata     720 gttgttctat ctataatcgt taagaatttg aatggaaagt gagaacatag agctcacgta     780 ggccctttt agaggataat tttactacta ttttttgctta taatttggtt aaaattttac     840
tttagtcctt ataaataatc acgagttttc acatgctttt tctccattta tgttattaat     900
ttttattgac agagggaagc tacattgaaa tccaattgaa actttagaga tataactgtc     960
caaattgaaa ataaggaac taagtgaac ttttaatcaa attacaaaga caagatgaaa    1020
ttttcccgaa taacaactta gcacattggc atattcgtcg ctctcttgtg tatagacaac    1080
actgccctca actattcact gttactacaa aattgccaca cattcaagct aaagcatcaa    1140
cccactatga tactatgatg ctgcaacaca gccttgaata ttaggtattt attgtagttg    1200
agtttatatt taaattgaat ttttattaaa aattaaatat ttaaaaatag aagttaaaaa    1260
```

| | |
|---|---|
| atattaaaat aaactttttt aaaatttaac ttttaattt tttagaagtt atttatagtc | 1320 |
| cataagtaga aaaactataa taaacacaga ctttaaggca aaataaatca aaagtttcta | 1380 |
| ctaataagta acaacaaaac atgggtgttt gatagagtga acttacacta taattgccaa | 1440 |
| tttaaaaata aaatttaaaa aattttaaaa taaagatttt aagaatcagc tattttttcaa | 1500 |
| ctttcgtagt ttgttttggc ccataagtag aagtagacgc aaaaactgtg ctaaacactt | 1560 |
| tggcgcaact tttaagacaa aaatggctat aagttgtatg ccaaacatgc aatattcgct | 1620 |
| ctaaaattgc caagtatgtc accattggtc attccgatta aacccagggg tacttttgtc | 1680 |
| tttaaatttc tataatttat gtacttttc attttttttt tgcttttttgt tataattata | 1740 |
| aattaatgat gtccactctg ttcttccatg taccacctga aagatcaaga agcaagatat | 1800 |
| atatattgtt attctaccat tctctctctc tctctctctc tctcatcaga caattctctt | 1860 |
| tcaaaaaaca aaggaatggc caaaaacggt acggccccat taatctctct tctgtgtgtg | 1920 |
| tgtgtgtgtg tgtgtgtgtg taaatgtgta tattgtgtac aatgtatttg ttatctgtgt | 1980 |
| ttcgatggat ttgttgtgtg | 2000 |

<210> SEQ ID NO 108
<211> LENGTH: 28
<212> TYPE: PRT
<213> ORGANISM: Artificial Sequence
<220> FEATURE:
<223> OTHER INFORMATION: Construct

<400> SEQUENCE: 108

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 109
<211> LENGTH: 20
<212> TYPE: PRT
<213> ORGANISM: Artificial Sequence
<220> FEATURE:
<223> OTHER INFORMATION: Primer

<400> SEQUENCE: 109

Thr Ala Thr Cys Cys Gly Cys Thr Gly Gly Ala Ala Gly Ala Thr Gly
1               5                   10                  15

Gly Ala Ala Cys
            20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
tccacctcga tatgtgcatc     20

<210> SEQ ID NO 111
<211> LENGTH: 246
<212> TYPE: DNA
<213> ORGANISM: Cucumis sativus

<400> SEQUENCE: 111
gggtaaaacc cgggttcgtc aggctgtaga catcacggct atacacgtag tttcccggtc     60

```
gttctttcat gtcagggctg tacgacggaa gggttgtata actccgacaa acccttcgcc    120
gcacggcgga cgtggtgctt tgccttccga aggtggtagt ccttctgatc ttcttttct    180 cgccggcggt ggtttctctt gcttcttctc ttcttcgtat tagctttccg tttgtgtttt    240
agctct                                                               246
```

\<210\> SEQ ID NO 112
\<211\> LENGTH: 254
\<212\> TYPE: DNA
\<213\> ORGANISM: Actinidia eriantha

\<400\> SEQUENCE: 112

```
gggtaaaacc cggtgtttga caagttgtag acatcacggc tataatcgga gtttctcggc     60
cgctcataca tgtccggtct gtacgacgca agggttgtgt agtcgagagc aacccttcgc    120
cgcacggcgg acgtggcgcc ttgccgtccg aaggcggtag cccctccgac ctcctcttcc    180
tcgccggcgg cggtcacttc gctttctccg tctactagct tattaggttt attcttactt    240
agtgagtaat tcgt                                                      254
```

\<210\> SEQ ID NO 113
\<211\> LENGTH: 253
\<212\> TYPE: DNA
\<213\> ORGANISM: Actinidia arguta

\<400\> SEQUENCE: 113

```
ggtaaaaccc ggtgtttgac aagttgtaga catcacggct atactcggag tttctcggcc     60
gctcatacat gtccggtctg tacgacgcaa gggttgtgta gtcgagagca acccttcgcc    120
gcacggcgga cgtggcgcct tgccgtccga aggcggtagc ccctccgacc tcctcttcct    180
cgccggtggc ggtcacttcg ctttctccgt ctactagctt attaggttta ttcttactta    240
gtgagtaatt tgt                                                       253
```

\<210\> SEQ ID NO 114
\<211\> LENGTH: 255
\<212\> TYPE: DNA
\<213\> ORGANISM: Actinidia eriantha
\<220\> FEATURE:
\<221\> NAME/KEY: misc_feature
\<222\> LOCATION: (49)..(49)
\<223\> OTHER INFORMATION: n is a, c, g, or t
\<220\> FEATURE:
\<221\> NAME/KEY: misc_feature
\<222\> LOCATION: (57)..(57)
\<223\> OTHER INFORMATION: n is a, c, g, or t

\<400\> SEQUENCE: 114

```
ggtaaaaccc ggtgtttgac aagttgtaga catcacggct atactcggna gtttctncgg     60
ccgctcatac atgtccggtc tgtacgacgc aagggttgtg tagtcgagag caacccttcg    120
ccgcacggcg gacgtggcgc cttgccgtcc gaaggcggta gccccctccga cctcctcttc    180 ctcgccggcg gcggtcactt cgctttctcc gtctactagc ttattaggtt tattcttact    240
tagtgagtaa ttcgt                                                     255
```

\<210\> SEQ ID NO 115
\<211\> LENGTH: 253
\<212\> TYPE: DNA
\<213\> ORGANISM: Actinidia chinensis

\<400\> SEQUENCE: 115

```
ggtaaaaccc ggtgtttgac aagttgtaga catcacggct atactcggag tttctcggcc      60
gctcatacat gtccggtctg tacgacgcaa gggttgtgta gtcgagagca acccttcgcc     120
gcacggcgga cgtggcgcct tgccgtccga aggcggtagc ccctccgacc tcctcttcct     180
cgccggcggc ggtcacttcg ctttctccgt ctactagctt attaggttta ttcttactta     240
gtgagtaatt cgt                                                        253

<210> SEQ ID NO 116
<211> LENGTH: 254
<212> TYPE: DNA
<213> ORGANISM: Malus x domesticus

<400> SEQUENCE: 116
ggtaagaccc aggttcgacg agttgtagac atcacggcta tacccagagc tcctcggccg      60
ctcgttcatg tccggggtgt cggacgaaag ggttgtgtaa ttgagagcaa cccttcgccg     120
cacggcgggc gtggtgcttt gccttccgaa ggcggtagcc cgtctgacct cctcttcctc     180
gccggtggcg gctccccttc ctctgttttt ctcttctgct tttattagtt ttattttat     240 agagtttctt gctt                                                       254

<210> SEQ ID NO 117
<211> LENGTH: 247
<212> TYPE: DNA
<213> ORGANISM: Fragaria vulgaris

<400> SEQUENCE: 117
ggtaaaaccc gggtcgacga gttgtagaca tcacggctat acacagagtt tcacggccac      60
tcattcatgt ccgccggact gtccgacgta agggttgtgt aattgagagc aacccttcgc     120
cgcacggcgg cgtggtgct tgccgtccg aaggaggaag tccttccgac ctccttttcc     180
tcgccggcgg tggtgtccac gtttccgact tgcgtttctt tttctagctt tttgtagatt     240
cgggttt                                                               247

<210> SEQ ID NO 118
<211> LENGTH: 256
<212> TYPE: DNA
<213> ORGANISM: Arabidopsis thaliana

<400> SEQUENCE: 118
tgaaaaaatc cggggaacag gtgatcggaa tcacggctat acacgggata tcacggggtg      60
ttagctcaca tgtccatatt gtccgacaga agggttgttt aatcgaaact aatcctttgc     120
cgcacggagg acgtggagct ctgccgtctg aaggcggcag cccttccgat ctcctctttc     180
tcgccggtgg cggttccagc tttaacttct tttcctttag gttttaggag ttagggtttg     240
ttagtgtttt ttcctt                                                     256

<210> SEQ ID NO 119
<211> LENGTH: 245
<212> TYPE: DNA
<213> ORGANISM: Arabidopsis thaliana

<400> SEQUENCE: 119
aatccccggg gagattggta atcggtaatc acggctattt acgggataaa gccacggcct      60
ttgagctttc atgtccaacg aaagggttgt ttaatcataa ctaatccttt gcctcacgga     120
ggacgtggag ctctgccgtc tgaaggcggc agtccctccg atctcctctt cctgccgga     180 ggcggttcca caaatagcca ctaaccctaa ccctttttct aattaggttt ttagttctta     240
```

```
gagtc                                                                      245

<210> SEQ ID NO 120
<211> LENGTH: 256
<212> TYPE: DNA
<213> ORGANISM: Populus trichocarpa

<400> SEQUENCE: 120
ggttaaaatc ccagggtaga caagttgtag acatcacggc tatacacgga gtaactcggt         60
ccctaattca tgtccgggct gttcgacgta agggctgtgt aatagagagc agcaacccct        120
cgccgcacgg tggacgtggt gctttaccct cggaaggcgg tagcccttct gatctcctct        180
ttctagctgg tggcggtttc ttcttcttct gtttagtagt agtttagtgc tattgttgtt        240
gttaattatt attatt                                                         256

<210> SEQ ID NO 121
<211> LENGTH: 252
<212> TYPE: DNA
<213> ORGANISM: Glycine max

<400> SEQUENCE: 121
ggttgaatcc ctgggttgaa gcgttgcaga catcacggct attctaagag tgtctcgctc         60
tctcattcat gtcccaactg tacgacggag gacaggttgc gtaactgcca ccaacccttc        120
gccgcacggt gggcgtggtg cttgccttc tgaaggtggt agcccttcag acttgctctt        180
cttagctggt ggtggttctg ctgtcttcta gcttcttctt aactcttttt tcttttact        240 acttttaagc ta                                                             252

<210> SEQ ID NO 122
<211> LENGTH: 253
<212> TYPE: DNA
<213> ORGANISM: Medicago truncatula

<400> SEQUENCE: 122
ggttgattcc ctgtattgac acgttgtaga catcacggct tttcttagag tttatcggtc         60
actttcacat gcccgaactg tacgacgtaa gggttgttgc ttaactccga ctaacccttc        120
gccgcacggt gggcgtggtg ctctgccttc tgaaggtggt agcccctccg atcttctctt        180
cctcgccggt ggtggtgtct tgctccttc ttccttctaa tttcttgttt ttagtttaac         240
tttctttaga ttt                                                            253

<210> SEQ ID NO 123
<211> LENGTH: 252
<212> TYPE: DNA
<213> ORGANISM: Solanum lycopersicum

<400> SEQUENCE: 123
gggtaaagcc cagtttaaca agttgtagac atcacggcta tacacaaagt aaaccgccga         60
ccacttttac atgttccagc agtacgtcgt aagggttgtg taacagctac taaccctgcg        120
ccgcacggtg gacgtggcgc tttgccttct gaaggtggta gtccttccga cctcctcttc        180
cttgccggcg gcggttcttt cctctccctt cctactagaa tatagttata cttactatag        240
atctctagct ta                                                             252

<210> SEQ ID NO 124
<211> LENGTH: 252
<212> TYPE: DNA
```

<213> ORGANISM: Solanum tuberosum

<400> SEQUENCE: 124

| | | | | | |
|---|---|---|---|---|---|
| gggtaaagcc | cagtttaaca | aggtgtagac | atcacggcta | tacacaaagt | aaaccgccga | 60 |
| ccactttac | atgttccagc | agtacgtcgt | aagggttgtg | taacagctac | taaccctgcg | 120 |
| ccgcacggtg | gacgtggcgc | tttgccctct | gaaggtggca | gtccttccga | cctcctcttc | 180 |
| cttgccggcg | gcggttcttt | cctctccttc | tcctactaga | tatagttata | cttaccgtag | 240 |
| atctctagct | ta | | | | | 252 |

<210> SEQ ID NO 125
<211> LENGTH: 258
<212> TYPE: DNA
<213> ORGANISM: Vitis vinifera

<400> SEQUENCE: 125

| | | | | | |
|---|---|---|---|---|---|
| gggtaaaacc | cttgttcgac | gagttgtaga | catcacggct | atacaaagaa | ttccgccgcc | 60 |
| tctcatacat | gtccgggcgg | tacgacgcaa | gggytgtgta | attgagagca | acccttcgcc | 120 |
| gcacggcggg | cgtggcgctt | tgccttcaga | aggcggtagt | ccctctgatc | tgctcttcct | 180 |
| cgccggcggt | ggttccaacg | ctttcctctg | ctagtttagg | cttatattct | gcataatata | 240 |
| gctactgtct | ttaggatt | | | | | 258 |

<210> SEQ ID NO 126
<211> LENGTH: 682
<212> TYPE: DNA
<213> ORGANISM: Solanum lycopersicum

<400> SEQUENCE: 126

| | | | | | |
|---|---|---|---|---|---|
| atttgttcgg | tatactgtaa | cccctgtttt | gcgattggcc | ttgtagcccc | gttttacatc | 60 |
| ttccagagac | tccatttgta | tcggttcaca | tacagtagca | aagcgccatt | atcttactct | 120 |
| accccattgg | caaacccaca | gccacaattt | tccaatcctc | cattatccct | tctacaattt | 180 |
| tctatataaa | tacccacatc | tctctgctct | actcccttat | tatcaacaac | aaccaccaaa | 240 |
| tttcttcttt | tttttcttcg | atagtagcaa | tctatcaaca | aaaacagaga | ccccatcaca | 300 |
| agaatcttgg | aattttagtg | ttgggtttaa | gaggaaaagg | ggttattgta | ttttgcagtt | 360 |
| ttgagggtaa | agcccagttt | aacaagttgt | agacatcacg | gctatacaca | aagtaaaccg | 420 |
| ccgaccactt | ttacatgttc | cagcagtacg | tcgtaagggt | tgtgtaacag | ctactaaccc | 480 |
| tgcgccgcac | ggtggacgtg | gcgctttgcc | ttctgaaggt | ggtagtcctt | ccgacctcct | 540 |
| cttccttgcc | ggcggcggtt | cttcctctc | cttctcctac | tagatatagt | tatacttact | 600 |
| atagatctct | agcttattac | gtacagttgt | atctagtatt | ctattgatta | ttcgaagaaa | 660 |
| acacacaaaa | agaagtaaag | cc | | | | 682 |

<210> SEQ ID NO 127
<211> LENGTH: 472
<212> TYPE: DNA
<213> ORGANISM: Solanum tuberosum

<400> SEQUENCE: 127

| | | | | | |
|---|---|---|---|---|---|
| taaggggtg | cttatataaa | gttggggagt | ctaccaatga | gacgaactca | ttgaccaaat | 60 |
| acgtctgcag | gagaaagacc | accggagcac | caaacgccac | ccaacaacca | cccattaaat | 120 |
| tcttccagaa | aaaacatct | tcctcaaaat | tatcgatgaa | ggatcgttcc | ttagtagttg | 180 |
| ttcgttgatc | ctacaaattc | aatcacgact | cttccttggat | cttttcgtttg | tattctcaca | 240 |

-continued

```
attcatcatc accgcaaagt gttgacccct aatccaactc ttctggtgga cgataagcac      300
cggacccctt ccctcacgg aggtaggggt gcctcacccg ctgaaggcgg ttgcccctcc       360
gatctcctct tcctcgccgg cggcggtcca attcttcctt tctctttctc cttctcctaa     420
tttttcgtgt aagaattgta tttttgatta tccatccaag aacaggaccg cc             472
```

<210> SEQ ID NO 128
<211> LENGTH: 607
<212> TYPE: DNA
<213> ORGANISM: Malus x domesticus

<400> SEQUENCE: 128

```
ccacggtaca ccctcagcca cgaacacccc ttcttctccc cacacctata aatccacccc      60
ctcatctcct ccccacaccc ccactcactt cagttcgaaa caggcgatcc tcgccttttct    120 gggttgtttc ctatttatc tgagggagaa gaaaggaagg tgtttgatca atttttttggt    180 atatttttag gggtaagacc caggttcgac gagttgtaga catcacggct atacacggag      240
ctcctcggcc gctcattcat gtccgggctg tccgacgaaa gggttgtgta attgagagca    300
acccttcgcc gcacggcggg cgtggcgctt tgccttccga aggcggtagc ccctccgacc    360
tgctcttcct cgctggtggc ggttctgcat cctctgtttt tctcttctgc ttatattagc    420
ttttttagac tttcttggtt agattcttag gagattttag agatttttt tcttctataa    480 agcgcacgag tagatcgtat tgttgttttc ggggggtttt gggtttggtg gtgtttgatt    540
ttactgagaa ttaagaaaaa ataaaaggaa aaaaagaga gagagaaaga aggggaggga    600
gcatgcc                                                              607
```

<210> SEQ ID NO 129
<211> LENGTH: 183
<212> TYPE: DNA
<213> ORGANISM: Solanum lycopersicum

<400> SEQUENCE: 129

```
acggctatac acaaagtaaa ccgccgacca cttttacatg ttccagcagt acgtcgtaag      60
ggttgtgtaa cagctactaa ccctgcgccg cacggtggac gtggcgcttt gccttctgaa    120
ggtggtagtc cttccgacct cctcttcctt gccggcggcg ttctttcct ctccttctcc    180 tac                                                                  183
```

<210> SEQ ID NO 130
<211> LENGTH: 213
<212> TYPE: DNA
<213> ORGANISM: Solanum tuberosum

<400> SEQUENCE: 130

```
acggctcttc ttggatcttt cgtttgtatt ctcacaattc atcatcaccg caaagtgttg     60
acccttaatc caactcttct ggtggacgat aagcaccgga ccccttcccc tcacggaggt    120
aggggtgcct cacccgctga aggcggttgc ccctccgatc tcctcttcct cgccggcggc    180
ggtccaattc ttcctttctc tttctccttc tcc                                 213
```

<210> SEQ ID NO 131
<211> LENGTH: 192
<212> TYPE: DNA
<213> ORGANISM: Malus x domesticus

<400> SEQUENCE: 131

```
acggctatac acggagctcc tcggccgctc attcatgtcc gggctgtccg acgaaagggt    60
tgtgtaattg agagcaaccc ttcgccgcac ggcgggcgtg gcgctttgcc ttccgaaggc   120
ggtagcccct ccgacctgct cttcctcgct ggtggcggtt ctgcatcctc tgttttctc    180 ttctgcttat at                                                       192
```

<210> SEQ ID NO 132
<211> LENGTH: 61
<212> TYPE: PRT
<213> ORGANISM: Solanum lycopersicum

<400> SEQUENCE: 132

```
Thr Ala Ile His Lys Val Asn Arg Arg Pro Leu Leu His Val Pro Ala
1               5                   10                  15

Val Arg Arg Lys Gly Cys Val Thr Ala Thr Asn Pro Ala Pro His Gly
            20                  25                  30

Gly Arg Gly Ala Leu Pro Ser Glu Gly Gly Ser Pro Ser Asp Leu Leu
        35                  40                  45

Phe Leu Ala Gly Gly Gly Ser Phe Leu Ser Phe Ser Tyr
    50                  55                  60
```

<210> SEQ ID NO 133
<211> LENGTH: 71
<212> TYPE: PRT
<213> ORGANISM: Solanum tuberosum

<400> SEQUENCE: 133

```
Thr Ala Leu Leu Gly Ser Phe Val Cys Ile Leu Thr Ile His His His
1               5                   10                  15

Arg Lys Val Leu Thr Leu Asn Pro Thr Leu Leu Val Asp Asp Lys His
            20                  25                  30

Arg Thr Pro Ser Pro His Gly Gly Arg Gly Ala Ser Pro Ala Glu Gly
        35                  40                  45

Gly Cys Pro Ser Asp Leu Leu Phe Leu Ala Gly Gly Gly Pro Ile Leu
    50                  55                  60

Pro Phe Ser Phe Ser Phe Ser
65                  70
```

<210> SEQ ID NO 134
<211> LENGTH: 64
<212> TYPE: PRT
<213> ORGANISM: Malus x domesticus

<400> SEQUENCE: 134

```
Thr Ala Ile His Gly Ala Pro Arg Pro Leu Ile His Val Arg Ala Val
1               5                   10                  15

Arg Arg Lys Gly Cys Val Ile Glu Ser Asn Pro Ser Pro His Gly Gly
            20                  25                  30

Arg Gly Ala Leu Pro Ser Glu Gly Gly Ser Pro Ser Asp Leu Leu Phe
        35                  40                  45

Leu Ala Gly Gly Gly Ser Ala Ser Ser Val Phe Leu Phe Cys Leu Tyr
    50                  55                  60
```

<210> SEQ ID NO 135
<211> LENGTH: 28
<212> TYPE: PRT
<213> ORGANISM: Solanum lycopersicum

<400> SEQUENCE: 135

Asn Pro Ala Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 136
<211> LENGTH: 28
<212> TYPE: PRT
<213> ORGANISM: Solanum tuberosum

<400> SEQUENCE: 136

Thr Pro Ser Pro His Gly Gly Arg Gly Ala Ser Pro Ala Glu Gly Gly
1               5                   10                  15

Cys Pro Ser Asp Leu Leu Phe Leu Ala Gly Gly Gly
            20                  25

<210> SEQ ID NO 137
<211> LENGTH: 28
<212> TYPE: PRT
<213> ORGANISM: Malus x domesticus

<400> SEQUENCE: 137

Asn Pro Ser Pro His Gly Gly Arg Gly Ala Leu Pro Ser Glu Gly Gly
1               5                   10                  15

Ser Pro Ser Asp Leu Leu Phe Leu Ala Gly Gly Gly
            20                  25

<210> SEQ ID NO 138
<211> LENGTH: 84
<212> TYPE: DNA
<213> ORGANISM: Solanum lycopersicum

<400> SEQUENCE: 138
aaccctgcgc cgcacggtgg acgtggcgct tgccttctg aaggtggtag tccttccgac    60
ctcctcttcc ttgccggcgg cggt                                          84

<210> SEQ ID NO 139
<211> LENGTH: 84
<212> TYPE: DNA
<213> ORGANISM: Solanum tuberosum

<400> SEQUENCE: 139 acccccttccc ctcacggagg tagggggtgcc tcacccgctg aaggcggttg ccccctccgat    60 ctcctcttcc tcgccggcgg cggt                                          84

<210> SEQ ID NO 140
<211> LENGTH: 84
<212> TYPE: DNA
<213> ORGANISM: Malus x domesticus

<400> SEQUENCE: 140
aacccttcgc cgcacggcgg gcgtggcgct tgccttccg aaggcggtag ccccctccgac    60 ctgctcttcc tcgctggtgg cggt                                          84

<210> SEQ ID NO 141
<211> LENGTH: 276
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature

```
<222> LOCATION: (3)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (65)..(67)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (87)..(89)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (104)..(106)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (125)..(127)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (211)..(215)
<223> OTHER INFORMATION: n is a, c, g, or t
<220> FEATURE:
<221> NAME/KEY: misc_feature
<222> LOCATION: (217)..(217)
<223> OTHER INFORMATION: n is a, c, g, or t
<220> FEATURE:
```

<220> FEATURE:
<221> NAME/KEY: misc_feature
<222> LOCATION: (230)..(231)
<223> OTHER INFORMATION: n is a, c, g, or t
<220> FEATURE:
<221> NAME/KEY: misc_feature
<222> LOCATION: (233)..(234)
<223> OTHER INFORMATION: n is a, c, g, or t
<220> FEATURE:
<221> NAME/KEY: misc_feature
<222> LOCATION: (240)..(241)
<223> OTHER INFORMATION: n is a, c, g, or t
<220> FEATURE:
<221> NAME/KEY: misc_feature
<222> LOCATION: (244)..(246)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(256)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (263)..(263)
<223> OTHER INFORMATION: n is a, c, g, or t
<220> FEATURE:
<221> NAME/KEY: misc_feature
<222> LOCATION: (266)..(267)
<223> OTHER INFORMATION: n is a, c, g, or t
<220> FEATURE:
<221> NAME/KEY: misc_feature
<222> LOCATION: (272)..(274)
<223> OTHER INFORMATION: n is a, c, g, or t

<400> SEQUENCE: 141
ggntaaaacc cggngtttga caagttgtag ancatcacgg ctatacacgg nangtttctn    60
cggcnnncnc tcatacatgt ccggncnnnt gtacgacgna aggnnngttg tgtaatngag   120
agcannnacc cttcgccgca cggcggacgt ggngctttgc cntcgaagg cggtagcccn    180 tccgacctcc tcttcctcgc cggcggcggt nnnnncnctt tcttcttctn ntnncttctn   240
nttnnnttat tnttnntttn gtnganntt annntt                              276

<210> SEQ ID NO 142
<211> LENGTH: 58
<212> TYPE: PRT
<213> ORGANISM: Artificial Sequence
<220> FEATURE:
<223> OTHER INFORMATION: Consensus Sequence

<400> SEQUENCE: 142

Thr Ala Ile Asn Asn Val Asn Arg Asn Leu Ile His Val Arg Asn Ala
1               5                   10                  15

Val Arg Arg Asn Asn Asn Lys Gly Cys Val Ile Glu Ser Asn Asn Pro
            20                  25                  30

Ser Pro His Gly Gly Arg Gly Ala Leu Pro Ser Glu Gly Gly Ser Pro
        35                  40                  45

Ser Asp Leu Leu Phe Leu Ala Gly Gly Gly
    50                  55

<210> SEQ ID NO 143
<211> LENGTH: 12
<212> TYPE: DNA
<213> ORGANISM: Artificial Sequence

```
-continued

<220> FEATURE:
<223> OTHER INFORMATION: Construct

<400> SEQUENCE: 143
gatctataga tc                                                          12
```

REGULATION OF GENE EXPRESSION VIA UORF OF GDP-L-GALACTOSE PHOSPHORYLASE (GGP) GENE

CROSS-REFERENCE TO RELATED APPLICATIONS

This application is a U.S. National Stage Application filed under 35 U.S.C. §371 of International Application No. PCT/IB2013/061166, filed Dec. 20, 2013, which claims the benefit of U.S. Provisional Application No. 61/740,751, filed Dec. 21, 2012. Both of these applications are hereby incorporated by reference in their entireties.

TECHNICAL FIELD

The present invention relates to control and manipulation of expression of GDP-L-Galactose phosphorylase (GGP) and ascorbate production. The invention also relates to sequence elements controlling such expression and production, and their use.

BACKGROUND ART

Ascorbate is the most abundant soluble antioxidant in plants and is also an essential nutrient for humans and a few other animals. Ascorbate contributes significantly to the overall intake of "free radical scavengers" or "anti-oxidative metabolites" in the human diet. Convincing evidence now shows that such metabolites either singly or in combination, benefit health and well-being, acting as anti-cancer forming agents and protecting against coronary heart disease.

Almost the entire dietary ascorbate intake in humans is derived from plant products. The ascorbate content of plant tissues however, is remarkably variable. Whilst leaf ascorbate content is generally high and relatively uniform in herbaceous and woody plants, a huge and unexplained variability in ascorbate content found is in non-green edible plant tissues. For example, in fruits, the levels vary from up to 30 mg gFW-1 AsA in the camu camu of *Mirciaria dubia*, to less than 3 μg gFW-1 AsA in the medlar of *Mespilus germanica* (Rodriguez et al. 1992, J Chromatogr Sci, 30:433-437). A range of values for ascorbate have been reported in kiwifruit (Ferguson, A. R., Botanical nomenclature: *Actinidia chinensis, Actinidia deliciosa*, and *Actinidia setosa*. Kiwifruit: science and management, ed. I. J. Warrington and G. C. Weston. 1990, Palmerston North; New Zealand: New Zealand Society for Horticultural Science. 576. Beever, D. J. and G. Hopkirk, Fruit development and fruit physiology. Kiwifruit: science and management, ed. I. J. Warrington and G. C. Weston. 1990, Palmerston North; New Zealand: New Zealand Society for Horticultural Science. 576.) Ascorbate content of fruits from different vines range for *A. deliciosa*, 30-400 mg/100 g (Ferguson, A. R., 1991 Acta Hort. 290: p. 603-656, Spano, D., et al., 1997 Acta Hort., 444: p. 501-506.) while for the cultivar 'Hayward' the reported range is 80-120 mg/100 g (Beever, D. J. and G. Hopkirk, Fruit development and fruit physiology. Kiwifruit: science and management, ed. I. J. Warrington and G. C. Weston. 1990, Palmerston North; New Zealand: New Zealand Society for Horticultural Science. 576.). Higher concentrations of ascorbate are reported in fruit of, *A. arguta, A. chinensis* (Muggleston, S., et al., Orchardist, 1998. 71(8): p. 38-40, Chen, Q. and Q. Chen, Crop Genetic Resources, 1998(2): p. 3, Coggiatti, S., 1971 Ital Agr, October, 108(10): p. 935-941) *A. chrysantha* and *A. polygama* with very high levels in *A. eriantha*, and *A. latifolia* (>1% fresh weight) (Ferguson 1991 Acta Hort. 290: p. 603-656, and *A. kolomikta* (Kola, J. and J. Pavelka, 1988 Nahrung, 32(5): p. 513-515).

Three pathways of biosynthesis of ascorbic acid have been proposed in plants, one through L-Galactose (L-Gal) (Wheeler et al., 1998, Nature 393, 365-369), another from myo-Inositol (Loewus & Kelly, 1961, Arch. Biochem. Biophys. 95, 483-493; Lorence et al., (2004) Plant Physiol. 134, 1200-1205) and a third through Galacturonic acid (Agius et al., 2003, Nat Biotechnol 21, 177-81). The L-Gal pathway proceeds through L-Gal to galactono-1,4-lactone and thence to ascorbate (Wheeler et al., 1998, Nature 393, 365-369).

All the genes encoding enzymes, and their associated enzymatic activities, for the L-Galactose pathway have been identified and at least partially characterised.

The characterised genes and enzyme activities include the GDP-D-Mannose Pyrophosphorylase (Conklin, 1998, Trends Plant Sci 3: 329-330.; Conklin et al., 1999 Proc Natl Acad Sci USA 96: 4198-4203.; Keller et al., 1999 Plant J 19: 131-141.), the GDP-D-Mannose 3',5'-Epimerase (Wolucka et al., 2001, Anal Biochem 294: 161-168; Wolucka and Van Montagu, 2003, J. Biol. Chem. 278: 47483-47490; Watanabe et al., 2006 Phytochemistry 67: 338-346.), the L-Galactose-1-P Phosphatase (Laing et al., 2004, Proceedings of the National Academy of Sciences (USA) 101: 16976-16981.; Conklin et al., 2006, J. Biol. Chem. 281: 15662-15670.), L-Galactose Dehydrogenase (Wheeler et al., 1998, Nature 393: 365-369.; Gatzek et al., 2002, *Plant J.* 30, 541 (2002; Laing et al., 2004 Proceedings of the National Academy of Sciences (USA) 101: 16976-16981), L-Galactono-1,4-lactone Dehydrogenase (Imai et al., 1998 Plant and Cell Physiology 39: 1350-1358.; Bartoli et al., 2005, Plant, Cell and Environment 28: 1073-1081.), and GDP-L galactose phosphorylase (GGP) (Laing et al., 2007, *Proceedings of the National Academy of Sciences (USA)* 104:9534-9). The applicants have previously shown that GDP-L galactose phosphorylase is central in determining ascorbate production Bulley S, et al 2012 Plant Biotechnol J 2012, 10:390-397.

Ascorbate concentrations are regulated according to demand. Under high light intensities when the need for high ascorbate is greatest, leaf ascorbate concentrations are raised (Bartoli et al., *J. Exp. Bot.* 57, 1621 (2006); Gatzek, et al., *Plant J.* 30, 541 (2002)). However little is known about the mechanism of regulation of ascorbate biosynthesis in plants (Bulley et al., *Plant Biotechnol J* 10, 390 (2012); Bulley et al., *J. Exp. Bot.* 60, 765 (2009).). Understanding how ascorbate biosynthesis is regulated may provide tools to manipulate biosynthesis in plants. Understanding the regulation of gene expression, and the factors/elements controlling such expression also provide valuable tools for genetic manipulation.

It is one object of the invention to provide improved compositions and methods for modulating GGP (also known as GDP-L-Galactose phosphorylase) activity; and/or ascorbate content in plants and/or to provide improved tools useful for genetic manipulation, or at least to provide the public with a useful choice.

SUMMARY OF THE INVENTION

In one aspect the invention provides an isolated polynucleotide comprising a sequence encoding a polypeptide with an amino acid sequence selected from SEQ ID NO:1 to 20 and 132 to 134 (uORF peptides) or a variant or fragment thereof.

In one embodiment the variant or fragment comprises a sequence with at least 70% Identity to an amino sequence selected from SEQ ID NO:21 to 40 and 135 to 137 (conserved region of uORF peptides).

In a further embodiment the variant or fragment comprises a sequence with an amino acid selected from SEQ ID NO:21 to 40 and 135 to 137 (conserved region of uORF peptides).

In one embodiment the variant or fragment comprises a sequence with at least 70% Identity to an amino sequence selected from SEQ ID NO: 21-30, 33-37 and 135 to 137 (conserved region of dicot uORF peptides).

In a further embodiment the variant or fragment comprises a sequence with an amino acid selected from SEQ ID NO: 21 to 30, 33 to 37 and 135 to 137 (conserved region of dicot uORF peptides).

In one embodiment the variant or fragment comprises a sequence with at least 70% Identity to the amino sequence of SEQ ID NO: 108 (consensus motif uORF peptides).

In a further embodiment the variant or fragment comprises the amino sequence of SEQ ID NO: 108 (consensus motif uORF peptides).

In a further embodiment the variant comprises a sequence with at least 70% identity to an amino acid sequence selected from SEQ ID NO:1 to 20 and 132 to 134 (uORF peptides).

In a further embodiment the variant comprises an amino acid sequence selected from SEQ ID NO:1 to 20 and 132 to 134 (uORF peptides).

In a further embodiment the variant comprises a sequence with at least 70% identity to an amino acid sequence selected from SEQ ID NO: 1 to 10, 13 to 17 and 132 to 134 (dicot uORF peptides).

In a further embodiment the variant comprises an amino acid sequence selected from SEQ ID NO: 1 to 10, 13 to 17 and 132 to 134 (dicot uORF peptides).

In a further embodiment the isolated polynucleotide comprises a sequence with at least 70% Identity to a sequence selected from SEQ ID NO:61 to 80 and 138 to 140 (conserved region of uORF DNA sequences).

In a further embodiment the isolated polynucleotide comprises a sequence selected from SEQ ID NO:61 to 80 and 138 to 140 (conserved region of uORF DNA sequences).

In a further embodiment the isolated polynucleotide comprises a sequence with at least 70% identity to a sequence selected from SEQ ID NO: 61 to 70, 73 to 77 and 138 to 140 (conserved region of dicot uORF DNA sequences).

In a further embodiment the isolated polynucleotide comprises a sequence selected from SEQ ID NO: 61 to 70, 73 to 77 and 138 to 140 (conserved region of dicot uORF DNA sequences).

In a further embodiment the isolated polynucleotide comprises a sequence with at least 70% Identity to a sequence selected from SEQ ID NO:41 to 60 and 129 to 131 (uORF DNA sequences).

In a further embodiment the isolated polynucleotide comprises a sequence selected from SEQ ID NO:41 to 60 and 129 to 131 (uORF DNA sequences).

In a further embodiment the isolated polynucleotide comprises a sequence with at least 70% Identity to a sequence selected from SEQ ID NO: 41 to 50, 53 to 57 and 129 to 131 (dicot uORF DNA sequences).

In a further embodiment the isolated polynucleotide comprises a sequence selected from SEQ ID NO: 41 to 50, 53 to 57 and 129 to 131 (dicot uORF DNA sequences).

In a further embodiment the isolated polynucleotide comprises a sequence with at least 70% Identity to a sequence selected from SEQ ID NO:111 to 125 (5'-UTR sub-sequences).

In a further embodiment the isolated polynucleotide comprises a sequence selected from SEQ ID NO:111 to 125 (5'-UTR sub-sequences).

In a further embodiment the isolated polynucleotide comprises a sequence with at least 70% Identity to a sequence selected from SEQ ID NO:81 to 100 and 126 to 128 (whole 5'-UTR sequences).

In a further embodiment the isolated polynucleotide comprises a sequence selected from SEQ ID NO:81 to 100 and 126 to 128 (whole 5'-UTR sequences).

In a further embodiment the isolated polynucleotide comprises a sequence with at least 70% Identity to a sequence selected from SEQ ID NO: 81 to 90, 93 to 97 and 125 to 128 (whole dicot 5'-UTR sequences).

In a further embodiment the isolated polynucleotide comprises a sequence selected from SEQ ID NO: 81 to 90, 93 to 97 and 125 to 128 (whole dicot 5'-UTR sequences).

In a further aspect the invention provides an isolated polynucleotide comprising a sequence selected from SEQ ID NO:41 to 60 and 129 to 131 (uORF DNA sequences) or a variant or fragment thereof.

In one embodiment the variant or fragment comprises a sequence with at least 70% identity to a sequence selected from SEQ ID NO:61 to 80 and 138 to 140 (conserved region of uORF DNA sequences).

In one embodiment the variant or fragment comprises a sequence with at least 70% identity to a sequence selected from SEQ ID NO: 61 to 70, 73 to 77 and 138 to 140 (conserved region of dicot uORF DNA sequences).

In a further embodiment the isolated polynucleotide comprises a sequence selected from SEQ ID NO: 41 to 60 and 129 to 131 (uORF DNA sequences).

In one embodiment the variant comprises a sequence with at least 70% identity to a sequence selected from SEQ ID NO:41 to 60 and 129 to 131 (uORF DNA sequences).

In one embodiment the variant comprises a sequence with at least 70% Identity to a sequence selected from SEQ ID NO: 41 to 50 and 53 to 57 and 129 to 131 (dicot uORF DNA sequences).

In a further embodiment the isolated polynucleotide comprises a sequence with at least 70% identity to a sequence selected from SEQ ID NO:111 to 125 (5'-UTR sub-sequences).

In a further embodiment the isolated polynucleotide comprises a sequence selected from SEQ ID NO: 111 to 125 (5'-UTR sub-sequences).

In a further embodiment the isolated polynucleotide comprises a sequence with at least 70% Identity to a sequence selected from SEQ ID NO:81 to 100 and 126 to 128 (whole 5'-UTR sequences).

In a further embodiment the isolated polynucleotide comprises a sequence selected from SEQ ID NO:81 to 100 and 126 to 128(whole 5'-UTR sequences).

In a further embodiment the isolated polynucleotide comprises a sequence with at least 70% identity to a sequence selected from SEQ ID NO: 81 to 90, 93 to 97 and 126 to 128 (whole dicot 5'-UTR sequences).

In a further embodiment the isolated polynucleotide comprises a sequence selected from SEQ ID NO: 81 to 90, 93 to 97 and 126 to 128 (whole dicot 5'-UTR sequences).

In a further aspect the invention provides an isolated polynucleotide with a sequence selected from SEQ ID NO 81 to 100 and 126 to 128 (whole 5'-UTR sequences) or a variant or fragment thereof.

In one embodiment the variant has at least 70% identity to a sequence selected from SEQ ID NO 81 to 100 and 126 to 128 (whole 5'-UTR sequences).

In a further aspect the invention provides an isolated polynucleotide with a sequence selected from SEQ ID NO 111 to 125 (5'-UTR sub-sequences) or a variant or fragment thereof.

In one embodiment the variant has at least 70% identity to a sequence selected from SEQ ID NO 111 to 125 (5'-UTR sub-sequences).

In a further embodiment the variant or fragment comprises a sequence with at least 70% Identity to a sequence selected from SEQ ID NO 41 to 60 and 129 to 131 (uORF DNA sequences).

In a further embodiment the variant or fragment comprises a sequence selected from SEQ ID NO 41 to 60 and 129 to 131 (uORF DNA sequences).

In a further embodiment the variant or fragment comprises a sequence with at least 70% identity to a sequence selected from SEQ ID NO 41 to 50, 53 to 57 and 129 to 131 (dicot uORF DNA sequences).

In a further embodiment the variant or fragment comprises a sequence selected from SEQ ID NO 41 to 50, 53 to 57 and 129 to 131 (dicot uORF DNA sequences).

In a further embodiment the variant or fragment comprises a sequence with at least 70% identity to a sequence selected from SEQ ID NO:61 to 80 and 138 to 140 (conserved region of uORF DNA sequences).

In a further embodiment the variant or fragment comprises a sequence selected from SEQ ID NO:61 to 80 and 138 to 140 (conserved region of uORF DNA sequences).

In a further embodiment the variant or fragment comprises a sequence with at least 70% Identity to a sequence selected from SEQ ID NO: 61 to 70, 73 to 77 and 138 to 140 (conserved region of dicot uORF DNA sequences).

In a further embodiment the variant or fragment comprises a sequence selected from SEQ ID NO: 61 to 70, 73 to 77 and 138 to 140 (conserved region of dicot uORF DNA sequences).

In a further embodiment the variant encodes a sequence with at least 70% identity to at least one of SEQ ID NO:21 to 40 and 135 to 137 (conserved region of uORF peptides).

In a further embodiment the variant encodes a sequence selected from at least one of SEQ ID NO:21 to 40 and 135 to 137 (conserved region of uORF peptides).

In a further embodiment the variant encodes a sequence with at least 70% identity to at least one of SEQ ID NO: 21 to 30, 33 to 37 and 135 to 137 (conserved region of dicot uORF peptides).

In a further embodiment the variant encodes a sequence selected from at least one of SEQ ID NO: 21 to 30, 33 to 37 and 135 to 137 (conserved region of dicot uORF peptides).

In one embodiment the variant or fragment comprises a sequence with at least 70% identity to the amino sequence of SEQ ID NO: 108 (consensus motif uORF peptides).

In a further embodiment the variant or fragment comprises the amino sequence of SEQ ID NO: 108 (consensus motif uORF peptides).

In a further embodiment the variant encodes a sequence with at least 70% Identity to at least one of SEQ ID NO:1 to 20 and 132 to 134 (uORF peptides).

In a further embodiment the variant or fragment encodes a sequence selected from at least one of SEQ ID NO:1 to 20 and 132 to 134 (uORF peptides).

In a further embodiment the variant encodes a sequence with at least 70% identity to at least one of SEQ ID NO: 1 to 10, 13 to 17 and 132 to 134 (dicot uORF peptides).

In a further embodiment the variant or fragment encodes a sequence selected from at least one of SEQ ID NO: 1 to 10, 13 to 17 and 132 to 134 (dicot uORF peptides).

In one embodiment the isolated polynucleotide is modified.

In one embodiment, the modification is at least one of a deletion, an addition, or a substitution of at least one nucleotide in the sequence encoding the 5'-UTR.

In one embodiment the modification, reduced, disrupts, or prevents translation of a uORF polypeptide with the sequence of any one of SEQ ID NO: 1 to 20 and 132 to 134 (uORF peptides) or a variant thereof.

In a further embodiment the modification reduces, disrupts or destroys the activity of a uORF polypeptide with the sequence of any one of SEQ ID NO: 1 to 20 and 132 to 134 (uORF peptides) or a variant thereof.

In one embodiment the variant comprises a sequence with at least 70% identity to any one of SEQ ID NO: 1 to 20 and 132 to 134 (uORF peptides).

In a further embodiment the variant comprises a sequence with at least 70% Identity to any one of SEQ ID NO: 1 to 10, 13 to 17 and 132 to 134 (dicot uORF peptides).

In a further embodiment the variant comprises a sequence with at least 70% identity to at least one of SEQ ID NO: 21 to 40 and 135 to 137 (uORF peptides conserved region).

In a further embodiment the variant comprises a sequence with at least one of SEQ ID NO: 21 to 40 and 135 to 137 (uORF peptides conserved region).

In a further embodiment the variant comprises a sequence with at least 70% identity to at least one of SEQ ID NO: 21 to 30, 33 to 37 and 135 to 137 (dicot uORF peptides conserved region).

In a further embodiment the variant comprises a sequence with at least one of SEQ ID NO: 21 to 30, 33 to 37 and 135 to 137 (dicot uORF peptides conserved region).

In one embodiment the variant or fragment comprises a sequence with at least 70% identity to the amino sequence of SEQ ID NO: 108 (consensus motif uORF peptides).

In a further embodiment the variant or fragment comprises the amino sequence of SEQ ID NO: 108 (consensus motif uORF peptides).

In one embodiment the polynucleotide, or variant, or fragment, is operably linked to a nucleic acid sequence of interest.

In a further embodiment the nucleic acid sequence of interest encodes a protein of interest.

In one embodiment the polynucleotide and nucleic acid sequence are not normally associated in nature.

When the polynucleotide is modified as discussed above, to disrupt expression or activity of the uORF polypeptide, the operably liked sequence may be a GGP sequence. In this embodiment the modification removes repression, via the uORF, by ascorbate. Expressing the GGP under the control of the modified polynucleotide may advantageously retain spatial and/or temporal expression of GGP similar to control by the native GGP promoter and 5'-UTR but stop the negative regulation of expression by ascorbate via the uORF polypeptide. In this embodiment the polynucleotide and nucleic acid sequence of interest may be normally associated in nature, except that the polynucleotide is in a modified form as discussed above.

Polypeptides

In a further aspect the invention provides an isolated polypeptide comprising a sequence selected from any one of SEQ ID NO:1 to 20 and 132 to 134 (uORF peptides) or a variant or fragment thereof.

In one embodiment the variant or fragment comprises a sequence with at least 70% identity to a sequence selected from SEQ ID NO:21 to 40 and 135 to 137 (conserved region of uORF peptides).

In a further embodiment the variant or fragment comprises a sequence selected from SEQ ID NO:21 to 40 and 135 to 137 (conserved region of uORF peptides).

In one embodiment the variant or fragment comprises a sequence with at least 70% Identity to a sequence selected from SEQ ID NO: 21 to 30, 33 to 37 and 135 to 137 (conserved region of dicot uORF peptides).

In a further embodiment the variant or fragment comprises a sequence selected from SEQ ID NO: 21 to 30, 33 to 37 and 135 to 137 (conserved region of dicot uORF peptides).

In one embodiment the variant or fragment comprises a sequence with at least 70% identity to the amino sequence of SEQ ID NO: 108 (consensus motif uORF peptides).

In a further embodiment the variant or fragment comprises the amino sequence of SEQ ID NO: 108 (consensus motif uORF peptides).

In a further embodiment the variant comprises a sequence with at least 70% identity to a sequence selected from SEQ ID NO:1 to 20 and 132 to 134 (uORF peptides).

In a further embodiment the variant comprises a sequence with at least 70% identity to a sequence selected from SEQ ID NO: 1 to 10, 13 to 17 and 132 to 134 (dicot uORF peptides).

Construct

In a further embodiment the invention provides a construct comprising a polynucleotide of the invention.

In one embodiment the polynucleotide is operably linked to a nucleic acid sequence of interest.

In a further embodiment the polynucleotide and nucleic acid sequence are not normally associated in nature.

In a further embodiment the nucleic acid sequence of interest encodes a protein of interest.

Activity of Polynucleotides

In one embodiment the polynucleotide of the invention is regulatable by a compound.

In this embodiment the expression of any nucleic acid sequence operably linked to the polynucleotide of the invention is regulated by the compound.

In a preferred embodiment regulation is post-transcriptional.

Preferably expression of the polypeptide encoded by the operably linked nucleic acid is regulated by the compound.

In one embodiment, expression of the operably linked nucleic acid is regulated by interaction between the compound and the uORF peptide expressed by the polynucleotide of the invention. In one embodiment interaction is direct. In a further embodiment the interaction is indirect. In a further embodiment the indirect interaction is via a further protein.

In one embodiment the compound is ascorbate, or a related metabolite. In a preferred embodiment the compound is ascorbate When modified, as discussed above, the polynucleotide may no longer be regulatable by the compound. An application of this embodiment could be to express a GGP coding sequence under the control of the modified polynucleotide sequence. In this embodiment, the modification results in a reduction or removal of repression by the compound. When the compound is ascorbate, this results in a loss of a repression of GGP translation, and hence increased GGP production and increased ascorbate accumulation. In this embodiment the modification of the uORF, or uORF encoding sequence, may be in the context of the promoter and 5'-UTR sequence. Examples of the whole GGP promoter and 5-UTR sequence are provided in SEQ ID NO: 101 to 107 or a variant thereof. Use of the modified uORF in the context of the promoter and 5'-UTR sequence may retain some spatial or temporal expression of a native GGP sequence, but without repression of GGP translation by ascorbate via the uORF polypeptide.

Cell

In a further embodiment the invention provides a cell comprising a polynucleotide of the invention, or a construct of the invention.

Preferably the cell, or it precursor cell, has been genetically modified to comprise the polynucleotide of the invention, or a construct of the invention.

Preferably the cell, or it precursor cell, has been transformed to comprise the polynucleotide of the invention, or a construct of the invention.

Plant Cells and Plants

In a further embodiment the invention provides a plant cell or plant comprising a polynucleotide of the invention or a construct of the invention.

Preferably the plant cell or plant, or it precursor plant cell or plant, has been genetically modified to comprise the polynucleotide of the invention, or a construct of the invention.

Preferably the plant cell or plant, or it precursor plant cell or plant, has been transformed to comprise the polynucleotide of the invention, or a construct of the invention.

Also Express an Epimerase

In one embodiment the cell or plant is also genetically modified, or transformed, to express a polynucleotide encoding a GDP-D-Mannose epimerase.

Preferably the cell or plant also comprises an expression construct of the invention capable of expressing a GDP-D-Mannose epimerase.

Plant Part or Propagule

In a further embodiment the invention provides a plant part or propagule comprising a polynucleotide of the invention or a construct of the invention.

Preferably the plant part or propagule, or it precursor plant cell or plant, has been genetically modified to comprise the polynucleotide of the invention, or a construct of the invention.

Preferably the plant part or propagule, or it precursor plant cell or plant, has been transformed to comprise the polynucleotide of the invention, or a construct of the invention.

In a further aspect the invention provides a method for controlling or regulating expression of at least one nucleic acid sequence in a cell comprising transformation of the cell with a polynucleotide or construct of the invention.

In a further aspect the invention provides a method for controlling expression of at least one nucleic acid sequence in a plant cell or plant comprising transformation of the plant cell or plant with a polynucleotide or construct of the invention.

In a further aspect the invention provides a method for producing a cell with modified gene expression the method comprising transforming the cell with a polynucleotide or construct of the invention.

In a further aspect the invention provides a method for producing a plant cell or plant with modified gene expression the method comprising transforming plant cell or plant with a polynucleotide or construct of the invention.

In a further aspect of the invention provides a method for modifying the phenotype of a plant, the method including the stable incorporation into the genome of the plant, a polynucleotide or construct of the invention.

Those skilled in the art will understand that introduction of the polynucleotide of the invention into the cell, plant cell, or plant, may result in regulation or control of a nucleic acid sequence that is operably linked to the nucleic acid sequence before these sequences are introduced. In such an embodiment the polynucleotide of the invention and operably linked nucleic acid of interest will be introduced together, for example on a construct of the invention.

In an alternative embodiment, the polynucleotide of the invention may be inserted into the genome, and control or regulate expression of a nucleic acid sequence, such as a protein encoding nucleic acid sequence, adjacent to the site of insertion.

In a preferred embodiment, the cell, plant cell or plant produces a compound that regulates or controls expression via the introduced polynucleotide of the invention, or via a uORF polypeptide encoded by the introduced polynucleotide of the invention.

Alternatively the compound may be applied to the cell, plant cell or plant.

In a further aspect the invention provides a plant cell or plant produced by a method of the invention.

In one aspect the invention provides a method for producing a plant cell or plant with at least one of:
  increased GGP translation,
  increased GGP production,
  increased GGP activity, and
  increased ascorbate production,
the method comprising modification of the 5'-UTR of a GGP gene in the plant cell or plant.

In one embodiment, the 5'-UTR is in the context of a polynucleotide sequence selected from any one of SEQ ID NO: 101 to 107 (GGP genomic sequences with promoter a 5'-UTR) or a variant thereof.

Preferably the variant has at least 70% Identity to the sequence of any one of SEQ ID NO: 101 to 107 (GGP genomic sequences with promoter a 5'-UTR).

In a further embodiment the 5'-UTR has a polynucleotide sequence selected from any one of SEQ ID NO: 81 to 100 and 126 to 128 (whole 5'-UTR sequences) or a variant thereof.

Preferably the variant has at least 70% Identity to the sequence of any one of SEQ ID NO: 81 to 100 and 126 to 128 (whole 5'-UTR sequences).

In a preferred embodiment the modification is in a uORF sequence in the 5'-UTR.

In a preferred embodiment the uORF has a sequence selected from any one of SEQ ID NO: 41 to 60 and 129 to 131 (uORF DNA sequences) or a variant thereof.

In a preferred embodiment the variant has at least 70% Identity to any one of SEQ ID NO: 41 to 60 and 129 to 131 (uORF DNA sequences).

In a preferred embodiment the variant has at least 70% identity to any one of SEQ ID NO: 41-50, 53-57 and 129 to 131 (dicot uORF DNA sequences).

In a further embodiment the variant comprises a sequence with at least 70% identity to any one of SEQ ID NO: 61-80 and 138 to 140 (conserved region of uORF DNA sequences).

In a further embodiment the variant comprises the sequence of any one of SEQ ID NO: 61-80 and 138 to 140 (conserved region of uORF DNA sequences).

In a further embodiment the variant comprises a sequence with at least 70% identity to any one of SEQ ID NO: 61-70, 73-77 and 138 to 140 (conserved region of dicot uORF DNA sequences).

In a further embodiment the variant comprises the sequence of any one of SEQ ID NO: 61-70, 73-77 and 138 to 140 (conserved region of dicot uORF DNA sequences).

In a further embodiment the uORF has the sequence of any one of SEQ ID NO:1 to 20 and 132 to 134 (uORF polypeptide sequences) or a variant thereof.

In a further embodiment the variant has at least 70% identity the sequence of any one of SEQ ID NO: 1 to 20 and 132 to 134 (uORF polypeptide sequences).

In a further embodiment the variant has the sequence of any one of SEQ ID NO: 1 to 20 and 132 to 134 (uORF polypeptide sequences).

In a further embodiment the variant has at least 70% Identity the sequence of any one of SEQ ID NO: 1 to 10, 13 to 17 and 132 to 134 (dicot uORF polypeptide sequences).

In a further embodiment the variant has the sequence of any one of SEQ ID NO: 1 to 10, 13 to 17 and 132 to 134 (dicot uORF polypeptide sequences).

In a further embodiment the variant has at least 70% identity the sequence of any one of SEQ ID NO: 21 to 40 and 135 to 137 (conserved region of uORF polypeptide sequences).

In a further embodiment the variant has the sequence of any one of SEQ ID NO:21 to 40 and 135 to 137 (conserved region of uORF polypeptide sequences).

In a further embodiment the variant has at least 70% identity the sequence of any one of SEQ ID NO: 21 to 30, 33 to 37 and 135 to 137 (conserved region of dicot uORF polypeptide sequences).

In a further embodiment the variant has the sequence of any one of SEQ ID NO: 21 to 30, 33 to 37 and 135 to 137 (conserved region of dicot uORF polypeptide sequences).

In one embodiment the variant or fragment comprises a sequence with at least 70% identity to the amino sequence of SEQ ID NO: 108 (consensus motif uORF peptides).

In a further embodiment the variant or fragment comprises the amino sequence of SEQ ID NO: 108 (consensus motif uORF peptides).

Modification

In one embodiment, the modification is at least one of a deletion, an addition, or a substitution of at least one nucleotide in the sequence encoding the 5'-UTR.

In one embodiment the modification, reduced, disrupts, or prevents translation of a uORF polypeptide with the sequence of any one of SEQ ID NO: 1 to 20 and 132 to 134 (uORF peptides) or a variant thereof.

In a further embodiment the modification reduces, disrupts or destroys the activity of a uORF polypeptide with the sequence of any one of SEQ ID NO: 1 to 20 and 132 to 134 (uORF peptides) or a variant thereof.

In one embodiment the variant comprises a sequence with at least 70% identity to any one of SEQ ID NO: 1 to 20 and 132 to 134 (uORF peptides).

In a further embodiment the variant comprises a sequence with at least 70% identity to any one of SEQ ID NO: 1 to 10, 13 to 17 and 132 to 134 (dicot uORF peptides).

In a further embodiment the variant comprises a sequence with at least 70% identity to at least one of SEQ ID NO: 21 to 40 and 135 to 137 (uORF peptides conserved region).

In a further embodiment the variant comprises a sequence with at least one of SEQ ID NO: 21 to 40 and 135 to 137 (uORF peptides conserved region).

In a further embodiment the variant comprises a sequence with at least 70% identity to at least one of SEQ ID NO: 21 to 30, 33 to 37 and 135 to 137 (dicot uORF peptides conserved region).

In a further embodiment the variant comprises a sequence with at least one of SEQ ID NO: 21 to 30, 33 to 37 and 135 to 137 (dicot uORF peptides conserved region).

In one embodiment the variant or fragment comprises a sequence with at least 70% identity to the amino sequence of SEQ ID NO: 108 (consensus motif uORF peptides).

In a further embodiment the variant or fragment comprises the amino sequence of SEQ ID NO: 108 (consensus motif uORF peptides).

In a further aspect the invention provides a method for selecting a plant with at least one of:
  a) Increased GGP translation,
  b) increased GGP production,
  c) increased GGP activity, and
  d) increased ascorbate production,
the method comprising testing of a plant for the presence of a first polymorphism in a polynucleotide of the invention in the plant, or a further polymorphism linked to the first polymorphism.

In one embodiment presence of the first polymorphism, or the further polymorphism linked to the first polymorphism, Is indicative of at least one of a) to d).

In a further embodiment the further polymorphism is in linkage disequilibrium (LD) with the first polymorphism.

In a further embodiment the method includes the step of separating a selected plant from one of more non-selected plants.

In a further aspect the invention provides a plant selected by the method of the invention.

In a further aspect the invention provides a group of plants selected by the method of the invention. Preferably the group comprises at least 2, more preferably at least 3, more preferably at least 4, more preferably at least 5, more preferably at least 6, more preferably at least 7, more preferably at least 8, more preferably at least 9, more preferably at least 10, more preferably at least 11, more preferably at least 12, more preferably at least 13, more preferably at least 14, more preferably at least 15, more preferably at least 16, more preferably at least 17, more preferably at least 18, more preferably at least 19, more preferably at least 20 plants.

In a further aspect the invention provides a method of producing ascorbate, the method comprising extracting ascorbate from a plant cell or plant of the invention.

In a further aspect the invention provides an antibody raised against a polypeptide of the invention. In a further embodiment the invention provides an antibody specific for a polypeptide of the invention.

The polynucleotides, polypeptides, variants and fragments, of the invention may be derived from any species. The polynucleotides, polypeptides, variants and fragments may be naturally occurring or non-naturally occurring. The polynucleotides, variants and fragments may be recombinantly produced and also may be the products of "gene shuffling' approaches.

In one embodiment the polynucleotide, polypeptide, variant or fragment, is derived from any plant species. The plant to be transformed or modified in the methods of the invention may be from any plant species. The plant cells to be transformed or modified in the methods of the invention may be from any plant species.

In a further embodiment the plant is from a gymnosperm plant species.

In a further embodiment the plant is from an angiosperm plant species.

In a further embodiment the plant is from a from dicotyledonuous plant species.

In a further embodiment the plant is from a fruit species selected from a group comprising but not limited to the following genera: *Actinidia, Malus, Citrus, Fragaria* and *Vaccinium*.

Particularly preferred fruit plant species are: *Actidinia deliciosa, A. chinensis, A. eriantha, A. arguta*, hybrids of the four *Actinidia* species, *Malus domestica* and *Malus sieboldii*.

In a further embodiment the plant is selected from the group consisting of *Actinidia eriantha, Cucumis sativus, Glycine max, Solanum lycopersicum, Vitis vinifera, Arabidopsis thaliana, Malusxdomesticus, Medicago truncatula, Populus trichocarpa, Actinidia arguta, Actinidia chinensis, Fragaria vulgaris, Solanum tuberosum*, and *Zea mays*.

In a further embodiment the plant is from a vegetable species selected from a group comprising but not limited to the following genera: *Brassica, Lycopersicon* and *Solanum*.

Particularly preferred vegetable plant species are: *Lycopersicon esculentum* and *Solanum tuberosum*.

In a further embodiment the plant is from monocotyledonous species.

In a further embodiment the plant is from a crop species selected from a group comprising but not limited to the following genera: *Glycine, Zea, Hordeum* and *Oryza*.

Particularly preferred crop plant species are: *Oryza sativa, Glycine max* and *Zea mays*.

In a further embodiment the plant is selected from the group consisting of *Actinidia eriantha, Cucumis sativus, Glycine max, Solanum lycopersicum, Vitis vinifera, Arabidopsis thaliana, Malusxdomesticus, Medicago truncatula, Populus trichocarpa, Actinidia arguta, Actinidia chinensis, Fragaria vulgaris, Solanum tuberosum*, and *Zea mays*.

DETAILED DESCRIPTION

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In certain embodiments the term "comprising" and related terms such as "comprise" and "comprises", can be replaced with "consisting" and related terms, such as "consist" and "consists".

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, sIRNA, miRNA, tRNA, ribozymes, recombinant polypeptides, Isolated and purified naturally occurring DNA or RNA sequences, synthetic RNA and DNA sequences, nucleic acid probes, primers and fragments.

Preferably the term "polynucleotide" Includes both the specified sequence and its compliment.

A "fragment" of a polynucleotide sequence provided herein is a subsequence of contiguous nucleotides, e.g., a sequence that is at least 15 nucleotides in length.

The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention.

The term "primer" refers to a short polynucleotide, usually having a free 3'OH group, that is hybridized to a template and used for priming polymerization of a polynucleotide complementary to the target.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide. Preferably the fragment performs a function that is required for the biological activity and/or provides three dimensional structure of the polypeptide.

The term "isolated" as applied to the polynucleotide or polypeptide sequences disclosed herein is used to refer to sequences that are removed from their natural cellular environment. In one embodiment the sequence is separated from its flanking sequences as found in nature. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequence of the present invention. Identity is found over a comparison window of at least 20 nucleotide positions, preferably at least 50 nucleotide positions, more preferably at least 100 nucleotide positions, and most preferably over the entire length of a polynucleotide of the invention.

Polynucleotide sequence identity can be determined in the following manner. The subject polynucleotide sequence is compared to a candidate polynucleotide sequence using BLASTN (from the BLAST suite of programs, version 2.2.5 [November 2002]) In bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp colon slash slash file transfer protocol.nc-bi.nih.gov/blast/). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http colon slash slash world wide web.hgmp.mrc.a-c.uk/Software/EMBOSS/. The European Bioinformatics Institute server also provides the facility to perform EMBOSS-needle global alignments between two sequences on line at http colon slash slash world wide web.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

A preferred method for calculating polynucleotide % sequence identity is based on aligning sequences to be compared using Clustal X (Jeanmougin et al., 1998, Trends Biochem. Sci. 23, 403-5.)

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp colon slash slash file transfer protocol ftp.ncbi.nih.gov/blast/).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than 1×10-6 more preferably less than 1×10-9, more preferably less than 1×10-12, more preferably less than 1×10-15, more preferably less than 1×10-18, more preferably less than 1×10-21, more preferably less than 1×10-30, more preferably less than 1×10-40, more preferably less than 1×10-50, more preferably less than 1×10-60, more preferably less than 1×10-70, more preferably less than 1×10-80, more preferably less than 1×10-90 and most preferably less than 1×10-100 when compared with any one of the specifically identified sequences.

Alternatively, variant polynucleotides of the present invention hybridize to the specified polynucleotide sequences, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81. 5+0. 41% (G+C-log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp colon slash slash file transfer protocol ftp.ncbi.nih.gov/blast/) via the tblastx algorithm as previously described.

The function of a variant polynucleotide of the invention as a GGP may be assessed for example by expressing such a sequence in bacteria and testing activity of the encoded protein as described in the Example section. Function of a variant may also be tested for it ability to alter GGP activity or ascorbate content in plants, also as describe in the Examples section herein.

The function of a variant polynucleotide of the invention as a GDP-D-Mannose epimerase may be assessed for example by expressing such a sequence in bacteria and testing activity of the encoded protein as described in the Example section. Function of a variant may also be tested for it ability to alter GDP-D-Mannose epimerase activity or ascorbate content in plants, also as describe in the Examples section herein.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp colon slash slash file transfer protocol ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http colon slash slash world wide web.ebi.ac.uk/emboss/align/) and GAP (Huang, X. (1994) On Global Sequence Alignment. Computer Applications in the Biosciences 10, 227-235.) as discussed above are also suitable global sequence alignment programs for calculating polypeptide sequence identity.

A preferred method for calculating polypeptide % sequence identity is based on aligning sequences to be compared using Clustal X (Jeanmougin et al., 1998, Trends Biochem. Sci. 23, 403-5.)

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp colon slash slash file transfer protocol ftp.ncbi.nih.gov/blast/). The similarity of polypeptide sequences may be examined using the following unix command line parameters:

bl2seq -i peptideseq1 -j peptideseq2 -F F -p blastp

Variant polypeptide sequences preferably exhibit an E value of less than $1\times10^{-6}$ more preferably less than $1\times10^{-9}$, more preferably less than $1\times10^{-12}$, more preferably less than $1\times10^{-15}$, more preferably less than $1\times10^{-18}$, more preferably less than $1\times10^{-21}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably $1\times10^{-100}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

A variant polypeptide includes a polypeptide wherein the amino acid sequence differs from a polypeptide herein by one or more conservative amino acid substitutions, deletions, additions or insertions which do not affect the biological activity of the peptide. Conservative substitutions typically include the substitution of one amino acid for another with similar characteristics, e.g., substitutions within the following groups: valine, glycine; glycine, alanine; valine, Isoleucine, leucine; aspartic acid, glutamic acid; asparagines, glutamine; serine, threonine; lysine, arginine; and phenylalanine, tyrosine.

Non-conservative substitutions will entail exchanging a member of one of these classes for a member of another class.

Analysis of evolved biological sequences has shown that not all sequence changes are equally likely, reflecting at least in part the differences in conservative versus non-conservative substitutions at a biological level. For example, certain amino acid substitutions may occur frequently, whereas others are very rare. Evolutionary changes or substitutions in amino acid residues can be modelled by a scoring matrix also referred to as a substitution matrix. Such matrices are used in bioinformatics analysis to identify relationships between sequences, one example being the BLOSUM62 matrix shown below (Table A).

TABLE A

The BLOSUM62 matrix containing all possible substitution scores [Henikoff and Henikoff, 1992].

|   | A  | R  | N  | D  | C  | Q  | E  | G  | H  | I  |
|---|----|----|----|----|----|----|----|----|----|----|
| A | 4  | -1 | -2 | -2 | 0  | -1 | -1 | 0  | -2 | -1 |
| R | -1 | 5  | 0  | -2 | -3 | 1  | 0  | -2 | 0  | -3 |
| N | -2 | 0  | 6  | 1  | -3 | 0  | 0  | 0  | 1  | -3 |
| D | -2 | -2 | 1  | 6  | -3 | 0  | 2  | -1 | -1 | -3 |
| C | 0  | -3 | -3 | -3 | 9  | -3 | -4 | -3 | -3 | -1 |
| Q | -1 | 1  | 0  | 0  | -3 | 5  | 2  | -2 | 0  | -3 |
| E | -1 | 0  | 0  | 2  | -4 | 2  | 5  | -2 | 0  | -3 |
| G | 0  | -2 | 0  | -1 | -3 | -2 | -2 | 6  | -2 | -4 |
| H | -2 | 0  | 1  | -1 | -3 | 0  | 0  | -2 | 8  | -3 |
| I | -1 | -3 | -3 | -3 | -1 | -3 | -3 | -4 | -3 | 4  |
| L | -1 | -2 | -3 | -4 | -1 | -2 | -3 | -4 | -3 | 2  |

TABLE A-continued

The BLOSUM62 matrix containing all possible substitution scores [Henikoff and Henikoff, 1992].

|   | A  | R  | N  | D  | C  | Q  | E  | G  | H  | I  |
|---|----|----|----|----|----|----|----|----|----|----|
| K | -1 | 2  | 0  | -1 | -3 | 1  | 1  | -2 | -1 | -3 |
| M | -1 | -1 | -2 | -3 | -1 | 0  | -2 | -3 | -2 | 1  |
| F | -2 | -3 | -3 | -3 | -2 | -3 | -3 | -3 | -1 | 0  |
| P | -1 | -2 | -2 | -1 | -3 | -1 | -1 | -2 | -2 | -3 |
| S | 1  | -1 | 1  | 0  | -1 | 0  | 0  | 0  | -1 | -2 |
| T | 0  | -1 | 0  | -1 | -1 | -1 | -1 | -2 | -2 | -1 |
| W | -3 | -3 | -4 | -4 | -2 | -2 | -3 | -2 | -2 | -3 |
| Y | -2 | -2 | -2 | -3 | -2 | -1 | -2 | -3 | 2  | -1 |
| V | 0  | -3 | -3 | -3 | -1 | -2 | -2 | -3 | -3 | 3  |

The BLOSUM62 matrix shown is used to generate a score for each aligned amino acid pair found at the intersection of the corresponding column and row. For example, the substitution score from a glutamic acid residue (E) to an aspartic acid residue (D) is 2. The diagonal show scores for amino acids which have not changed. Most substitutions changes have a negative score. The matrix contains only whole numbers.

Determination of an appropriate scoring matrix to produce the best alignment for a given set of sequences is believed to be within the skill of in the art. The BLOSUM62 matrix in table 1 is also used as the default matrix in BLAST searches, although not limited thereto.

Other variants include peptides with modifications which influence peptide stability. Such analogs may contain, for example, one or more non-peptide bonds (which replace the peptide bonds) in the peptide sequence. Also included are analogs that include residues other than naturally occurring L-amino acids, e.g. D-amino acids or non-naturally occurring synthetic amino acids, e.g. beta or gamma amino acids and cyclic analogs The function of a polypeptide variant as a GGP may be assessed by the methods described in the Example section herein.

The function of a polypeptide variant as a GDP-D-Mannose epimerase may be assessed by the methods described in the Example section herein.

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule.

A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequence of interest, such as a sequence to be expressed is placed under the control of, and typically connected to another sequence comprising regulatory elements that may include promoters, tissue-specific regulatory elements, temporal regulatory elements, enhancers, repressors and terminators, 5'-UTR sequences, 5'-UTR sequences comprising uORFs, and uORFs.

In a preferred embodiment the regulatory elements include a polynucleotide sequence of the invention.

Preferably the sequence of the invention comprises a 5'-UTR sequence. Preferably the 5'-UTR sequence comprises a uORF.

The term "noncoding region" refers to untranslated sequences that are upstream of the translational start site and downstream of the translational stop site. These sequences are also referred to respectively as the 5'-UTR and the 3'-UTR. These regions include elements required for transcription initiation and termination and for regulation of translation efficiency.

A 5'-UTR sequence is the sequence between the transcription initiation site, and the translation start site.

The 5'-UTR sequence is an mRNA sequence encoded by the genomic DNA. However as used herein the term 5'-UTR sequence includes the genomic sequence encoding the 5'-UTR sequence, and the compliment of that genomic sequence, and the 5'-UTR mRNA sequence.

Terminators are sequences, which terminate transcription, and are found in the 3' untranslated ends of genes downstream of the translated sequence. Terminators are important determinants of mRNA stability and in some cases have been found to have spatial regulatory functions.

The term "uORF" or "upstream open reading frame" is an mRNA element, defined by a start codon (any three base pair codon with at least two of the following bases in order: AUG) in the 5'-UTR, with an in frame stop codon (UAA, UAG, UGA), that is upstream (i.e. in a 5' direction) and not overlapping with the main coding sequence.

The term "promoter" refers to cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

A "transgenic plant" refers to a plant which contains new genetic material as a result of genetic manipulation or transformation. The new genetic material may be derived from a plant of the same species as the resulting transgenic plant or from a different species.

An "inverted repeat" is a sequence that is repeated, where the second half of the repeat is in the complementary strand, e.g., (5')GATCTA...TAGATC(3')

(3')CTAGAT...ATCTAG(5')

Read-through transcription will produce a transcript that undergoes complementary base-pairing to form a hairpin structure provided that there is a 3-5 bp spacer between the repeated regions.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

Methods for Isolating or Producing Polynucleotides

The polynucleotide molecules of the invention can be isolated by using a variety of techniques known to those of ordinary skill in the art. By way of example, such polypeptides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides of the invention include use of all, or portions of, the polypeptides having the sequence set forth herein as hybridization probes. The technique of hybridizing labelled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5. 0×SSC, 0. 5% sodium dodecyl sulfate, 1×Denhardt's solution; washing (three washes of twenty minutes each at 55° C.) in 1. 0×SSC, 1% (w/v) sodium dodecyl sulfate, and optionally one wash (for twenty minutes) in 0. 5×SSC, 1% (w/v) sodium dodecyl sulfate, at 60° C. An optional further wash (for twenty minutes) can be conducted under conditions of 0. 1×SSC, 1% (w/v) sodium dodecyl sulfate, at 60° C.

The polynucleotide fragments of the invention may be produced by techniques well-known in the art such as restriction endonuclease digestion, oligonucleotide synthesis and PCR amplification.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, Nucleic Acids Res 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species.

Variants (including orthologues) may be identified by the methods described.

Methods for Identifying Variants

Physical Methods

Variant polypeptides may be identified using PCR-based methods (Mullis et al., Eds. 1994 The Polymerase Chain Reaction, Birkhauser). Typically, the polynucleotide sequence of a primer, useful to amplify variants of polynucleotide molecules of the invention by PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp colon slash slash file transfer protocol ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, Including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) Indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: Improving the sensitivity of progressive multiple sequence alignment through sequence weighting, positions-specific gap penalties and weight matrix choice. Nucleic Acids Research, 22:4673-4680, http colon slash slash world wide web -igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (world wide web.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, Guide to Protein Purification,).

Alternatively the polypeptides and variant polypeptides of the invention may be expressed recombinantly in suitable host cells and separated from the cells as discussed below.

Methods for Modifying Sequences

Methods for modifying the sequence of proteins, or the polynucleotide sequences encoding them, are well known to those skilled in the art. The sequence of a protein may be conveniently be modified by altering/modifying the sequence encoding the protein and expressing the modified protein. Approaches such as site-directed mutagenesis may be applied to modify existing polynucleotide sequences. Alternatively restriction endonucleases may be used to excise parts of existing sequences. Altered polynucleotide sequences may also be conveniently synthesised in a modified form.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, Insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Polynucleotides, Constructs or Vectors The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Methods for transforming plant cells, plants and portions thereof with polypeptides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297, Hellens R P, et al (2000) Plant Mol Biol 42: 819-32, Hellens R et al (2005) Plant Meth 1: 13). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, Inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3' (coding strand)    3'CTAGAT 5'
                               (antisense strand)

3'CUAGAU 5' mRNA               5'GAUCUCG 3'
                               antisense RNA
```

Genetic constructs designed for gene silencing may also include an inverted repeat. An 'Inverted repeat' is a sequence that is repeated where the second half of the repeat is in the complementary strand, e.g.,

```
5'-GATCTA...TAGATC-3'

3'-CTAGAT...ATCTAG-5'
```

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polypeptides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3'-UTR sequence, or the corresponding gene.

Other gene silencing strategies include dominant negative approaches and the use of ribozyme constructs (McIntyre, 1996, Transgenic Res, 5, 257).

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); apple (Yao et al., 1995, Plant Cell Reports 14, 407-412); maize (U.S. Pat. Nos. 5,177,010 and 5,981,840); wheat (Ortiz et al., 1996, Plant Cell Rep. 15, 1996, 877); tomato (U.S. Pat. No. 5,159,135); potato (Kumar et al., 1996 Plant J. 9, 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416, 011; 5,569,834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037,522); *brassica* (U.S. Pat. Nos. 5,188,958; 5,463, 174 and 5,750,871); cereals (U.S. Pat. No. 6,074,877); pear (Matsuda et al., 2005, Plant Cell Rep. 24(1):45-51); *Prunus* (Ramesh et al., 2006 Plant Cell Rep. 25(8):821-8; Song and Sink 2005 *Plant Cell Rep.* 2006; 25(2):117-23; Gonzalez Padilla et al., 2003 Plant Cell Rep. 22(1):38-45); strawberry (Oosumi et al., 2006 Planta. 223(6):1219-30; Folta et al., 2006 Planta April 14; PMID: 16614818), rose (Li et al., 2003), *Rubus* (Graham et al., 1995 Methods Mol Biol. 1995; 44:129-33), tomato (Dan et al., 2006, Plant Cell Reports V25:432-441), apple (Yao et al., 1995, *Plant Cell Rep.* 14, 407-412) and *Actinidia eriantha* (Wang et al., 2006, Plant Cell Rep. 25, 5: 425-31). Transformation of other species is also contemplated by the invention. Suitable methods and protocols are available in the scientific literature.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods for Modifying Endogenous DNA Sequences in Plant

Methods for modifying endogenous genomic DNA sequences in plants are known to those skilled in the art. Such methods may involve the use of sequence-specific nucleases that generate targeted double-stranded DNA breaks in genes of interest. Examples of such methods for use in plants include: zinc finger nucleases (Curtin et al., 2011. Plant Physiol. 156:466-473.; Sander, et al., 2011. Nat. Methods 8:67-69.), transcription activator-like effector nucleases or "TALENs" (Cermak et al., 2011, Nucleic Acids Res. 39:e82; Mahfouz et al., 2011 Proc. Natl. Acad. Sci. USA 108:2623-2628; Li et al., 2012 Nat. Biotechnol. 30:390-392), and LAGLIDADG homing endonucleases, also termed "meganucleases" (Tzfira et al., 2012. Plant Biotechnol. J. 10:373-389).

In certain embodiments of the invention, one of these technologies (e.g. TALENs or a Zinc finger nuclease) can be used to modify one or more base pairs in the uORF in order to disable it, so it is no longer translatable.

In one embodiment the first base pair of the ACG start codon is changed to TCG to accomplish this. This would inactivate the ascorbate feed back regulation of GGP translation and allow increases of ascorbate concentration in the plant.

Alternatively, a codon for a highly conserved amino acid in the uORF can be changed to stop the uORF from functioning in down regulating translation of the GGP at high ascorbate. For example a His residue in the conserved region of the uORF can be changed to a Leu.

In a further embodiment an early base pair in the uORF is altered to introduce a stop codon, and cause early termination of the uORF which stops ascorbate feedback regulation of the translation of GGP.

Those skilled in the art will thus appreciate that there are numerous ways in which the uORF can be disrupted to remove negative regulation by ascorbate and to increase ascorbate production. Any such method is included within the scope of the invention.

Plants

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either self-ed or crossed with a different plant strain and the resulting off-spring from two or more generations also form an aspect of the present invention, provided they maintain the transgene or modification of the invention.

Methods for Extracting and Measuring Ascorbate from Plants

Methods are also provided for the production of ascorbate by extraction of ascorbate from a plant of the invention. Ascorbate may be extracted from plants as follows:

Frozen tissue samples are ground to a fine powder in a Cryomill at liquid nitrogen temperature. About 200 mg of frozen powdered tissue is then suspended in 5 volumes of 7% metaphosphoric acid containing 2 mM TCEP (Pierce), vortexed for 20 sec and incubated in a heating block for 2 h at 40° C. TCEP Is used in the extraction solution, because it is more effective reducing agent under acidic conditions than DTT, ensuring that all of vitamin C is in the ascorbic acid reduced form. The extract is centrifuged at 4° C. and twenty µL of the supernatant is injected into a Rocket Column And eluted using two solvents A (0.28% o-phosphoric acid, 0.1 mM EDTA and 0.25% methanol) and B (acetonitrile). Ascorbate and other compounds were eluted using a 5-min gradient to 90% B. Standards were run with every batch or 20 samples processed. Ascorbate was calculated from the area under the absorption at 240 nm curve at ~1 minute of elution.

This method may be up-scaled for larger scale ascorbate extraction using approaches well-known to those skilled in the art.

This invention may also be said broadly to consist in the parts, elements and features referred to or indicated in the specification of the application, Individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which:

FIG. 10 shows an alignment of the predicted peptide sequences of the ACG uORF in the 5'-UTR of GGP over a wide range of species. Alignment was done using Clustal X (Thompson et al., *Nucleic Acids Res* 25, 4876 (1997).) as executed by Vector NTI. The suffixes are as listed in FIG. 7 with the addition of plants outside the dicotyledonous plants. Cr, *Chlamydomonas rheinhardtii*; Pp, *Physcomitrella patens*; Ps, *Picea sitchensis*; Sm, *Selaginella moellendorffi*; Zm, *Zea mays*. The prefix before each name is the GenBank accession number. Also shown is the consensus sequence for the whole uORF. Further highlighted underlined is a highly conserved consensus motif NPSPHGGRGALPSEGGSPS-DLLFLAGGG (SEQ ID NO: 108).

FIG. 15 shows sequences of 5'UTRs for GGP genes from potato, tomato and apple. The uORF is shown in bold.

EXAMPLES

The invention will now be illustrated with reference to the following non-limiting example.

It is not the intention to limit the scope of the invention to the abovementioned example only. As would be appreciated by a skilled person in the art, many variations are possible without departing from the scope of the invention.

Example 1

Elucidation of the Control of GGP Expression

Summary

Ascorbate (vitamin C) Is an essential antioxidant and enzyme co-factor in both plants and animals. Ascorbate concentration is tightly regulated in plants, partly to respond to stress. The applicants have shown that ascorbate levels are controlled via the post-transcriptional repression of GDP-L-galactose phosphorylase (GGP), the rate-limiting enzyme in the ascorbate biosynthesis pathway. This regulation requires the translation of a Cis-acting uORF (upstream open reading frame), which initiates from a non-canonical start codon and represses the translation of the downstream GGP ORF under high ascorbate. Removal of this uORF allows plants to produce high levels of ascorbate. The uORF is present in the GGP gene from both lower and higher plants indicating it is an ancient mechanism to control ascorbate levels.

Ascorbate (vitamin C) is an essential biochemical found in most living organisms with a central role of controlling the redox potential of the cell (Asensi-Fabado et al., 2010, *Trends Plant Sci.* 15, 582; Foyer et al., *Plant Physiol.* 155, 2 (2011)) as well as serving as an enzyme cofactor (Mandl et al., 2009, *Br. J. Pharmacol.* 157, 1097). Ascorbate concentrations are regulated according to demand; for example, leaf ascorbate concentrations increase under high light intensities when the need for ascorbate is greatest (Bartoli et al., 2006, *J. Exp. Bot.* 57, 1621; Gatzek et al., 2002, *Plant J.* 30, 541). However the mechanism by which ascorbate biosynthesis is regulated is not known. The applicants have shown previously that the enzyme GDP L-Galactose phosphorylase (GGP) is central to determining ascorbate in plants (Bulley et al., 2012, *Plant Biotechnol J* 10, 390; Bulley et al., 2009, *J. Exp. Bot.* 60, 765), suggesting it may serve a regulatory role.

Results and Discussion

Figure 1:
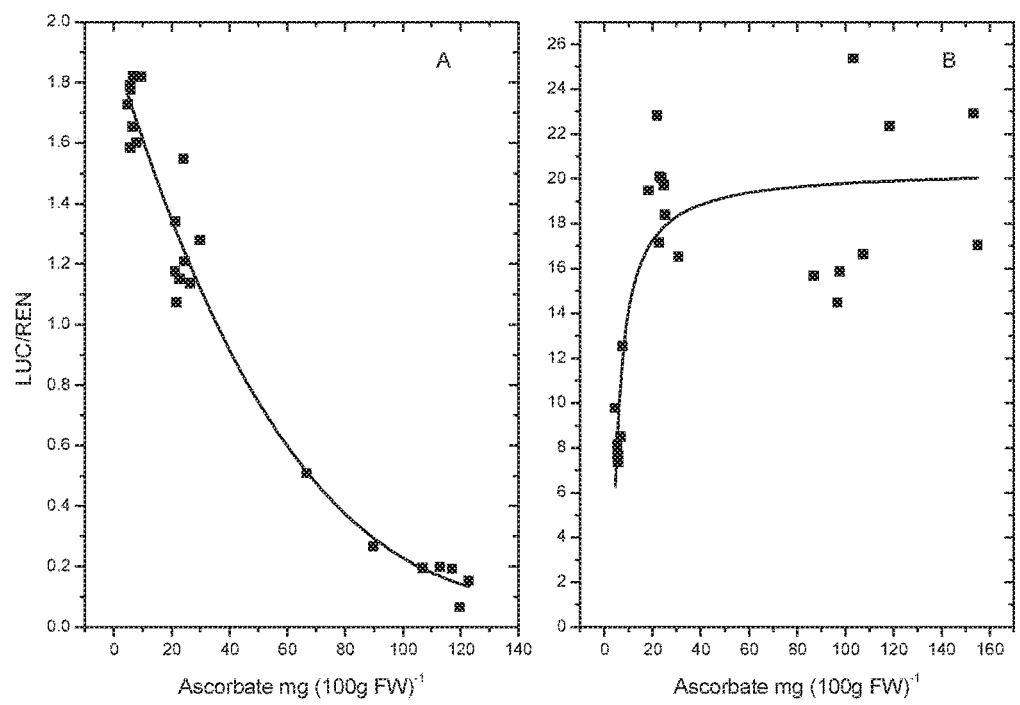
FIG. 1 shows the effect of ascorbate on reporter gene activity driven by the GGP promoter or by a control promoter. A, LUC/REN ratio as a function of leaf ascorbate concentration for GGP promoter B, LUC/REN ratio as a function of leaf ascorbate concentration for TT8 promoter. ▲low ascorbate (KO) leaves, ■ control leaves, ○ high ascorbate (GGP) leaves.
Figure 4:
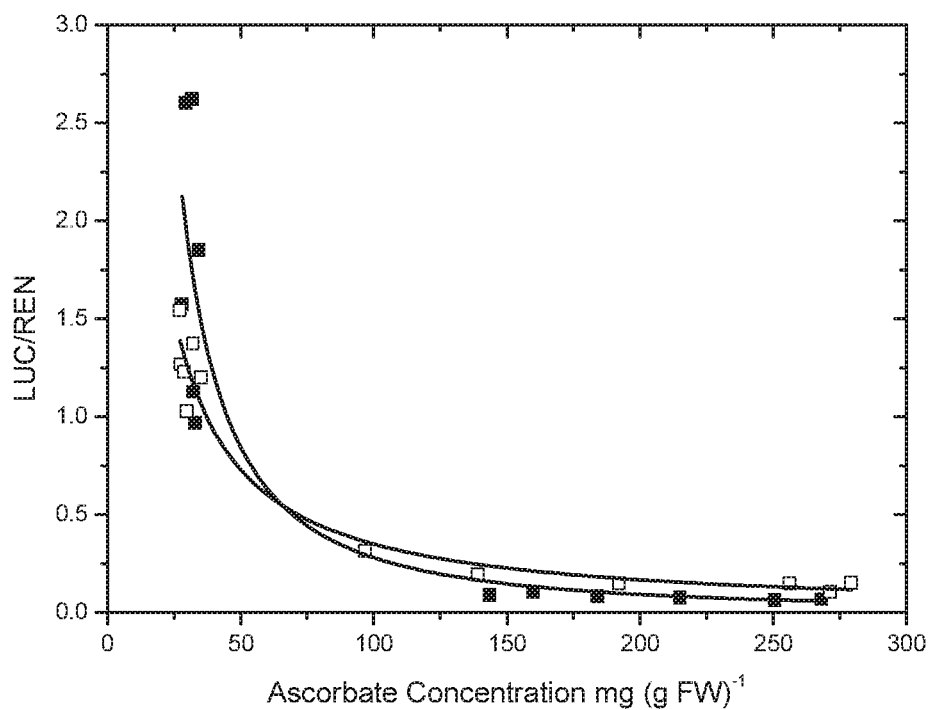
FIG. 4 shows a comparison of the response of the reporter gene to ascorbate for GGP full promoter constructs from kiwifruit and *Arabidopsis*. GGP was used to raise ascorbate levels as in FIG. 1. ■ *Arabidopsis* GGP (promoter and 5'-UTR), a standard kiwifruit GGP (promoter and 5'-UTR). Other details are found in the methods section.

To investigate if the GGP gene is regulated by ascorbate levels, the applicants fused the kiwifruit GGP promoter with its 5'-UTR (SEQ ID NO: 101) to the luciferase (LUC) reporter gene and expressed the construct transiently in *Nicotiana benthamiana* leaves. (Hellens et al., 2005, *Plant Methods* 1, 13.). The applicants manipulated ascorbate by also expressing just the coding sequence of GGP under a strong constitutive promoter. A doubling of ascorbate concentration from ~2 mM (20 mg/100 g FW) to 4 mM was sufficient to reduce the relative LUC activity by 50%, and when ascorbate was increased close to 10 mM, >90% of LUC activity was abolished (FIG. 1). Similarly, the *Arabi-* dopsis GGP (VTC2; At4g26850) promoter and 5'-UTR (SEQ ID NO: 102) also conferred ascorbate dependent repression on a LUC reporter gene (FIG. 4).

Figure 5:
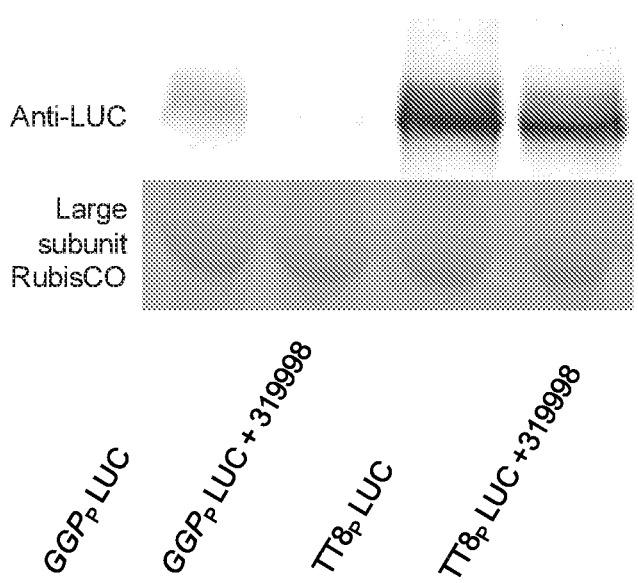
FIG. 5 shows the effect of high ascorbate concentration of the amount of LUC protein as measured by an anti-LUC antibody in transiently transformed tobacco leaves driven by either the GGP promoter or the control TT8 promoter. Experiments were carried out as described in FIG. 1. The ascorbate concentration in the +319998 (GGP) lanes was 55 to 63 mg/100 g FW while in the lanes without GGP it was 21 mg/100 g FW. Other details are found in the methods section.

In contrast, high ascorbate had no affect on relative LUC activity using a control promoter for a gene unrelated to ascorbate metabolism (T-8: an *Arabidopsis* bHLH transcription factor controlling polyphenolic biosynthesis) (FIG. 1). Additional controls demonstrate that this regulation was specific to GGP sequences, independent of the level of expression of the transgenes and was reflected in LUC protein changes (Tables 1-3, FIG. 5).

TABLE 1

The absolute value of LUC or REN does not significantly influence the LUC/REN ratio. The relationship between LUC and REN was linear over a 200 fold range. The subscript P refers to the whole promoter including any 5'-UTR from that gene. Other details are found in the methods section.

| Construct | Agrobacterium culture dilution as a % | Slope of relationship between LUC and REN | LUC/REN | Mean LUC Luminescent units +/− Standard Error | Mean REN Luminescent units +/− Standard Error |
|---|---|---|---|---|---|
| $GGP_P$ | 100 | 0.07 | 0.11 | 7442 ± 785 | 67908 ± 7429 |
| $GGP_P$ | 10 | 0.12 | 0.11 | 2777 ± 277 | 25001 ± 1684 |
| $TT8_P$ | 100 | 2.66 | 2.96 | 122573 ± 15748 | 41478 ± 4557 |
| $TT8_P$ | 10 | 2.64 | 2.91 | 25560 ± 2255 | 8786 ± 710 |
| $TT8_P$ | 8 | 2.97 | 2.69 | 23621 ± 2672 | 8785 ± 552 |
| $TT8_P$ | 5 | 1.56 | 2.24 | 10176 ± 547 | 4537 ± 210 |
| $TT8_P$ | 3 | 1.72 | 2.40 | 6412 ± 450 | 2676 ± 172 |
| $TT8_P$ | 1 | 2.39 | 2.49 | 1739 ± 274 | 699 ± 101 |
| $TT8_P$ | 0.5 | 2.53 | 2.79 | 1482 ± 175 | 531 ± 43 |

TABLE 2

Comparison of the effect of ascorbate on a range of control genes.

| Treatment | ascorbate mg/100 g FW Ascorbate mg/100 g FW | LUC/REN LUC/REN | Std error Std error | N N | | Slope of LUC REN slope |
|---|---|---|---|---|---|---|
| $TT8_P$ | 22 | 1.95 | 0.24 | 6 | a | 1.89 |
| $TT8_P$ + GGP | 78 | 4.09 | 0.28 | 12 | b | 4.71 |
| $EF1a_P$ | 23 | 0.767 | 0.086 | 6 | a | 0.780 |
| $ET1a_P$ + GGP | 82 | 0.733 | 0.065 | 12 | a | 0.775 |
| $ACt2_P$ | 24 | 0.385 | 0.042 | 6 | a | 0.327 |
| $ACt2_P$ + GGP | 82 | 0.550 | 0.074 | 12 | a | 0.586 |
| $ACt7_P$ | 22 | 0.815 | 0.037 | 6 | a | 0.757 |
| $ACt7_P$ + GGP | 78 | 0.843 | 0.036 | 12 | a | 0.834 |

+ GGP refers to the cotransformation of the CDS of the GGP from kiwifruit (Genbank accession FG528585) under the control of the 35S promoter in order to raise ascorbate. The slope of LUC REN is the slope of the plot of LUC values against REN values forced through the origin as a comparison to the LUC/REN ratios. N is the number of independent LUC/REN ratios measured. The subscript P refers to the whole promoter including any 51-UTR from that gene. Within a block of two rows, LUC/REN means with the same letter do not significantly differ at p < 0.01. Other details are found in the methods section.

TABLE 3

Effect of adding a control gene to the gene used to manipulate ascorbate concentration.

| $GGP_P$ | 22 | 0.251 | 0.027 | 12 | a | 0.230 |
|---|---|---|---|---|---|---|
| $GGP_P$ + GGP | 65 | 0.028 | 0.008 | 12 | b | 0.022 |
| $GGP_P$ + FG429343 | 22 | 0.226 | 0.044 | 12 | a | 0.183 |
| $TT8_P$ | 25 | 3.87 | 0.44 | 12 | a | 3.12 |
| $TT8_P$ + GGP | 50 | 2.42 | 0.21 | 12 | b | 2.25 |
| $TT8_P$ + FG429343 | 25 | 2.73 | 0.16 | 12 | b | 3.06 |

TABLE 3-continued

Effect of adding a control gene to the gene used to manipulate ascorbate concentration.

To check that expression of an extra gene (GGP) to increase ascorbate did not directly affect the LUC/REN ratio, we substituted another control gene, GenBank accession FG429343, an Actinidia deliciosa methyl transferase which had no direct affect of the ascorbate concentration. The subscript P refers to the whole promoter. Within a block of three rows, LUC/REN means with the same letter do not significantly differ at p < 0.01. Other details are found in the methods section.

Figure 6:
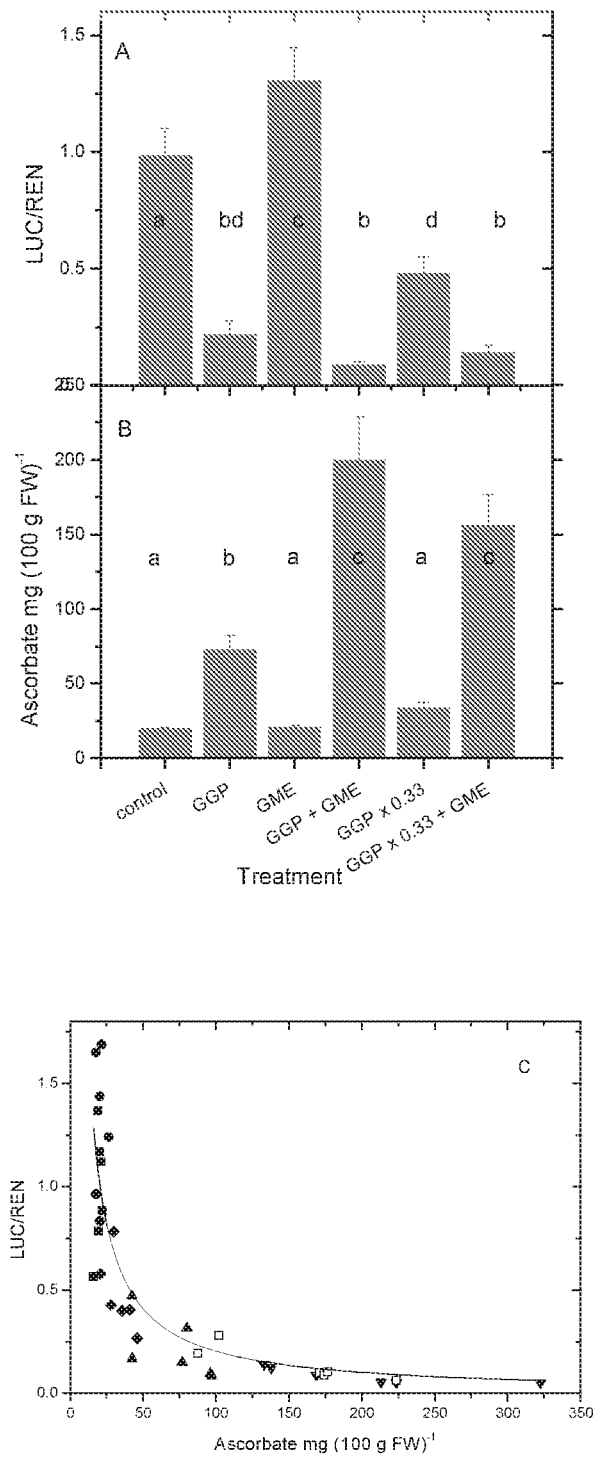
FIG. 6 shows the effect of manipulating ascorbate concentration independent of the GGP enzyme used to increase the leaf ascorbate by using GME to further enhance ascorbate at variable levels of GGP. A the effect of different combinations of GGP and GME on the LUC/REN ratio, B the effect of different combinations of GGP and GME on the ascorbate concentration. In A and B columns with the same letters are not significantly different at the 5% level. C the relationship between the individual leaf LUC/REN ratios and leaf ascorbate. Other details are found in the methods section. In C, ■, control; •, GME; ♦, 0.33×GGP; ▲, 1×GGP; □, 0.33×GGP+1×GME; ▼, 1×GGP+GME. 1 and 0.33 refer to relative amounts of GGP and GME Injected into the leaf.

In the experiments described, leaf ascorbate was manipulated through changes in expression of the GGP coding sequence. In order to separate the effects of ascorbate from possible effect of the GGP protein (Müller-Moulé, P., 2008, *Plant Mol. Biol.* 68, 31), the applicants expressed both GGP and GME separately and together. The applicants have previously shown (Bulley et al., 2009, *J. Exp. Bot.* 60, 765.) that GGP expressed alone in tobacco has a moderate effect, GME very little effect, whereas when expressed together there is a strong synergistic stimulation of ascorbate concentration. Thus by varying the ratios of these two genes, ascorbate can be manipulated independently of the amount of GGP protein (FIG. 6). The response of the ratio to ascorbate followed a smooth curve in spite of different levels of GGP protein associated with different ascorbate concentrations (FIG. 6), showing ascorbate or a related metabolite is the factor reducing the LUC activity.

Figure 7:
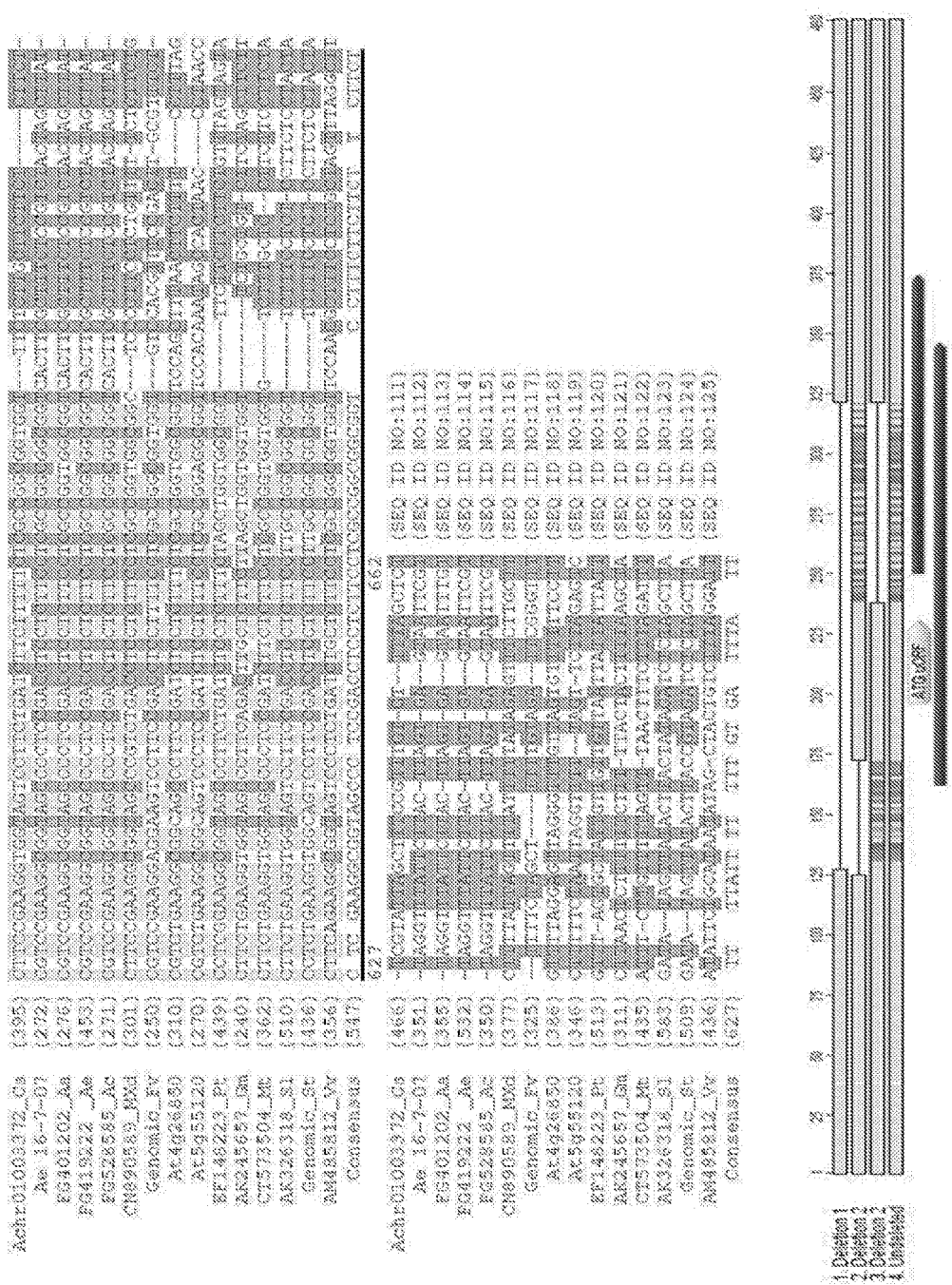
FIG. 7 shows an alignment of 5'-UTR sequences from a range of dicotyledonous species. Alignment was done using Clustal X as executed by Vector NTI. The suffix letters code species that the 5'-UTR sequences came from: Aa is *Actinidia arguta*, Ae is *A. eriantha* and Ac is *A. Chinensis*, MXd is *Malus×domestica*, Fv is *Fragaria vesca*, Sl is *Solanum lycospersicum*, St, is *Solanum tuberosum*, Vv is *Vitis vinifera*, Gm is *Glycine max*, Mt is *Medicago truncatula*, Pt is *Populus trichocarpa*, Cs is *Cucumis sativus*. The prefix before each name is the GenBank accession number. The two genomic sequences came from published resources (T. P. G. S. Consortium, 2011 Nature 475, 189); Velasco et al., 2010 Nat Genet 42, 833). The short uORF beginning with ATG is in bold while the highly conserved non-canonical uORF starting with ACG is underlined in bold (ACG1). The bracketed number of each sequence refers to the total length of its 5'-UTR. The lower schematic shows the highly conserved region of the 5'-UTR and the three deletions used in testing their functions. The colored regions are the highly conserved regions that were deleted either individually (deletion 2 and 3 from left to right) or in their entirety (deletion 1). The yellow motif is a small conserved uORF that starts with ATG (ATG1), while the orange motifs are two non-canonical uORFs that start with ACG (ACG1, bottom, ACG2 top). All three uORFs are conserved between species although ACG2 is less conserved at the protein level (~40 to ~60% Identical between families) compared to ACG1 (~60 to ~80%)
Figure 8:
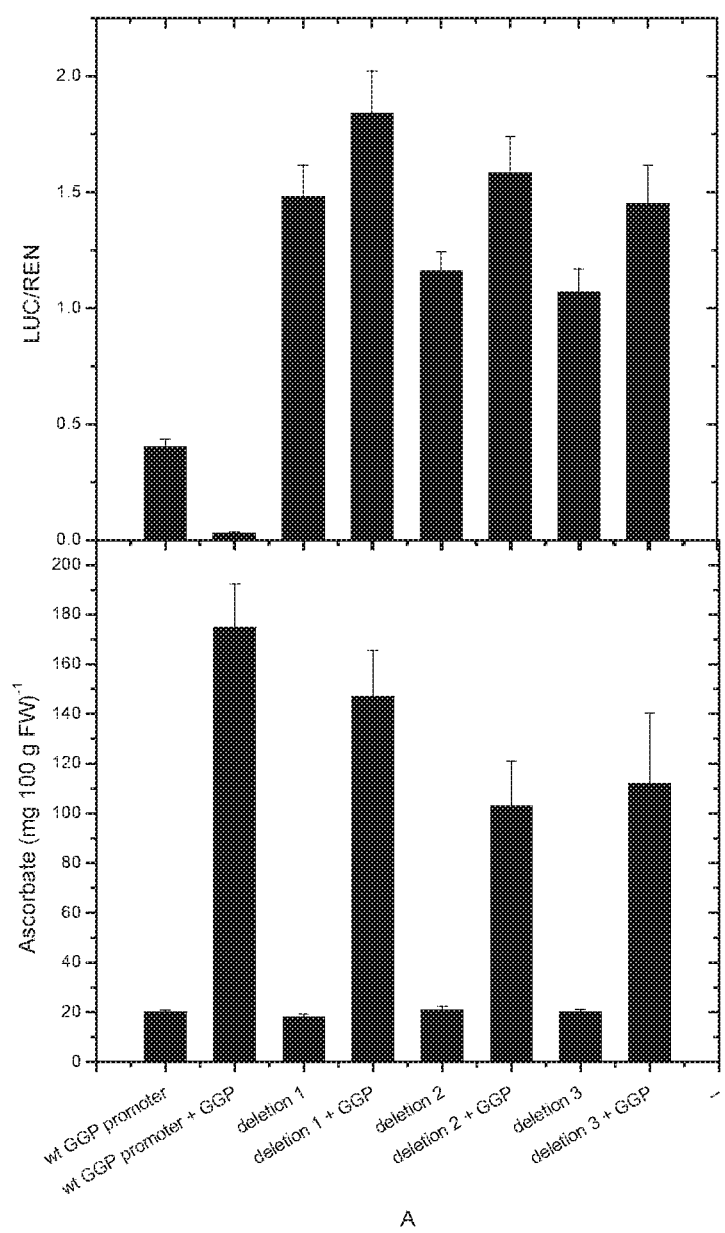
FIG. 8 shows the effect of deletions in the 5'-UTR region of the GGP gene on the down regulation of the promoter by ascorbate. Deletions are as labeled FIG. S4. The bottom graph shows the corresponding ascorbate concentrations in the same leaf as the LUC/REN ratios were measured. Bars represent standard errors.

To test whether the effect of ascorbate was mediated by the untranscribed promoter or the 5'-UTR the applicants undertook two experiments. Firstly the applicants swapped the 5'-UTR regions between the GGP TT8 promoters. We transiently expressed these in leaves and measured the relative LUC activity. Increased ascorbate reduced the LUC activity only when the 5'-UTR from GGP was present. (Table 4). Secondly the applicants deleted two regions within the 5'-UTR that were especially strongly conserved at the DNA level between species. The first was from ~387 to ~432 bp and the second between ~514b and ~597 bp (FIG. 7) with the rest of the GGP promoter intact, and tested them using the reporter assay. All deletions caused the loss of the ability of ascorbate to down regulate the reporter gene expression (FIG. 8). These experiments show that the 5'-UTR is necessary and sufficient for down regulation by ascorbate.

TABLE 4

| Treatment | ascorbate mg/100 g FW | LUC/REN | Std Error | N | | Slope of LUC REN |
|---|---|---|---|---|---|---|
| $TT8_{P'}$ – $GGP_{UTR}$ | 22 | 0.057 | 0.008 | 12 | a | 0.044 |
| $TT8_{P'}$ – $GGP_{UTR}$ + GGP | 66 | 0.007 | 0.001 | 12 | b | 0.0063 |
| $TT8_{P'}$ – $GGP_{UTR}$ + FG429343 | 24 | 0.041 | 0.002 | 12 | a | 0.041 |
| $GGP_{P'}$ – $TT8_{UTR}$ | 18 | 0.861 | 0.112 | 12 | a | 0.753 |
| $GGP_{P'}$ – $TT8_{UTR}$ + GGP | 72 | 0.479 | 0.027 | 12 | b | 0.441 |
| $GGP_{P'}$ – $TT8_{UTR}$ + FG429343 | 22 | 0.553 | 0.085 | 12 | b | 0.492 |

The ascorbate down regulation of the GGP promoter is expressed through the 5'-UTR region of the gene. Subscript UTR refers to the 5'-UTR of the gene and subscript P' refers to just the untranscribed promoter of the respective gene. GGP refers to the cotransformation of the CDS of GGP under the control of the 35S promoter in order to raise ascorbate levels while FG429343, is a methyl transferase control gene. The slope of LUC REN is the slope of the plot of LUC values against REN values forced through the origin. N is the number of independent LUC/REN ratios measured. Within a block of three rows, LUC/REN means with the same letter do not significantly differ at p < 0.01. Other details are found in the methods section.

To investigate whether the ascorbate control is at the transcriptional or post-transcriptional level, the applicants measured transcript levels of the reporter gene construct. Our data show little effect of ascorbate on the levels of LUC mRNA (Table 5), indicating that ascorbate, directly or indirectly, acts through the 5'-UTR to control the translation of GGP.

TABLE 5

Effect of ascorbate level on the RNA levels for LUC driven either by the GGP promoter or TT8, a control gene. Gene expression was measured relative to the expression of REN in the same RNA preparation. Values are the mean of three biological replicates, each involving three combined leaves. Standard errors are shown brackets. Within each promoter pair, there was no significant difference in gene expression or the LUC activity for the TT8 promoter. The change in LUC activity for the GGP promoter was significant (p < 0.001) as were the changes in ascorbate for both promoters (p < 0.003).

| Promoter/Treatment | Gene expression | LUC/REN | Ascorbate mg/100 g FW |
|---|---|---|---|
| GGP/low ascorbate | 6.0E-02 ± 8.8E-03 | 1.08 ± 0.05 | 25.3 ± 0.93 |
| GGP/high ascorbate | 5.3E-02 ± 7.4E-03 | 0.15 ± 0.03 | 92.4 ± 7.1 |
| TT8/low ascorbate | 8.5E-01 ± 5.7E-02 | 19.9 ± 0.59 | 26.1 ± 6.3 |
| TT8/high ascorbate | 9.3E-01 ± 1.1E-01 | 16.3 ± 0.83 | 84.6 ± 4.7 |

Figure 9:
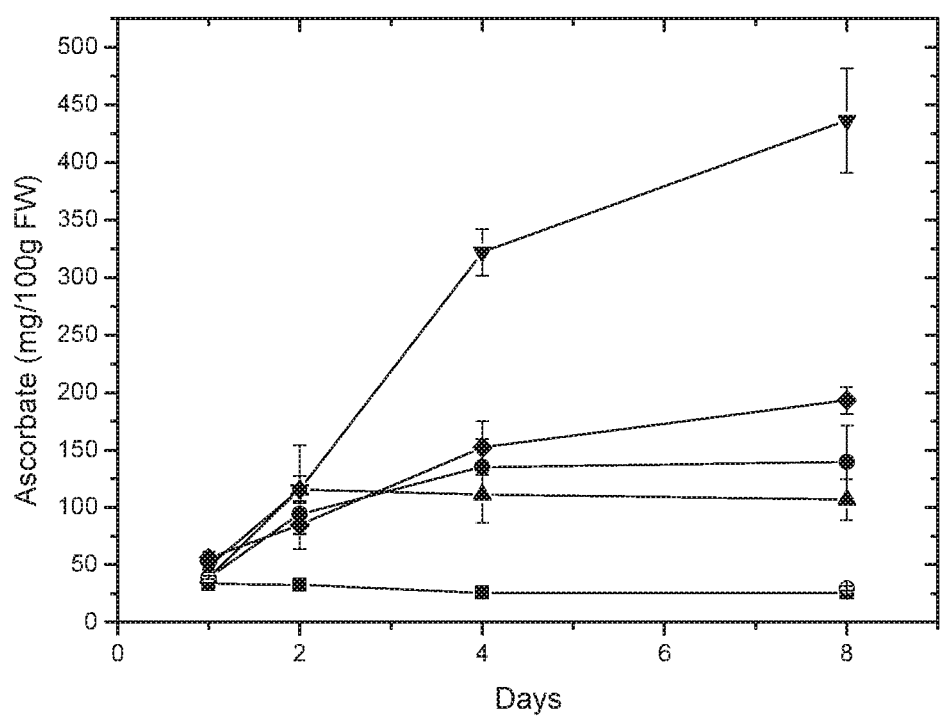
FIG. 9 shows a time course of the effect of the presence or absence of the 5'-UTR in front of the GGP CDS on leaf ascorbate. Both constructs were driven by the 35S promoter. Other details are found in the methods section. U, control (P19 only); •, -5'-UTR GGP; ▲, +5'-UTR GGP; ▼, -5'-UTR GGP+GME; ♦, +5'-UTR GGP; ○, GME.

To verify that the 5'-UTR acts directly to affect leaf ascorbate concentrations, we constructed a 35S driven GGP coding sequence with and without the GGP 5'-UTR in front of the coding sequence. Both constructs enhanced leaf ascorbate in the transient system, but the construct without the 5'-UTR had about 30% more ascorbate than the construct with the 5'-UTR (FIG. 9). Furthermore, co-infiltrating GME into the leaf so to drive the ascorbate even higher than GGP alone (Bulley et al., 2009, J. Exp. Bot. 60, 765.) resulted in over two-fold higher ascorbate in the construct without the 5'-UTR than the construct containing the 5'-UTR. Thus, in high ascorbate conditions the GGP 5'-UTR limits both GGP production and ascorbate synthesis. Removal of this regulation provides a way of generate plants with high ascorbate levels.

Figure 2:
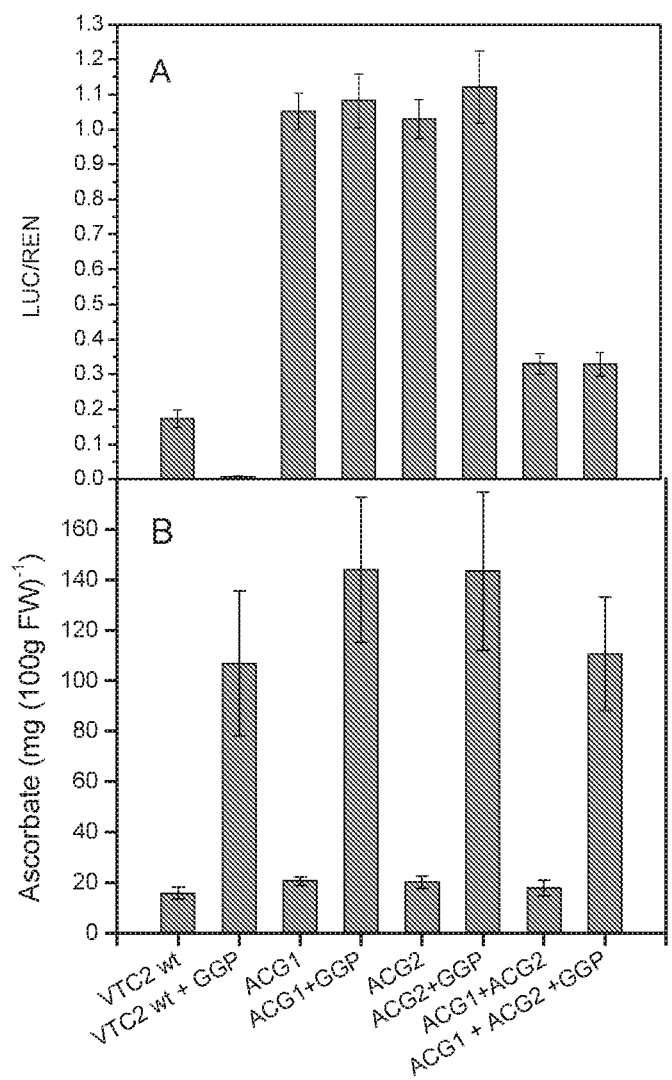
FIG. 2 shows the effect of ascorbate on the GGP promoter strength in various changed forms of the ACG uORFs present in the 5'-UTR of the GGP gene (FIG. S7B). A. LUC/REN ratios, B. Ascorbate concentrations in the same treatments. VTC2 is the wild type 5'-UTR and promoter of GGP. ACG1 had the initiating ACG of ACG1 changed to a TCG to no longer make it a start codon. ACG2 had the first His in a highly conserved region of the uORF (FIG. S5, S7B) changed to a Leu. GGP was added to manipulate the ascorbate concentrations. In A, the treatment VTC2+GGP had a significantly lower LUC/REN value than all other treatments (p=0.001), which were not significantly different. In B, The addition of GGP to the leaves increased ascorbate significantly (p=0.001), but differences between treatments were not significant at either high or low ascorbate. The bars are standard errors, n=4.
Figure 11:
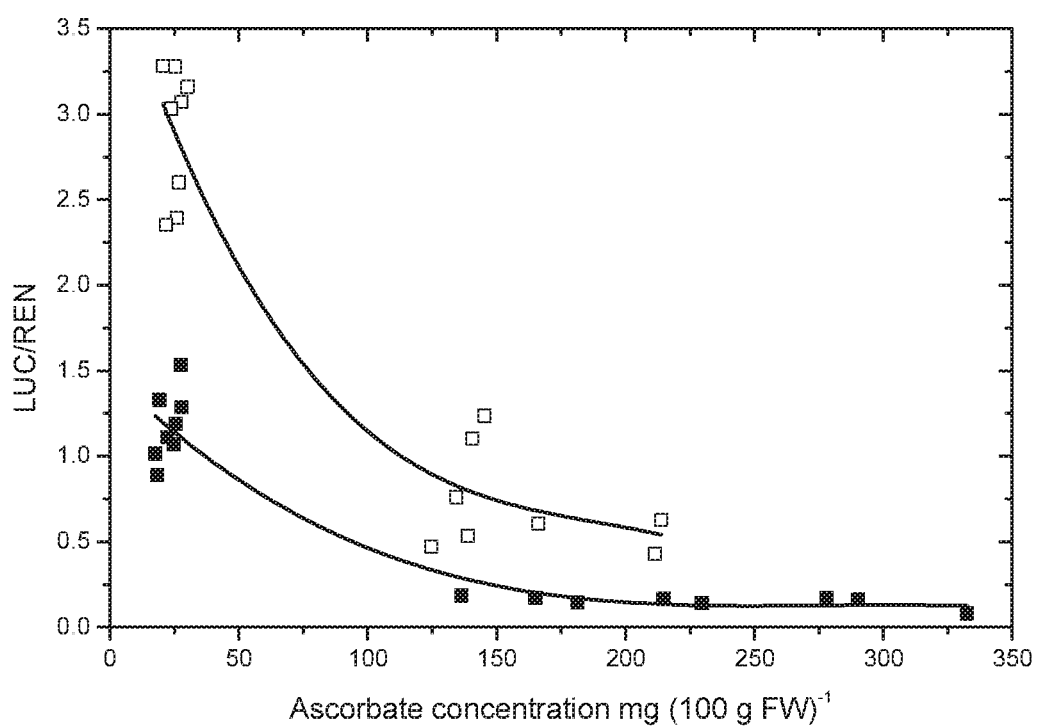
FIG. 11 shows the effect of the small ATG uORF on the response of reporter gene activity driven by the GGP promoter and 5'-UTR to ascorbate concentration. The start codon in the small 30 bp ORF in the 5'-UTR was inactivated by converting the start ATG to a TTG. □, inactivated uORF; ■, uORF start codon present. In this experiment and in a replicate experiment the reporter gene activity from the 5'-UTR without the start codon was more highly expressed at both low and high ascorbate than the gene with the uORF Intact. The solid lines are polynomial fits to the data. Other details are found in the methods section.

Given that the effect of ascorbate was mediated through the 5'-UTR region of GGP, we examined the properties of the 5'-UTR. GGP is unusual in having a long 5'-UTR, over 500 bp long in many species with strongly conserved elements (FIG. 7). Aligned GGP 5'-UTRs from different species including an algae and two mosses revealed the presence of a highly conserved uORF with the potential to encode a 60 to 65 amino acid peptide (FIG. 10). Interestingly, for this peptide to be made, translation would need to initiate at a non-canonical ACG initiation codon. A few examples of non-canonical translation initiation have been described (Ivanov et al., 2008, Proc. Natl. Acad. Sci. USA 105, 10079). Efficient translation requires Kozak sequences which is the case for this ORF (FIG. 8). To test if this uORF is required for ascorbate dependent regulation of the GGP gene, the applicants mutated the potential ACG initiation codon to TCG. LUC activity from the mutated construct remained high, even in the presence of high ascorbate (FIG. 2). To further examine the requirement of the uORF, the applicants mutated a highly conserved His (CGG codon) at residue 36 to Leu (CTG). Again, this abolished ascorbate dependent regulation (FIG. 2). Mutating an internal ATG codon with potential to encode a short uORF of 10 amino acids, increased the relative LUC activity by over two fold, probably because it removed a competing start codon, but did not change the relative sensitivity of the promoter to ascorbate concentration (FIG. 11).

Figure 3:
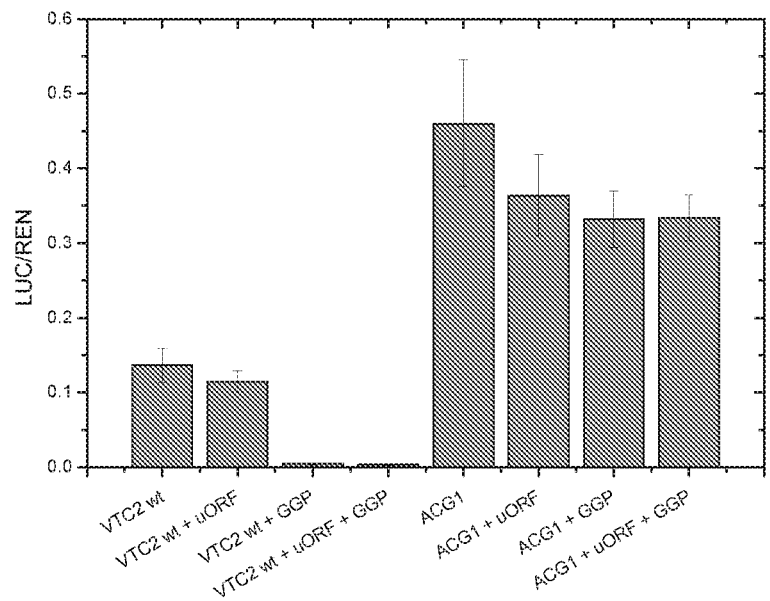
FIG. 3 shows the results of testing whether the non canonical uORF in the 5'-UTR of GGP acts in a cis or trans manner. VTC2 wt refers to the ascorbate repressed promoter and 5'-UTR, ACG1 refers to the mutated ACG codon of the uORF (non-responding), uORF is addition of the uORF driven by a 35S promoter and GGP is addition of the GGP coding sequence also driven by 35S to raise ascorbate.

The applicants then used the ACG uORF mutant that did not respond to ascorbate to test whether the predicted uORF worked in a Cis or Trans configuration. The applicants tested whether expressing the ACG uORF separately could recover ascorbate repression of LUC activity in this mutated vector. In FIG. 3 the applicants show that the presence of the ACG uORF had no effect on any treatment and did not complement the mutant form of the ACG uORF. This is consistent with the uORF working in a Cis conformation with the GGP CDS.

In this work the applicants provide evidence that ascorbate, or a precursor of ascorbate, interacts either directly or indirectly through an intermediate with a peptide produced by a non canonical uORF in the 5'-UTR of GGP, the key control gene of ascorbate biosynthesis, resulting in inhibition of the translation of the GGP enzyme. Reports of the control of protein expression in eukaryotes by products of a biosynthesis pathway are rare. Often gene expression is controlled by signaling cascades via a separate receptor to a transcription factor or through posttranslational modification of the target proteins (Smeekens et al., 2010, Curr. Opin. Plant Biol. 13, 273). While it has been reported that 5'-UTR sequences are important in controlling protein expression (Hulzink et al., 2003, Plant Physiol. 132, 75), reports on the control by a small molecule of gene expression through the 5'-UTR of the mRNA In eukaryotes are uncommon (Rahmani et al., 2009, Plant Physiol. 150, 1356) and control through a non-canonical start codon uORF are extremely rare.

A simple model of action may be that the ACG uORF is translated but in the presence of high ascorbate, the ribosome is stalled on the uORF. At low ascorbate, the translation terminates at the stop codon and immediately restarts downstream at the start ATG of GGP. There is no obvious Kozak sequence associated with the GGP primary start codon, but a reasonably strong Kozak sequence associated with ACG1. This effectively primes the ribosome at high ascorbate on the GGP mRNA ready for translation to respond rapidly to any reduction in ascorbate due to stress.

It appears that another factor may be required for the action of this feed-back loop. This is because the ascorbate regulation of the 5'-UTR for GGP from A. eriantha, a kiwifruit species with very high fruit ascorbate (Bulley et al., 2009, J. Exp. Bot. 60, 765.), functions in N. benthamiana. For A. eriantha to have high ascorbate suggests a mutation has occurred disrupting the ascorbate feedback of GGP translation in A. eriantha. However, that control of the A. eriantha GGP by ascorbate is functional in N. benthamiana suggests a factor mediating between ascorbate and the ACG1 uORF Is functional in *N. benthamiana*. This factor is likely to be a protein.

There are two types of uORF (Tran et al., 2008. *BMC Genomics* 9, 361): sequence-independent uORFs, where translation of the uORF influences the reinitiation efficiency of a downstream ORF and thus affects overall translation (Calvo et al., 2009. *Proc. Natl. Acad. Sci. USA* 106, 7507) but the uORF-encoded peptide sequence is not important (the short ATG 10 amino acid uORF In the GGP 5'-UTR appears to fit into the class (FIG. 7), and sequence-dependent ORFs, where the nascent uORF peptide causes ribosome stalling during translational elongation and termination. The fact that the GGP uORF encodes a highly conserved peptide over a wide range of plant taxonomies and that ascorbate repression is abolished by a single amino acid mutation in the uORF, indicates the latter type. Two examples in plants, polyamine and sucrose regulation (Rahmani et al., 2009, *Plant Physiol.* 150, 1356; Gong and Pua, 2005, *Plant Physiol.* 138, 276) involve sequence dependent uORFs. Our new example is different in that it initiates translation with a highly conserved non-canonical codon.

In conclusion we have shown that the level of ascorbate in a leaf can be controlled through ascorbate feedback through a non canonical uORF in the long 5'-UTR of the controlling gene of ascorbate biosynthesis, GGP. We show evidence that this feedback acts post-transcriptionally by controlling the level of the GGP enzyme. We propose that this is a major mechanism that ascorbate concentrations are controlled in the L-galactose pathway of ascorbate biosynthesis.

Materials and Methods:

Plant Materials and Chemical Assays

Figure 12:
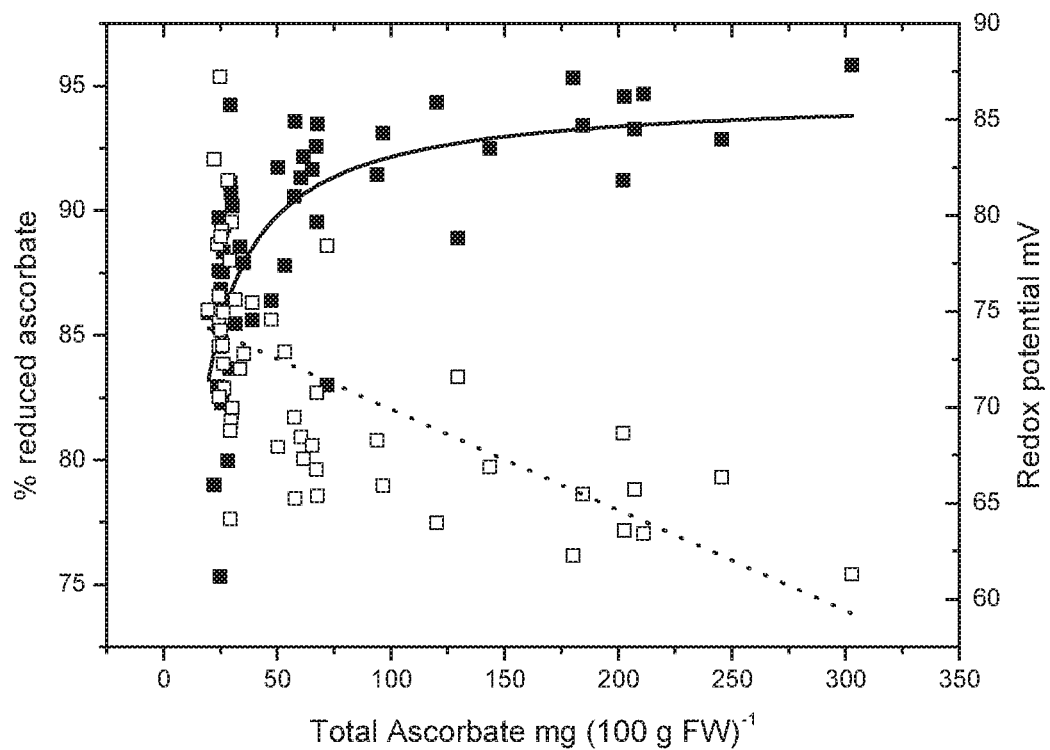
FIG. 12 shows the reduction state of ascorbate as a function of total leaf ascorbate. The data comes from three separate experiments. Ascorbate was manipulated using GGP and measured with and without reducing agent. When ascorbate concentrations were classified into low (27±0.7 mg/100 g FW), medium (59±2.7) and high (179±17.5) (mean±standard error) the values of redox potential were significantly different and decreased with increasing ascorbate from 74.8±1.0, 70.1±1.2 and 65.6±0.8 (p=0.05). The solid line is a hyperbolic fit to the % reduced data, and the dotted line is the linear fit to the redox potential.

The *Nicotiana benthamiana* leaf transient reporter gene system using luciferase (LUC) as the promoter specific reporter and renilla (REN) as the transformation reporter was as described previously (Hellens et al., 2005, *Plant Methods* 1, 13). Ascorbate concentration in the leaf was manipulated by co-injecting either the coding sequence for *Actinidia chinensis* GGP in pGreen (Hellens et al., 2000, *Plant Mol. Biol.* 42, 819) under the 35S promoter transformed into *Agrobacterium tumifaciens* (Bulley et al., 2009, *J. Exp. Bot.* 60, 765.) or a KO vector constructed using as a template the GGP sequence from *N. benthamiana* assembled from seven ESTs in GenBank as described by (Snowden et al., *The Plant Cell* 17, 746). In addition, the version of the CDS of *A. eriantha* GME (GenBank accession FG424114) described earlier (Bulley et al., 2009, *J. Exp. Bot.* 60, 765.) was used to synergistically enhance ascorbate with GGP. Ascorbate was measured in extracts of the same leaf using an HPLC based assay also as previously described (Rassam et al., 2005, *J. Agric. Food Chem.* 53, 2322). Ascorbate was measured as total ascorbate by reducing extracts before HPLC (Rassam et al., 2005, *J. Agric. Food Chem.* 53, 2322). Measurement of the redox state of the ascorbate found the redox potential decreased significantly with increased concentration of ascorbate (FIG. 12). This raises the possibility that the effect of ascorbate may be either through ascorbate itself or through the decreased redox potential at increased ascorbate.

Figure 13:
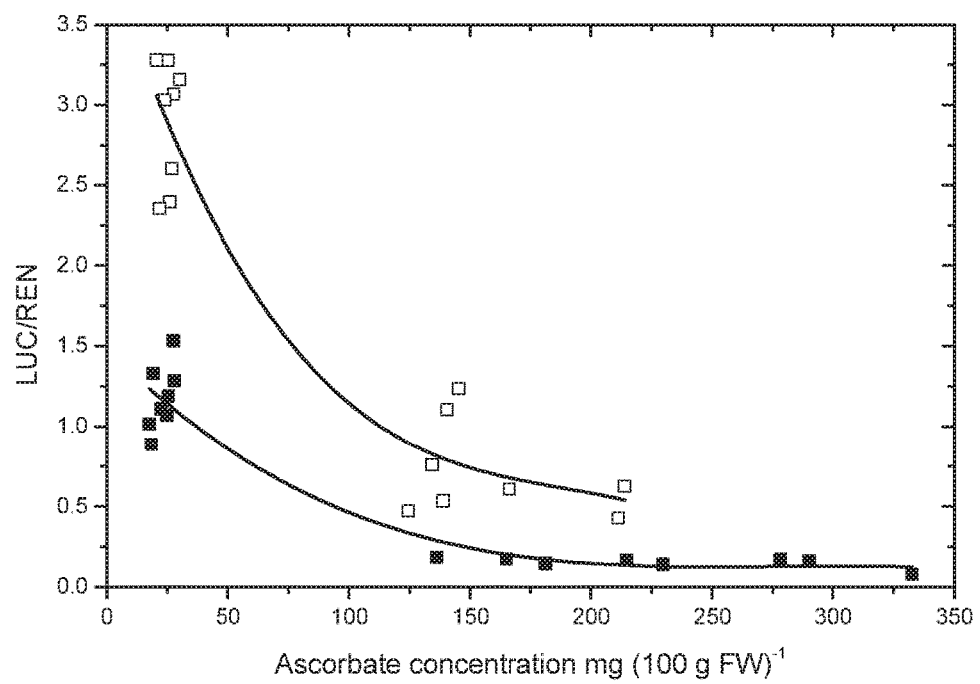
FIG. 13 shows the effect of ascorbate on reporter gene activity driven by the GGP promoter or by a control promoter. A, LUC activity versus REN activity for the GGP promoter; B, LUC activity versus REN activity for TT8 promoter. The three slopes in A are significantly different (p<0.001) while only the low ascorbate slope in B is significantly lower (p<0.001) than the other two lines which do not differ in slope significantly).

FIG. 13 shows a typical experiment where each point (mean of two to three measurements) represents a different leaf of *N. benthamiana* showing how ascorbate affects the LUC activity but has little effect on the REN activity. This data is also plotted in FIG. 1 where the mean LUC/REN ratio for each leaf is plotted against the ascorbate concentration.

To test whether the effect of ascorbate was mediated by the promoter or the 5'-UTR we constructed two vectors where the 5'-UTR regions were swapped between the GGP promoter and the TT8 promoter. The resulting constructs consisted of the TT8 core promoter (TT8P') followed by the GGP 5'-UTR (GGPUTR) and vice versa. We transiently expressed these in leaves and measured the relative LUC activity.

To test the effect of the 5'-UTR in front of the GGP coding sequence on ascorbate concentration, a different GGP gene (GenBank accession FG460629) was used instead of the GGP used in other experiments. At the protein level it was 96% identical to the standard GGP and in the absence of the 5'-UTR, raised ascorbate concentrations to similar levels seen for the usual GGP. The version with the 5'-UTR had the full 5'-UTR, while the version labeled without the UTR had all but 37 bp upstream of the start ATG deleted using the XhoI restriction enzyme. In this region at the 3' end of the 5'-UTR, there is little homology between GGPs (FIG. 8). Both versions were ligated into the pART277 vector (Gleave, A., 1992, *Plant Mol. Biol.* 20, 1203 (1992).

The amount of LUC protein was measured using an antibody to LUC (Promega) using a Western blot of 50 μg soluble cellular protein per lane (extracted in 40 mM phosphate buffer, pH 7.4, 150 mM NaCl) from various constructs transiently expressed in *Nicotiana benthamiana* leaves. The large subunit of RubisCO as stained by SYPRO Tangerine protein gel stain is shown as a loading control.

To separate the effects of GGP protein from ascorbate, we initially attempted to use ascorbate or its precursors injected directly into the leaf by syringe. However we could not get sustained changes in leaf ascorbate. We also tried allowing detached leaves or discs previously injected with *Agrobacterium* LUC/REN constructs to take up ascorbate precursors. While these leaves did have very significant increases in ascorbate, the leaves deteriorated before LUC/REN values could rise enough to be measurable. We then tried lowering ascorbate without lowering GGP concentrations by knocking out two genes involved in ascorbate biosynthesis (encoding galactose dehydrogenase and GDP mannose epimerase). However, again we failed to have significant changes in leaf ascorbate, suggesting that their expressed enzymes may be stable or in excess over the seven day extent of the experiment.

Experiments were repeated at least twice with similar results, and although in some cases the high ascorbate reduced REN expression as well as LUC, this did not alter the effect of ascorbate on reducing the slope of the relationship (i.e. the LUC/REN ratio) for the GGP promoter but not the TT8.

Gene Cloning and Plasmids

The GGP promoter from *Actinidia eriantha* (SEQ ID NO: 101) was cloned by genome walking and has been deposited in GenBank as accession number JX486682. *A. eriantha* gDNA (2.0 μg) was digested using seven blunt cutting restriction enzymes; DraI, EclII 136, EcoRV, HpaI, MScI, ScaI, SspI and StuI. Digests were purified and eluted in 10 μL using PCR Clean and Concentrate spin columns (Zymogen). Double stranded adapter sequences (Clontech) containing nested PCR primer sites were ligated onto cut fragments overnight at 16 C using T4 Rapid Ligase (Roche). Ligations were column purified a second time and eluted in 30 μL. First round PCR was performed using 1 uL of each digest with primers 319998NRWLK1, RPH-149 and Ex Taq polymerase (Takara) using the following two step cycling conditions. For the first high stringency step, one cycle of denaturation was performed at 94 C for two min, followed by seven cycles of 94 C for 25 sec and elongation/annealing at 72 C for three min. The second step consisted of 32 cycles of 94 C for 25 sec and 67 C for three min before a final 67 C extension for three min. The first round products were run on a 1% agarose gel and 1 µL of a 1:50 dilution was used as template for second round PCR with 319998NRWLK2 and RPH-150. Second round PCR was also performed as a two step PCR with an initial denaturation of 94 C for two min followed by five cycles of 94 C for 25 sec and 72 C for 3 m. This was followed by a further 20 cycles of 94 C for 25 s and 67 C for three min before a final 67 C extension. Gel electrophoresis was used to identify PCR products between 500-2 kb in size for cloning into pGem T Easy vector (Promega) according to the manufacturer's instructions. Clones were DNA sequenced confirmed for overlap with the known 5'-UTR. A second set of nested primers was designed to the end of the first promoter walk to extend the known *A. eriantha* promoter sequence to 2 kb. This 2 kb promoter sequence was then PCR amplified from *A. eriantha* gDNA using primers *Eriantha* gDNA PCR 5' and 319998NRWLK2 and sub-cloned into pGreen0800-5'_LUC (Hellens et al., 2000, *Plant Mol. Biol.* 42, 819) using EcoRV and NcoI restriction enzymes. The final construct is called the GGP-promoter-pGreenII 0800-5 LUC vector.

The promoter for GGP from *Arabidopsis thaliana* (At4g26850) (SEQ ID NO: 102) and control promoters from a range of sources were cloned by PCR. The control promoters were TT8 (AT4G09820), EF1α (AT1G07940), Act2P (AT3G18780) and Act7P (AT5G09810).

Generation of the inactivated start codons or other deletions and mutations in the uORFs of the 5'-UTR was done by chemical synthesis (GenScript, www.genscript.com) of mutated and control sequences. In the inactivated versions, the ATG or ACG start codons of the uORFs were changed to a TTG. Other changes were done by site-specific mutagenesis. There is a StuI site on the 5' side of the UTR 28 bp into the 5'-UTR which was used as the 5' border of the synthesized fragment. We added an extra CC to the 3' end of the synthesized genes to create a NcoI site (ccatgg) and removed the sequence equivalent to the synthesized fragment from the GGP-promoter-pGreenII 0800-5 LUC by digesting it with StuI and NcoI. Then the synthesized fragments were separately cloned into the vector to create the two versions with and without a uORF.

RNA Isolation and cDNA Synthesis:

Total RNA was isolated from 100 mg leaf tissue using a RNeasy Plant Mini kit (Qiagen) and concentrations were measured using a Nanodrop 1000 spectrophotometer (Thermo Fisher Scientific Inc.). Complementary DNA was then synthesized from 1 µg total RNA and random hexamers in a 10 µl total volume using a BluePrint Reagent Kit for Real Time PCR (Takara Bio Company) following manufacturer instructions. Following cDNA synthesis the preparation was diluted 75 times in preparation for quantitative real time PCR.

Quantitative PCR

Quantitative PCR was performed in 5 µl total volume using a LightCycler® 480 Real-Time PCR System (Roche Diagnostics) and the following primer pair: LUC1/2: 5'-TATCCGCTGGAAGATGGAAC-3' (SEQ ID NO:109); 5'-TCCACCTCGATATGTGCATC-3'. (SEQ ID NO:110) Primers were designed with annealing temperatures of 60 C using Primer3 (Rozen and Skaletsky, 2000, *Methods Mol Biol.* 132, 365. The luciferase primer pair amplifies regions from the 5'-end of the luciferase open reading frame. Reaction components (using LightCycler 480® SYBR Green I Master Mix) were as follows: 2 µM each primer, 1.25 µl diluted cDNA preparation. The standard cycling protocol with a Tm of 60° C. was used and relative quantification analysis normalized to Renilla transcripts was performed using The LightCycler® 480 Software (Roche Diagnostics).

Control Tests of the System Used

As the control gene promoter TT8 expressed about 10 times higher than the GGT promoter we considered the possibility that the TT8 promoter might have saturated the ability of the tobacco cell to express the transcript or translate the LUC and thus any inhibition would not be seen. To check this, we titrated the amount of *Agrobacterium* containing the TT8-LUC construct over a 200 fold range. The ratio of LUC/REN and the slope of the relationship between LUC and REN was unchanged by the amount of *Agrobacterium* injected (Table 1) showing little sign of any saturation of expression of the reporter genes. The TT8 promoter driven LUC values overlapped with the LUC values expressed using the GGP promoter. We also tested whether several different alternative promoters were inhibited by ascorbate. These included EF1α, Act2P, and Act7P. None of these promoters were negatively affected by ascorbate (Table 2) although in this experiment, the TT8 promoter strength was actual increased by ascorbate. In a third test we verified that the effect of ascorbate on the GGP promoter strength was not restricted to the kiwifruit GGP gene promoter by testing the same promoter from *Arabidopsis* GGP (At4g26850). As shown in FIG. 4, the response of the LUC/REN ratio to ascorbate was essentially identical for the two promoters from different species. In a final test, we checked whether expressing a gene to raise ascorbate (kiwifruit GGP) might in itself affect the results. Consequently we added an extra control gene in the form of a methyl transferase. While we got a small reduction in this experiment in the LUC/REN ratio of the added control gene (Table 3), this did not change the conclusion that increased ascorbate reduced the strength of the GGP promoter but had little effect of other control promoters.

Examples 2

Figure 14:
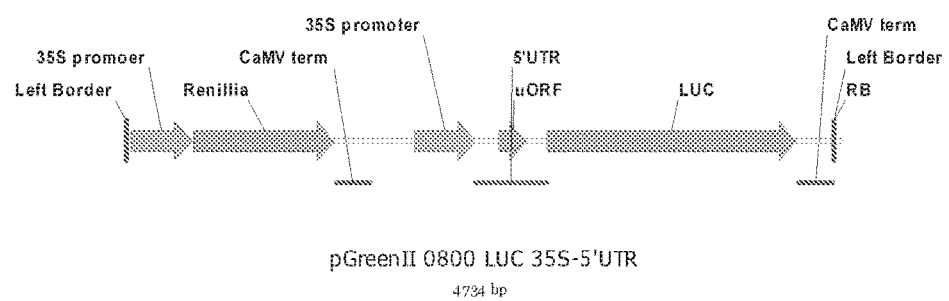
FIG. 14 shows a schematic illustrating the positioning of the pGreen 0800 based reporter gene construct designed to test the 5'UTR from GGP from different species.

Testing the Effect of Ascorbate on Other 5'UTR Sequences in the LUC/REN Reporter Assay Methods A 35S driven-LUC construct was derived from pGreen 0800 LUC (Hellens et al., 2000, *Plant Mol. Biol.* 42, 819), where a second copy of the 35S promoter without its 5'UTR was cloned into the multiple cloning site in front of the LUC coding sequence, and 5'UTRs from apple, potato and tomato (SEQ ID NO: 126, 127 and 128 respectively) were inserted between this 35S promoter and the beginning of the LUC coding sequence replacing the 35S 5'UTR (FIG. 14). The 5'UTR sequences are shown in FIG. 15.

These constructs were tested as described for other GGP promoter constructs in Example 1 above.

Results

Figure 16:
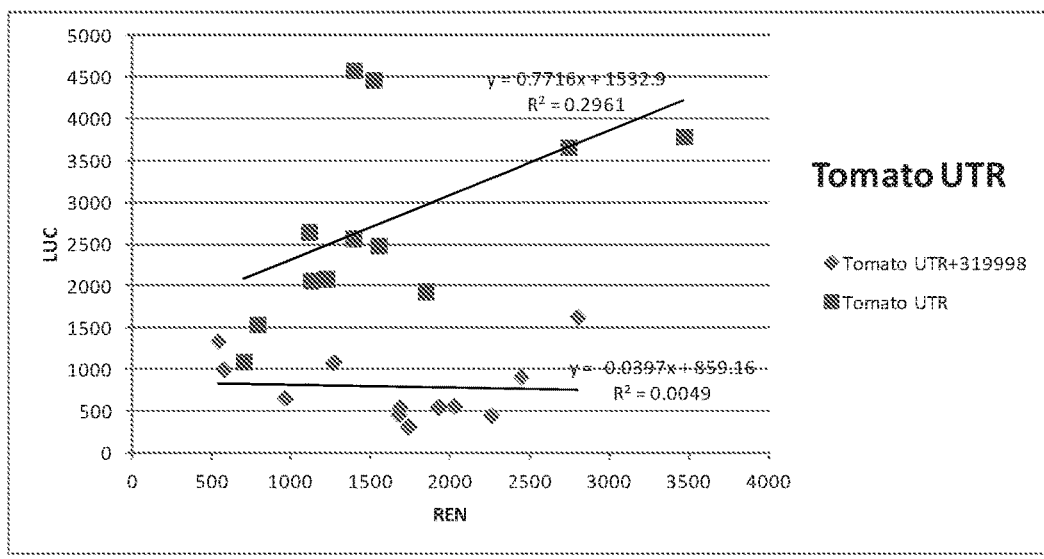
FIG. 16 shows a plot of LUC values versus REN at high (+319998) and low ascorbate for the tomato 5'UTR.
Figure 17:
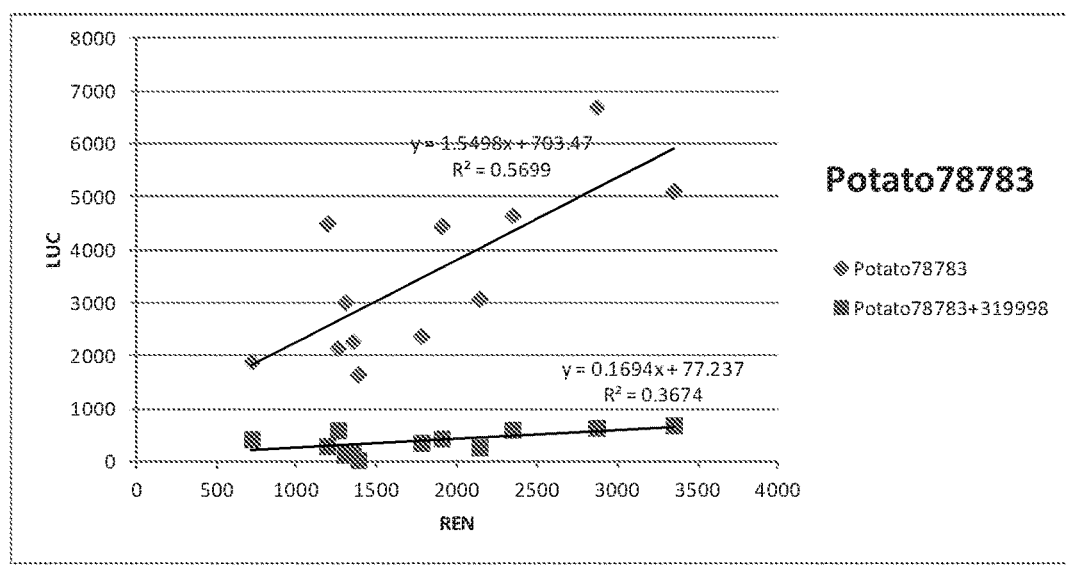
FIG. 17 shows a plot of LUC values versus REN at high (+319998) and low ascorbate for the potato 5'UTR.
Figure 18:
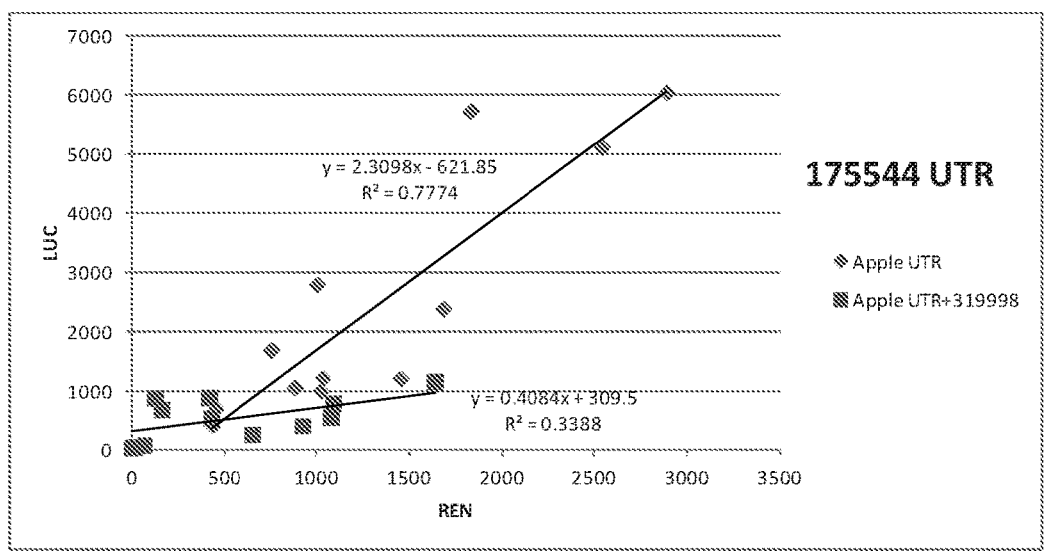
FIG. 18 shows a plot of LUC values versus REN at high (+319998) and low ascorbate for the apple 5'UTR.
Figure 19:
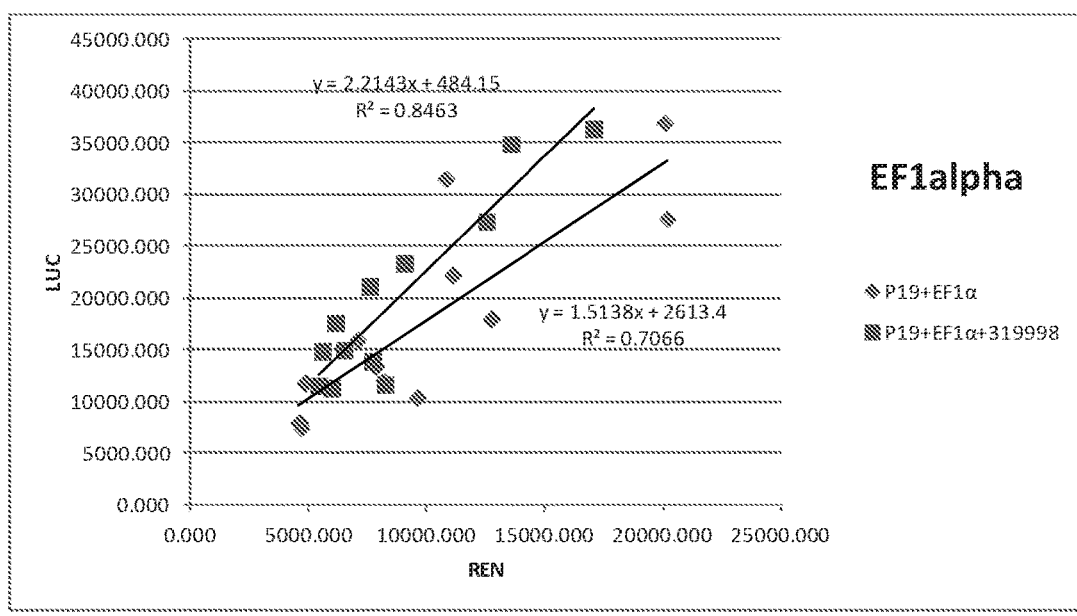
FIG. 19 shows a plot of LUC values versus REN at high (+319998) and low ascorbate for a control promoter-5'UTR-LUC construct. Note that the slope is lower at low ascorbate than at high ascorbate
Figure 20:
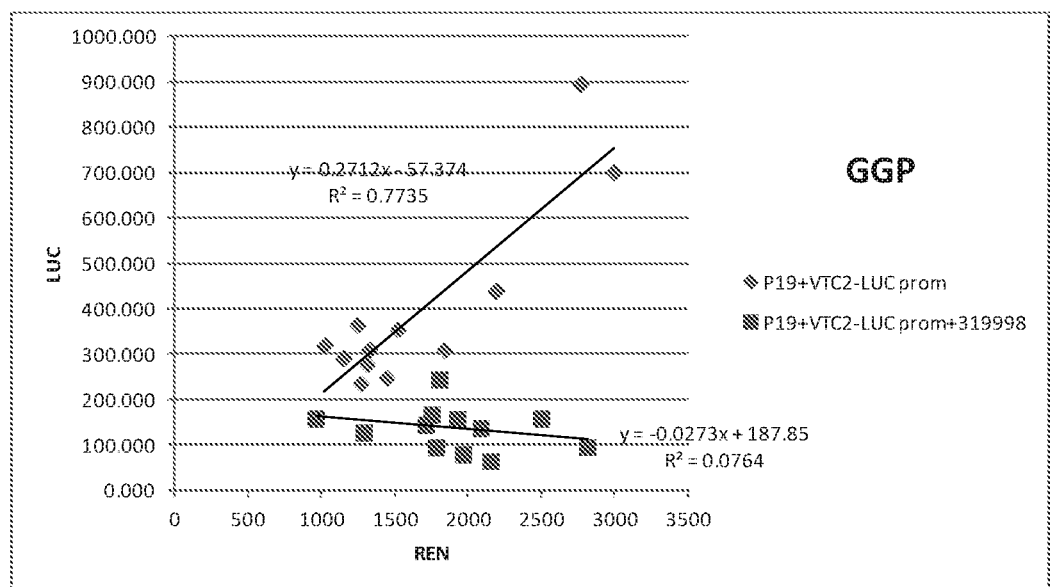
FIG. 20 shows a plot of LUC values versus REN at high (+319998) and low ascorbate for the wild type kiwifruit GGP promoter-5'UTR-LUC construct.

The LUC genes, each driven by different GGP 5'UTR inserts, were all down regulated by ascorbate (FIGS. 16, 17 and 18, Table 6). In each case both the LUC/REN ratios and the slope of the relationship between LUC and REN were reduced by ascorbate. In these experiments, the ascorbate increased less than shown in Example 1 (Table 6), possibly due to varying growth conditions (lower light and higher temperature) but the increased ascorbate still reduced the LUC values significantly. Also shown are corresponding data for a typical non-responsive promoter-5'UTR (EF1alpha: FIG. 19) and for the standard GGP promoter- 5'UTR (FIG. 20). The further variant 5'UTR sequences disclosed can of course be tested in the same way.

TABLE 6

| 5'UTR | Mean LUC/REN | Std error | p | Slope | $R^2$ | Mean ascorbate mg/100 g FW | Std error |
|---|---|---|---|---|---|---|---|
| Tomato low ascorbate | 1.88 | 0.21 | 0.000 | 0.77 | 0.30 | 19.1 | 1.7 |
| Tomato high ascorbate | 0.69 | 0.22 | | 0.04 | 0.00 | 36.6 | 1.5 |
| Potato low ascorbate | 2.03 | 0.22 | 0.000 | 1.55 | 0.57 | 21.5 | 1.4 |
| Potato high ascorbate | 0.30 | 0.04 | | 0.13 | 0.63 | 40.3 | 3.4 |
| Apple low ascorbate | 1.77 | 0.24 | 0.024 | 2.31 | 0.78 | 18.4 | 1.1 |
| Apple high ascorbate | 0.89 | 0.26 | | 0.41 | 0.34 | 33.6 | 2.9 |
| EF1alpha promoter low ascorbate | 1.821 | 0.15 | 0.028 | 1.51 | 0.71 | 19.1 | 0.6 |
| EF1alpha promoter high ascorbate | 2.278 | 0.13 | | 2.21 | 0.85 | 34.9 | 2.0 |

TABLE 6-continued

| 5'UTR | Mean LUC/REN | Std error | p | Slope | $R^2$ | Mean ascorbate mg/100 g FW | Std error |
|---|---|---|---|---|---|---|---|
| Kiwifruit GGP-5'UTR low ascorbate | 0.236 | 0.02 | 0.000 | 0.27 | 0.77 | 20.5 | 0.8 |
| Kiwifruit GGP-5'UTR. high ascorbate | 0.079 | 0.01 | | −0.03 | 0.08 | 40.3 | 1.9 |

Tabulation of LUC/REN ratios and slopes for plots of LUC against REN for various 5'UTR from GGPs from three different species. We also include a control promoter and its own 5'UTR and the original GGP promoter and 5'UTR used previously as controls. The p value is the statistical significance for the difference between high and low ascorbate for each construct.

CONCLUSION

The GGP 5'UTR constructs from these three different species tested all showed significant down regulation by increased ascorbate. Along with the 5'UTRs from GGPs from *Arabidopsis* and kiwifruit (Example 1), this makes a total of five diverse GGP 5'UTRs that have been tested and all have been shown to be down regulated by increased ascorbate, strongly suggesting that this is a widespread phenomenon.

SUMMARY OF SEQUENCES

| SEQ ID NO. | Molecule type | Species | Classification | Reference |
|---|---|---|---|---|
| 1 | polypeptide | *Actinidia eriantha* | Dicot | uORF peptide |
| 2 | polypeptide | *Cucumis sativus* | Dicot | uORF peptide |
| 3 | polypeptide | *Glycine max* | Dicot | uORF peptide |
| 4 | polypeptide | *Solanum lycopersicum* | Dicot | uORF peptide |
| 5 | polypeptide | *Vitis vinifera* | Dicot | uORF peptide |
| 6 | polypeptide | *Arabidopsis thaliana* | Dicot | uORF peptide |
| 7 | polypeptide | *Arabidopsis thaliana* | Dicot | uORF peptide at5g55120 |
| 8 | polypeptide | *Malus x domesticus* | Dicot | uORF peptide |
| 9 | polypeptide | *Medicago truncatula* | Dicot | uORF peptide |
| 10 | polypeptide | *Populus trichocarpa* | Dicot | uORF peptide |
| 11 | polypeptide | *Picea sitchensis* | Pinophyta | uORF peptide |
| 12 | polypeptide | *Physcomitrella patens* | Bryophyta | uORF peptide |
| 13 | polypeptide | *Actinidia arguta* | Dicot | uORF peptide |
| 14 | polypeptide | *Actinidia eriantha* | Dicot | uORF peptide |
| 15 | polypeptide | *Actinidia chinensis* | Dicot | uORF peptide |
| 16 | polypeptide | *Fragaria vulgaris* | Dicot | uORF peptide |
| 17 | polypeptide | *Solanum tuberosum* | Dicot | uORF peptide |
| 18 | polypeptide | *Chlamydomonas reinhardtii* | Protista | uORF peptide |
| 19 | polypeptide | *Zea mays* | Monocot | uORF peptide |
| 20 | polypeptide | *Selaginella moellendorffii* | Lycopodiophyta | uORF peptide |
| 21 | polypeptide | *Actinidia eriantha* | Dicot | uORF peptide conserved region |
| 22 | polypeptide | *Cucumis sativus* | Dicot | uORF peptide conserved region |
| 23 | polypeptide | *Glycine max* | Dicot | uORF peptide conserved region |
| 24 | polypeptide | *Solanum lycopersicum* | Dicot | uORF peptide conserved region |
| 25 | polypeptide | *Vitis vinifera* | Dicot | uORF peptide conserved region |

-continued

| SUMMARY OF SEQUENCES | | | | |
|---|---|---|---|---|
| SEQ ID NO. | Molecule type | Species | Classification | Reference |
| 26 | polypeptide | Arabidopsis thaliana | Dicot | uORF peptide conserved region at4g26850 |
| 27 | polypeptide | Arabidopsis thaliana | Dicot | uORF peptide conserved region at5g55120 |
| 28 | polypeptide | Malus x domesticus | Dicot | uORF peptide conserved region |
| 29 | polypeptide | Medicago truncatula | Dicot | uORF peptide conserved region |
| 30 | polypeptide | Populus trichocarpa | Dicot | uORF peptide conserved region |
| 31 | polypeptide | Picea sitchensis | Pinophyta | uORF peptide conserved region |
| 32 | polypeptide | Physcomitrella patens | Bryophyta | uORF peptide conserved region |
| 33 | polypeptide | Actinidia arguta | Dicot | uORF peptide conserved region |
| 34 | polypeptide | Actinidia eriantha | Dicot | uORF peptide conserved region |
| 35 | polypeptide | Actinidia chinensis | Dicot | uORF peptide conserved region |
| 36 | polypeptide | Fragaria vulgaris | Dicot | uORF peptide conserved region |
| 37 | polypeptide | Solanum tuberosum | Dicot | uORF peptide conserved region |
| 38 | polypeptide | Chlamydomonas reinhardtii | Protista | uORF peptide conserved region |
| 39 | polypeptide | Zea mays | Monocot | uORF peptide conserved region |
| 40 | polypeptide | Selaginella moellendorffii | Lycopodiophyta | uORF peptide conserved region |
| 41 | polynucleotide | Actinidia eriantha | Dicot | uORF DNA |
| 42 | polynucleotide | Cucumis sativus | Dicot | uORF DNA |
| 43 | polynucleotide | Glycine max | Dicot | uORF DNA |
| 44 | polynucleotide | Solanum lycopersicum | Dicot | uORF DNA |
| 45 | polynucleotide | Vitis vinifera | Dicot | uORF DNA |
| 46 | polynucleotide | Arabidopsis thaliana | Dicot | uORF DNA at4g26850 |
| 47 | polynucleotide | Arabidopsis thaliana | Dicot | uORF DNA at5g55120 |
| 48 | polynucleotide | Malus x domesticus | Dicot | uORF DNA |
| 49 | polynucleotide | Medicago truncatula | Dicot | uORF DNA |
| 50 | polynucleotide | Populus trichocarpa | Dicot | uORF DNA |
| 51 | polynucleotide | Picea sitchensis | Pinophyta | uORF DNA |
| 52 | polynucleotide | Physcomitrella patens | Bryophyta | uORF DNA |
| 53 | polynucleotide | Actinidia arguta | Dicot | uORF DNA |
| 54 | polynucleotide | Actinidia eriantha | Dicot | uORF DNA |
| 55 | polynucleotide | Actinidia chinensis | Dicot | uORF DNA |
| 56 | polynucleotide | Fragaria vulgaris | Dicot | uORF DNA |
| 57 | polynucleotide | Solanum tuberosum | Dicot | uORF DNA |
| 58 | polynucleotide | Chlamydomonas reinhardtii | Protista | uORF DNA |
| 59 | polynucleotide | Zea mays | Monocot | uORF DNA |
| 60 | polynucleotide | Selaginella moellendorffii | Lycopodiaphyta | uORF DNA |
| 61 | polynucleotide | Actinidia eriantha | Dicot | uORF DNA conserved region |
| 62 | polynucleotide | Cucumis sativus | Dicot | uORF DNA conserved region |
| 63 | polynucleotide | Glycine max | Dicot | uORF DNA conserved region |
| 64 | polynucleotide | Solanum lycopersicum | Dicot | uORF DNA conserved region |
| 65 | polynucleotide | Vitis vinifera | Dicot | uORF DNA conserved region |

-continued

| SEQ ID NO. | Molecule type | Species | Classification | Reference |
|---|---|---|---|---|
| 66 | polynucleotide | *Arabidopsis thaliana* | Dicot | uORF DNA conserved region at4g26850 |
| 67 | polynucleotide | *Arabidopsis thaliana* | Dicot | uORF DNA conserved region at5g55120 |
| 68 | polynucleotide | *Malus x domesticus* | Dicot | uORF DNA conserved region |
| 69 | polynucleotide | *Medicago truncatula* | Dicot | uORF DNA conserved region |
| 70 | polynucleotide | *Populus trichocarpa* | Dicot | uORF DNA conserved region |
| 71 | polynucleotide | *Picea sitchensis* | Pinophyta | uORF DNA conserved region |
| 72 | polynucleotide | *Physcomitrella patens* | Bryophyta | uORF DNA conserved region |
| 73 | polynucleotide | *Actinidia arguta* | Dicot | uORF DNA conserved region |
| 74 | polynucleotide | *Actinidia eriantha* | Dicot | uORF DNA conserved region |
| 75 | polynucleotide | *Actinidia chinensis* | Dicot | uORF DNA conserved region |
| 76 | polynucleotide | *Fragaria vulgaris* | Dicot | uORF DNA conserved region |
| 77 | polynucleotide | *Solanum tuberosum* | Dicot | uORF DNA conserved region |
| 78 | polynucleotide | *Chlamydomonas reinhardtii* | Protista | uORF DNA conserved region |
| 79 | polynucleotide | *Zea mays* | Monocot | uORF DNA conserved region |
| 80 | polynucleotide | *Selaginella moellendorffii* | Lycopodiophyta | uORF DNA conserved region |
| 81 | polynucleotide | *Actinidia eriantha* | Dicot | Whole 5'-UTR |
| 82 | polynucleotide | *Cucumis sativus* | Dicot | Whole 5'-UTR |
| 83 | polynucleotide | *Glycine max* | Dicot | Whole 5'-UTR |
| 84 | polynucleotide | *Solanum lycopersicum* | Dicot | Whole 5'-UTR |
| 85 | polynucleotide | *Vitis vinifera* | Dicot | Whole 5'-UTR |
| 86 | polynucleotide | *Arabidopsis thaliana* | Dicot | Whole 5'-UTR at4g26850 |
| 87 | polynucleotide | *Arabidopsis thaliana* | Dicot | Whole 5'-UTR at5g55120 |
| 88 | polynucleotide | *Malus x domesticus* | Dicot | Whole 5'-UTR |
| 89 | polynucleotide | *Medicago truncatula* | Dicot | Whole 5'-UTR |
| 90 | polynucleotide | *Populus trichocarpa* | Dicot | Whole 5'-UTR |
| 91 | polynucleotide | *Picea sitchensis* | Pinophyta | Whole 5'-UTR |
| 92 | polynucleotide | *Physcomitrella patens* | Bryophyta | Whole 5'-UTR |
| 93 | polynucleotide | *Actinidia arguta* | Dicot | Whole 5'-UTR |
| 94 | polynucleotide | *Actinidia eriantha* | Dicot | Whole 5'-UTR |
| 95 | polynucleotide | *Actinidia chinensis* | Dicot | Whole 5'-UTR |
| 96 | polynucleotide | *Fragaria vulgaris* | Dicot | Whole 5'-UTR |
| 97 | polynucleotide | *Solanum tuberosum* | Dicot | Whole 5'-UTR |
| 98 | polynucleotide | *Chlamydomonas reinhardtii* | Protista | Whole 5'-UTR |
| 99 | polynucleotide | *Zea mays* | Monocot | Whole 5'-UTR |
| 100 | polynucleotide | *Selaginella moellendorffii* | Lycopodiophyta | Whole 5'-UTR |
| 101 | polynucleotide | *Actinidia eriantha* | Dicot | GGP genomic promoter sequence |
| 102 | polynucleotide | *Arabidopsis thaliana* | Dicot | GGP genomic promoter sequence at4g26850 |
| 103 | polynucleotide | *Arabidopsis thaliana* | Dicot | GGP genomic promoter sequence at5g55120 |

-continued

SUMMARY OF SEQUENCES

| SEQ ID NO. | Molecule type | Species | Classification | Reference |
|---|---|---|---|---|
| 104 | polynucleotide | Malus x domesticus | Dicot | GGP2 genomic promoter sequence MDP0000288088 |
| 105 | polynucleotide | Malus x domesticus | Dicot | GGP1 genomic promoter sequence MDP0000172222 |
| 106 | polynucleotide | Malus x domesticus | Dicot | GGP3 genomic promoter sequence MDP0000191488 |
| 107 | polynucleotide | Actinidia chinensis | Dicot | GGP genomic promoter sequence |
| 108 | polypeptide | Artificial | Consensus | Consensus motif |
| 109 | polynucleotide | Artificial | Primer | LUC1 |
| 110 | polynucleotide | Artificial | Primer | LUC2 |
| 111 | polynucleotide | Cucumis sativus | Dicot | Sub-sequence of 5'-UTR |
| 112 | polynucleotide | Actinidia eriantha | Dicot | Sub-sequence of 5'-UTR |
| 113 | polynucleotide | Actinidia arguta | Dicot | Sub-sequence of 5'-UTR |
| 114 | polynucleotide | Actinidia eriantha | Dicot | Sub-sequence of 5'-UTR |
| 115 | polynucleotide | Actinidia chinensis | Dicot | Sub-sequence of 5'-UTR |
| 116 | polynucleotide | Malus x domesticus | Dicot | Sub-sequence of 5'-UTR |
| 117 | polynucleotide | Fragaria vulgaris | Dicot | Sub-sequence of 5'-UTR |
| 118 | polynucleotide | Arabidopsis thaliana | Dicot | Sub-sequence of 5'-UTR |
| 119 | polynucleotide | Arabidopsis thaliana | Dicot | Sub-sequence of 5'-UTR |
| 120 | polynucleotide | Populus trichocarpa | Dicot | Sub-sequence of 5'-UTR |
| 121 | polynucleotide | Glycine max | Dicot | Sub-sequence of 5'-UTR |
| 122 | polynucleotide | Medicago truncatula | Dicot | Sub-sequence of 5'-UTR |
| 123 | polynucleotide | Solanum lycopersicum | Dicot | Sub-sequence of 5'-UTR |
| 124 | polynucleotide | Solanum tuberosum | Dicot | Sub-sequence of 5'-UTR |
| 125 | polynucleotide | Vitis vinifera | Dicot | Sub-sequence of 5'-UTR |
| 126 | polynucleotide | Solanum lycopersicum | Dicot | Whole 5'-UTR |
| 127 | polynucleotide | Solanum tuberosum | Dicot | Whole 5'-UTR |
| 128 | polynucleotide | Malus x domesticus | Dicot | Whole 5'-UTR |
| 129 | polynucleotide | Solanum lycopersicum | Dicot | uORF DNA |
| 130 | polynucleotide | Solanum tuberosum | Dicot | uORF DNA |
| 131 | polynucleotide | Malus x domesticus | Dicot | uORF DNA |
| 132 | polypeptide | Solanum lycopersicum | Dicot | uORF peptide |
| 133 | polypeptide | Solanum tuberosum | Dicot | uORF peptide |
| 134 | polypeptide | Malus x domesticus | Dicot | uORF peptide |
| 135 | polypeptide | Solanum lycopersicum | Dicot | uORF peptide conserved region |
| 136 | polypeptide | Solanum tuberosum | Dicot | uORF peptide conserved region |
| 137 | polypeptide | Malus x domesticus | Dicot | uORF peptide conserved region |
| 138 | polynucleotide | Solanum lycopersicum | Dicot | uORF DNA conserved region |

SUMMARY OF SEQUENCES

| SEQ ID NO. | Molecule type | Species | Classification | Reference |
|---|---|---|---|---|
| 139 | polynucleotide | *Solanum tuberosum* | Dicot | uORF DNA conserved region |
| 140 | polynucleotide | *Malus* x *domesticus* | Dicot | uORF DNA conserved region |

---

The invention claimed is:

1. A method for producing a plant cell or plant with at least one of:
   a) increased GDP-L-Galactose phosphorylase (GGP) translation,
   b) increased GGP production,
   c) increased GGP activity, and
   d) increased ascorbate production,
   the method comprising modification of the 5'-UTR of a GGP gene in the plant cell or plant, wherein the 5'UTR comprises at least one of:
   i) a sequence with at least 70% identity to any one of SEQ ID NOs: 41-100, and 111-131, and
   ii) a sequence encoding a polypeptide with at least 70% identity to any one of SEQ ID NOs: 1-40, 108, and 132 to 140;
   wherein the modification disrupts the function of an upstream open reading frame (uORF) encoded by the 5'UTR; and wherein said modification is at least one of a deletion, an addition, or a substitution of at least one nucleotide in the 5'UTR.

2. The method of claim 1 wherein the modification is in the uORF sequence in the 5'UTR.

3. The method of claim 2 wherein the uORF has a sequence selected from any one of SEQ ID NO: 41 to 60 and 129 to 131 or a variant thereof with at least 70% identity to any one of SEQ ID NO: 41 to 60 and 129 and 131.

4. A method for selecting a plant with at least one of:
   a) increased GGP translation,
   b) increased GGP production,
   c) increased GGP activity, and
   d) increased ascorbate production,
   the method comprising testing of a plant for the presence of a first polymorphism in a polynucleotide comprising a sequence encoding a polypeptide with at least 70% identity to an amino acid sequence selected from SEQ ID NO:1 to 20, and 132 to 134 in the plant, or a further polymorphism linked to the first polymorphism, wherein the first polymorphism disrupts expression of the polypeptide.

5. The method of claim 4 which includes the step of separating the selected plant from one or more of non-selected plants.

6. A method of producing ascorbate, the method comprising extracting ascorbate from a plant cell or plant produced by the method of claim 1 or selected by the method of claim 4.

7. A plant cell or plant produced by the method of claim 1.

8. The plant cell or plant of claim 7 with at least one of:
   a) increased GGP translation,
   b) increased GGP production,
   c) increased GGP activity, and
   d) increased ascorbate production,
   wherein the plant cell or plant comprises a modification in the 5'-UTR of a GGP gene in the plant cell or plant, wherein the 5'-UTR comprises at least one of:
   i) a sequence with at least 80% identity to any one of 41-100, and 111-131, and
   ii) a sequence encoding a polypeptide with at least 80% identity to any one of SEQ ID NO: 1-40, 108, and 132 to 140
   wherein the modification disrupts the function of a uORF encoded by the 5'-UTR, and wherein said modification is at least one of a deletion, an addition, or a substitution of at least one nucleotide in the 5'-UTR.

9. A method of producing ascorbate, the method comprising extracting ascorbate from the plant cell or plant of claim 7.

* * * * *